US008874420B2

(12) United States Patent
Guo et al.

(10) Patent No.: US 8,874,420 B2
(45) Date of Patent: Oct. 28, 2014

(54) METHODS FOR INCREASING GENETIC GAIN IN A BREEDING POPULATION

(75) Inventors: Zhigang Guo, Champaign, IL (US); Venkata Krishna Kishore, Bloomington, IL (US)

(73) Assignee: Syngenta Participations AG, Basel (CH)

( * ) Notice: Subject to any disclaimer, the term of this patent is extended or adjusted under 35 U.S.C. 154(b) by 107 days.

(21) Appl. No.: 13/307,733

(22) Filed: Nov. 30, 2011

(65) Prior Publication Data

US 2012/0151625 A1    Jun. 14, 2012

Related U.S. Application Data

(60) Provisional application No. 61/418,135, filed on Nov. 30, 2010.

(51) Int. Cl.
| | | |
|---|---|---|
| *G06G 7/48* | (2006.01) | |
| *G06G 7/58* | (2006.01) | |
| *G01N 33/48* | (2006.01) | |
| *G01N 31/00* | (2006.01) | |
| *G06F 19/18* | (2011.01) | |
| *A01H 1/04* | (2006.01) | |

(52) U.S. Cl.
CPC . *A01H 1/04* (2013.01); *G06F 19/18* (2013.01)
USPC ............. 703/11; 703/12; 702/19; 702/20

(58) Field of Classification Search
CPC ............ G06N 3/126; A01K 2217/206; A01K 2217/052; G06F 19/18; G01N 33/5088
See application file for complete search history.

(56) References Cited

U.S. PATENT DOCUMENTS

| | | | |
|---|---|---|---|
| 5,492,547 A | 2/1996 | Johnson | |
| 2005/0144664 A1 | 6/2005 | Smith et al. | |
| 2007/0105107 A1* | 5/2007 | Wang et al. ................. | 435/6 |
| 2008/0216188 A1* | 9/2008 | Ragot et al. ................ | 800/260 |
| 2010/0145624 A1* | 6/2010 | Kishore et al. ............. | 702/19 |

FOREIGN PATENT DOCUMENTS

WO    WO 2008/087185    7/2008

OTHER PUBLICATIONS

Beavis (1994) The power and deceit of QTL experiments: lessons from comparative QTL studies, pp. 250-266 in 49th Annual Corn and Sorghum Industry Research Conference. ASTA, Washington, DC.
Bernardo & Yu (2007) Prospects for genomewide selection for quantitative traits in maize, Crop Science 47:1082-1090.
Churchill & Doerge (1994) Empirical threshold values for quantitative trait mapping, Genetics 138:963-971.
Devlin & Risch (1995) A comparison of linkage disequilibrium measures for fine-scale mapping, Genomics 29:311-322.
Fisch & Melchinger (2006) Marker-based prediction of the parental genome contribution to inbred lines derived from biparental crosses. Genetics. Oct. 2006;174(2):795-803. Epub Aug. 3, 2006.

(Continued)

*Primary Examiner* — Larry D Riggs, II
(74) *Attorney, Agent, or Firm* — Dale Skalla

(57) ABSTRACT

Methods for method for increasing genetic gain in a breeding process are provided. Also provided are methods for choosing breeding pairs predicted to produce progeny having desired phenotypes, methods for increasing the likelihood of producing progeny individual having desired phenotypes, methods for generating progeny individual having desired genotypes and/or phenotypes, progeny produced thereby, and cells, seeds, parts, and tissues cultures thereof.

22 Claims, 4 Drawing Sheets

(56) References Cited

OTHER PUBLICATIONS

Frisch et al. (2000) PLABSIM: software for simulation of marker-assisted backcrossing. J Hered Jan.-Feb.;91(1):86-7.

Gusfield (2002) Haplotyping as perfect phylogeny: conceptual framework and efficient solutions, in Proceedings of RECOMB 2002: The 6th Annual International Conference on Computational Biology 2002, ACM Press, Washington, DC, United States of America, pp. 166-175.

Harville (1977) Maximum Likelihood Approaches to Variance Component Estimation and to Related Problems, J Am Stat Assoc 72:320-338.

Hayes et al. (2009) Invited review: Genomic selection in dairy cattle: Progress and challenges. J Dairy Sci 92:433-443.

Henderson (1975) Best Linear Unbiased Estimation and Prediction under a Selection Model. Biometrics (International Biometric Society) 31 (2): 423-448.

Hospital et al. (1996) A general algorithm to compute multilocus genotype frequencies under various mating systems. Comput Appl Biosci Dec.;12(6):455-62.

Jannink et al. (2010) Genomic selection in plant breeding: from theory to practice. Brief Funct Genomic 9:166-177.

Lande & Thompson (1990) Efficiency of marker-assisted selection in the improvement of quantitative traits. Genetics 124:743-756.

Lorenzana & Bernardo (2009) Accuracy of genotypic value predictions for marker-based selection in biparental plant populations. Theor Appl Genet 120:151-161.

Luan et al. (2009) the accuracy of genomic selection in Norwegian red cattle assessed by cross-validation. Genetics 183:1119-1126.

Maurer et al. (2004) Plabsoft: software for simulation and data analysis in plant breeding. Conference paper, Genetic variation for plant breeding. Proceedings of the 17th EUCARPIA General Congress, Tulin, Austria, Sep. 8-11, 2004 pp. 359-362.

Meuwissen et al. (2001) Prediction of total genetic value using genome-wide dense marker maps, Genetics 157:1819-1829.

Notification of the Transmittal of the International Search Report and the Written Opinion of the International Searching Authority, or the Declaration, corresponding to international application PCT/US2011/062616 dated Mar. 19, 2012.

O'Connell (2000) Zero-recombinant haplotyping: applications to fine mapping using SNPs. Genet Epidemiol 19(Suppl1):S64-70.

Qian & Beckmann (2002) Minimum-recombinant haplotyping in pedigrees, Am J Hum Genet 70:1434-1445.

Servin et al. (2002) MDM: a program to compute fully informative genotype frequencies in complex breeding schemes. J Hered May-Jun.;93(3):227-8.

Utz et al. (1999) Bias and sampling error of the estimated proportion of genotypic variance explained by quantitative trait loci determined from experimental data in maize using cross validation and validation with independent samples. Genetics 154: 1839-1849.

\* cited by examiner

METHODS FOR INCREASING GENETIC GAIN IN A BREEDING POPULATION

CROSS REFERENCE TO RELATED APPLICATION

The presently disclosed subject matter claims the benefit of U.S. Provisional Patent Application Ser. No. 61/418,135 entitled "METHODS FOR INCREASING GENETIC GAIN IN A BREEDING POPULATION", filed Nov. 30, 2010, the disclosure of which is incorporated herein by reference in its entirety.

TECHNICAL FIELD

The presently disclosed subject matter relates to plant molecular genetics and breeding, particularly to methods for increasing genetic gain of genome-wide selections in breeding populations.

BACKGROUND

In plant breeding, conventional selection is based on phenotypic assessments of progeny in breeding populations. Progeny are typically phenotyped during the growing season, and superior individuals are selected based on their phenotypic scores. For the majority of field crops, there is only one growing season per year. Hence, a limitation of phenotypic selection is that it is routinely limited to one cycle within each year. Another frequent shortcoming of phenotypic selection is the influence of environmental noise on phenotypic expression of traits. This environmental noise can lead to biases in selection and decreases in the selection efficiencies of phenotypic selection.

The development of molecular technologies facilitates methods for utilizing molecular markers to speed up selective breeding processes. One such molecular technology is marker-assisted selection (MAS; also referred to as "marker-aided breeding"). With MAS, one first identifies one or more quantitative trait loci (QTLs) associated with a trait of interest, and then employs analyses of these QTLs in subsequent selections (Lande & Thompson, 1990). In general, MAS can be performed over multiple cycles per year, and genetic gain can be enhanced by intensive selections of targeted QTLs.

However, it is often difficult to identify all of the QTLs that are associated with a particular trait of interest, thereby reducing the overall effectiveness of MAS (Utz et al. 1999; Jannink et al., 2010). This is due to missing QTLs with small effects during QTL identification due to various technical reasons (e.g., lower heritability, small sample sizes, etc.). Failure to identify such QTLs can make MAS difficult and/or inefficient to employ for improving important traits such as crop yield. In addition, QTL effects can be overestimated (Beavis, 1994), which further reduces the efficiency of MAS (Jannink et al., 2010).

Genome-wide selection (GWS; Meuwissen et al., 2001) is a technique that has been proposed to address some of the shortcomings of MAS (Bernardo and Yu, 2007; Jannink et al., 2010). The GWS strategy incorporates all genetic markers available for a given genome into a prediction model simultaneously, thereby reducing risks of missing or inaccurately calculating effects of QTLs with minor effects. Each marker is generally considered to be a putative QTL and all markers are combined to predict the genomic breeding values (GBV) of progeny with GWS. Simulations and empirical studies have verified advantages of GWS over MAS and PS (Meuwissen et al., 2001; Bernardo and Yu, 2007; Hayes et al., 2009; Lorenzana & Bernardo, 2009; Luan et al., 2009).

Typically, GWS can be used to select superior progeny based on their own particular GBVs. (Bernardo & Yu, 2007; Jannink et al., 2010). For example, GWS is generally used to estimate the effects of all assayed markers based on a training population, allowing for the calculation of an overall GBV for each progeny based on the progeny's genome. Progeny can then be ranked with respect to GBV, and the top progeny can be promoted to one or more further cycles of breeding & Yu However, a given selection strategy might not be optimal for GWS. For example, crossing two top lines selected in a given cycle does not necessarily generate highly-performing progeny by breeding Therefore, new methods are needed that outperform conventional GBV-based MAS in order to maximize the benefits of GWS on selective breeding strategies.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

In some embodiments, the presently disclosed subject matter provides methods for increasing genetic gain in a breeding population. In some embodiments, the methods comprise (a) providing effects with respect to a trait of interest of a plurality of genome-wide markers in a breeding population comprising a plurality of potential breeding partners; (b) selecting from the breeding population a first breeding pair comprising a first breeding partner and a second breeding partner, wherein crossing the first breeding partner and the second breeding partner would produce a segregating progeny population; (c) inferring or determining haplotypes with respect to the plurality of genome-wide markers for the first breeding partner and the second breeding partner; (d) simulating a cross between the first breeding partner and the second breeding partner to produce a progeny generation, each member of the progeny generation comprising a simulated genotype; (e) calculating a genetic potential value of the progeny generation, wherein the genetic potential value of the progeny generation is the mean of the genomic breeding values of the simulated genotypes of the member of the progeny generation; (f) repeating steps (b)-(e) one or more times, wherein in each iteration of step (b), the selecting comprises selecting a different first breeding partner, a different second breeding partner, or both from the breeding population; (g) ranking each simulated cross of step (d) based on the genetic potential values calculated in step (e); and (h) selecting one or more breeding pairs based on the ranking of step (g), wherein crossing the breeding pair selected in step (g) is predicted to generate progeny with increased genetic gain. In some embodiments, the presently disclosed methods further comprise repeating steps (b)-(e) and (g) such that at least one mean performance value calculated in step (e) exceeds a predetermined value.

The presently disclosed subject matter also provides in some embodiments methods for choosing breeding pairs predicted to produce progeny having desired phenotypes. In some embodiments, the methods comprise (a) estimating effects with respect to a trait of interest of a plurality of genome-wide markers in a biparental breeding population comprising a plurality of potential breeding partners; (b) selecting a first and a second breeding partner from the biparental breeding population, wherein the haplotype of each of the first breeding partner and the second breeding partner is known or is predictable with respect to the plurality of genetic markers; (c) inferring or determining haplotypes with respect to the plurality of genome-wide markers for the first breeding partner and the second breeding partner; (d) simulating a cross between the first breeding partner and the second breeding partner to produce a progeny generation, each member of the progeny generation comprising a simulated genotype; (e) calculating a genetic potential value of the progeny generation, wherein the genetic potential value of the progeny generation is the mean of the genomic breeding values of the simulated genotypes of the member of the progeny generation; (f) repeating steps (b)-(e) one or more times, wherein in each iteration of step (b), the selecting comprises selecting a different first breeding partner, a different second breeding partner, or both from the breeding population; (g) ranking each simulated cross of step (d) based on the genetic potential values calculated in step (e); and (h) selecting one or more breeding pairs based on the ranking of step (g), wherein the breeding pair is predicted to produce a progeny with the desired phenotype.

The presently disclosed subject matter also provides in some embodiments methods for increasing the likelihood of producing progeny individuals having desired phenotypes. In some embodiments, the methods comprise (a) providing effects with respect to a trait of interest of a plurality of genome-wide markers in a breeding population comprising a plurality of potential breeding partners; (b) selecting from the breeding population a first breeding pair comprising a first breeding partner and a second breeding partner, wherein crossing the first breeding partner and the second breeding partner would produce a segregating progeny population; (c) inferring haplotypes with respect to the plurality of genome-wide markers for the first breeding partner and the second breeding partner; (d) simulating a cross between the first breeding partner and the second breeding partner to produce a progeny generation, each member of the progeny generation comprising a simulated genotype; (e) calculating a genetic potential value of the progeny generation, wherein the genetic potential value of the progeny generation can be calculated as the mean of the genomic breeding values of the simulated genotypes of the member of the progeny generation, or it can be calculated based on the right tail or left tail of the distribution of the genomic breeding values; (f) repeating steps (b)-(e) one or more times, wherein in each iteration of step (b), the selecting comprises selecting a different first breeding partner, a different second breeding partner, or both from the breeding population; (g) ranking each simulated cross of step (d) based on the genetic potential values calculated in step (e); and (h) selecting one or more breeding pairs based on the ranking of step (g), wherein each of the one or more breeding pairs is predicted to have an increased likelihood of producing a progeny having the desired phenotype versus other breeding pairs in the breeding population.

The presently disclosed subject matter also provides methods for generating progeny individuals having desired genotypes. In some embodiments, the methods comprise (a) providing effects with respect to a trait of interest of a plurality of genome-wide markers in a breeding population comprising a plurality of potential breeding partners; (b) selecting from the breeding population a first breeding pair comprising a first breeding partner and a second breeding partner, wherein crossing the first breeding partner and the second breeding partner would produce a segregating progeny population; (c) inferring haplotypes with respect to the plurality of genome-wide markers for the first breeding partner and the second breeding partner; (d) simulating a cross between the first breeding partner and the second breeding partner to produce a progeny generation, each member of the progeny generation comprising a simulated genotype; (e) calculating a genetic potential value of the progeny generation, wherein the genetic potential value of the progeny generation is the mean of the genomic breeding values of the simulated genotypes of the member of the progeny generation; (f) repeating steps (b)-(e) one or more times, wherein in each iteration of step (b), the selecting comprises selecting a different first breeding partner, a different second breeding partner, or both from the breeding population; (g) ranking each simulated cross of step (d) based on the genetic potential values calculated in step (e); (h) selecting one or more breeding pairs based on the ranking of step (g); and (i) breeding the one or more breeding pairs selected in step (h) to generate a progeny individual having a desired genotype.

The presently disclosed subject matter also provides methods for generating progeny individuals having desired phenotypes. In some embodiments, the methods comprise (a) estimating effects with respect to a trait of interest of a plurality of genome-wide markers in a breeding population comprising a plurality of potential breeding partners; (b) selecting from the breeding population a first breeding pair comprising a first breeding partner and a second breeding partner, wherein crossing the first breeding partner and the second breeding partner would produce a segregating progeny population; (c) inferring haplotypes with respect to the plurality of genome-wide markers for the first breeding partner and the second breeding partner; (d) simulating a cross between the first breeding partner and the second breeding partner to produce a progeny generation, each member of the progeny generation comprising a simulated genotype; (e) calculating a genetic potential value of the progeny generation, wherein the genetic potential value of the progeny generation is the mean of the genomic breeding values of the simulated genotypes of the member of the progeny generation; (f) repeating steps (b)-(e) one or more times, wherein in each iteration of step (b), the selecting comprises selecting a different first breeding partner, a different second breeding partner, or both from the breeding population; (g) ranking each simulated cross of step (d) based on the genetic potential values calculated in step (e); (h) selecting one or more breeding pairs based on the ranking of step (g); and (i) breeding the one or more breeding pairs selected in step (h) to generate a progeny individual having a desired genotype.

In some embodiments of the presently disclosed methods, each breeding partner is a plant. In some embodiments, the plant is selected from the group consisting of maize, wheat, barley, rice, sugar beet, sunflower, winter oilseed rape, canola, tomato, pepper, melon, watermelon, broccoli, cauliflower, Brussel sprouts, lettuce, spinach, sugar cane, coffee, cocoa, pine, poplar, eucalyptus, apple tree, and grape. In some embodiments, the plant is maize.

In some embodiments of the presently disclosed methods, each breeding partner is an inbred individual.

In some embodiments of the presently disclosed methods, the breeding partners are the same individual.

In some embodiments of the presently disclosed methods, the one or more genetic markers are selected from the group consisting of a single nucleotide polymorphism (SNP), an insertion/deletion (indel), a simple sequence repeat (SSR), a restriction fragment length polymorphism (RFLP), a random amplified polymorphic DNA (RAPD), a cleaved amplified polymorphic sequence (CAPS) marker, a Diversity Arrays Technology (DArT) marker, an amplified fragment length polymorphism (AFLP), and combinations thereof.

In some embodiments of the presently disclosed methods, the one or more genetic markers comprise at least one marker present within every 5 cM, 3 cM, 2 cM, 1 cM, 0.5 cM, or 0.25 cM interval in the genomes of the breeding partners.

In some embodiments of the presently disclosed methods, the inferring step, the simulating step, the calculating step, or combinations thereof includes consideration of expected rates of recombination between adjacent genome-wide markers. In some embodiments, the rate of recombination between the at least one of the one or more genetic markers and the genetic locus associated with the desired phenotype is zero.

In some embodiments of the presently disclosed methods, the inferring step, the simulating step, or both are performed by a suitably-programmed computer.

In some embodiments of the presently disclosed methods, the simulating step comprises simulating at least 100, 500, or 1000 progeny in the progeny generation.

In some embodiments of the presently disclosed methods, the estimating comprises estimating effects with respect to the desired phenotype of the plurality of genome-wide markers based on phenotypic best linear unbiased predictions (BLUPs) and marker genotypic data in the biparental breeding population using genome-wide best linear unbiased prediction (GBLUP). In some embodiments, the estimating comprising estimating genetic variance by restrained maximum likelihood estimation (REML) based on phenotypic data from multiple locations using Equation (1) as defined herein.

In some embodiments of the presently disclosed methods, the inferring comprising employing a minimum recombination principle (MRP).

In some embodiments of the presently disclosed methods, the breeding population consists of n members and the repeating comprises simulating all n(n−1)/2 unique crosses of the members of the breeding population.

In some embodiments of the presently disclosed methods, the trait of interest comprises at least two independent traits of interest. In some embodiments, the presently disclosed methods further comprise assigning to each independent trait of interest an importance value relative to the other independent traits.

In some embodiments of the presently disclosed methods, the selecting one or more breeding pairs based on the ranking of step (g) comprises selecting the breeding pairs for which the genetic potential values of the progeny generations are ranked in the top 20%, 10%, 5%, or 1%.

The presently disclosed subject matter also provides in some embodiments progeny individuals generated by the presently disclosed methods. In some embodiments, the individual is a plant.

The presently disclosed subject matter also provides in some embodiments cells from plants generated by the presently disclosed methods, including but not limited to seeds thereof and/or progeny therefrom.

Thus, it is an object of the presently disclosed subject matter to provide methods for increasing genetic gain in breeding populations.

An object of the presently disclosed subject matter having been stated hereinabove and which is achieved in whole or in part by the presently disclosed subject matter, other objects will become evident as the description proceeds when taken in connection with the accompanying Figures as best described herein below.

Figure 1:
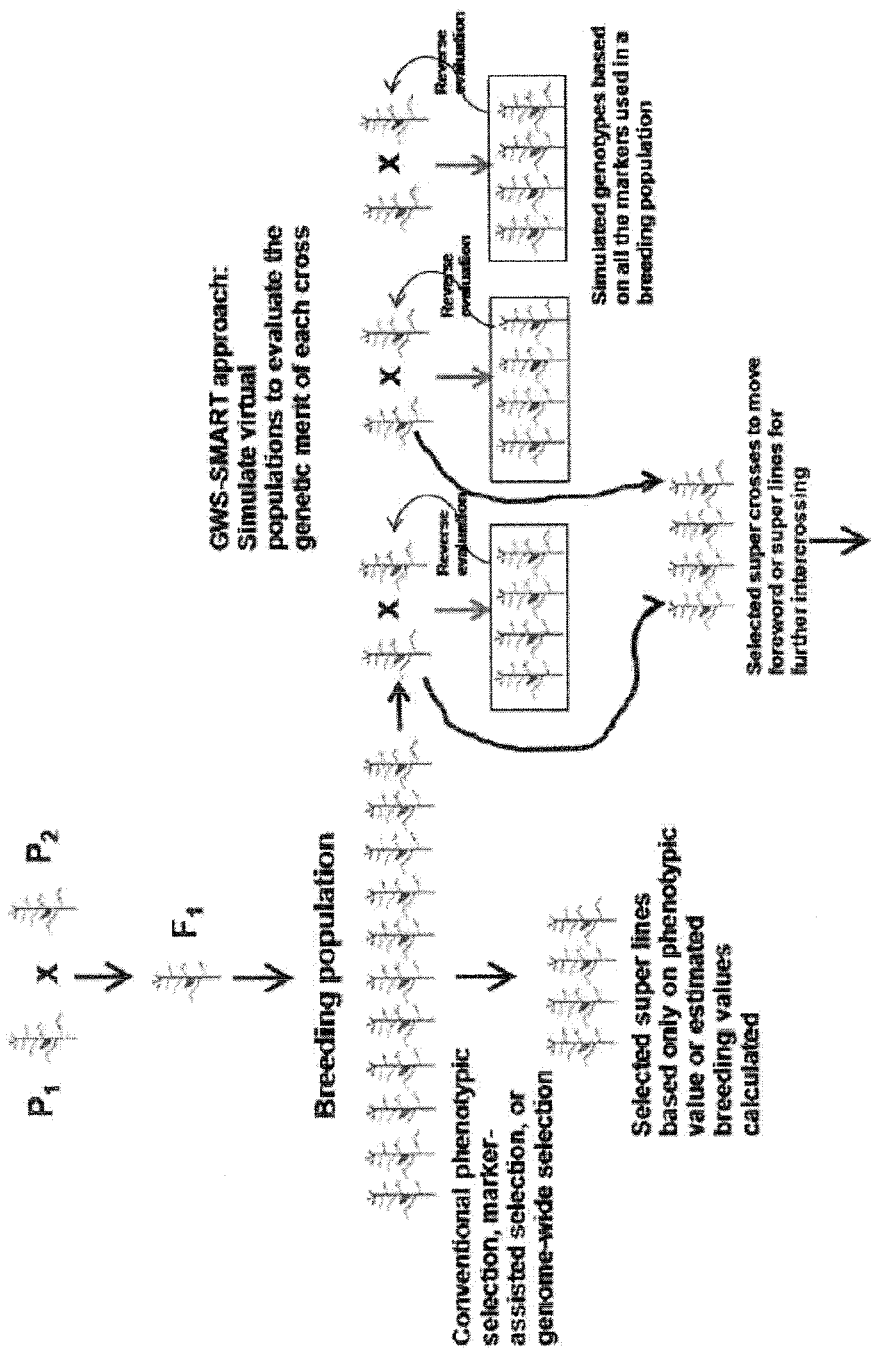
FIG. 1 is a comparison of conventional breeding methods to an exemplary method of the presently disclosed subject matter termed Genome-Wide Selection—Simulated Marker-Assisted Recurrent Testing of progeny (GWS-SMART). A first parent ($P_1$) and a second parent ($P_2$) are bred to create a first generation ($F_1$), which is used to create a breeding population. In the convention breeding method depicted on the left side of FIG. 1, marker-assisted selection (MAS) and/or genome-wide selection (GWS) are employed in an effort to identify members of the breeding population for further breeding. In subsequent breeding generations, however, the selected lines ("super lines") are chosen based only on phenotypic values and/or estimated breeding values calculated from the MAS and/or GWS approaches.

In the GWS-SMART approach depicted in the right side of FIG. 1, virtual populations are simulated to evaluate the genetic merit of possible crosses of the members of the breeding population (in some embodiments, each possible cross is simulated), and the simulated genotypes based on all of the markers used in the breeding population are used to reverse evaluate the relative merits of individual crosses of the breeding population. Based on this reverse evaluation, particularly desirable crosses ("super crosses") can be selected for further breedings and/or super lines can be selected for further intercrossing.

Figure 2:
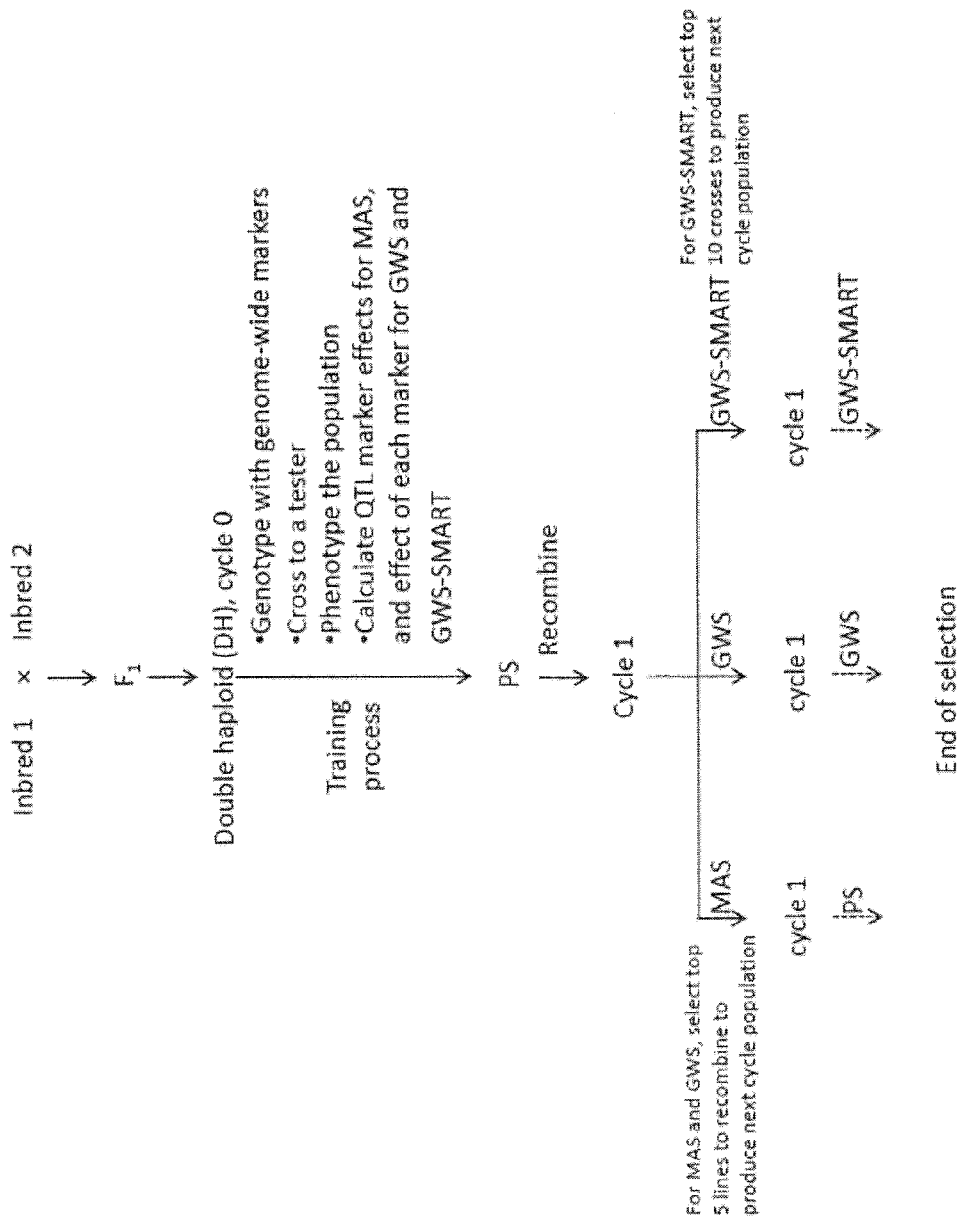

FIG. 2 is the simulating scheme used to compare MAS, GWS, and GWS-SMART described in EXAMPLE 1.

Figure 3:
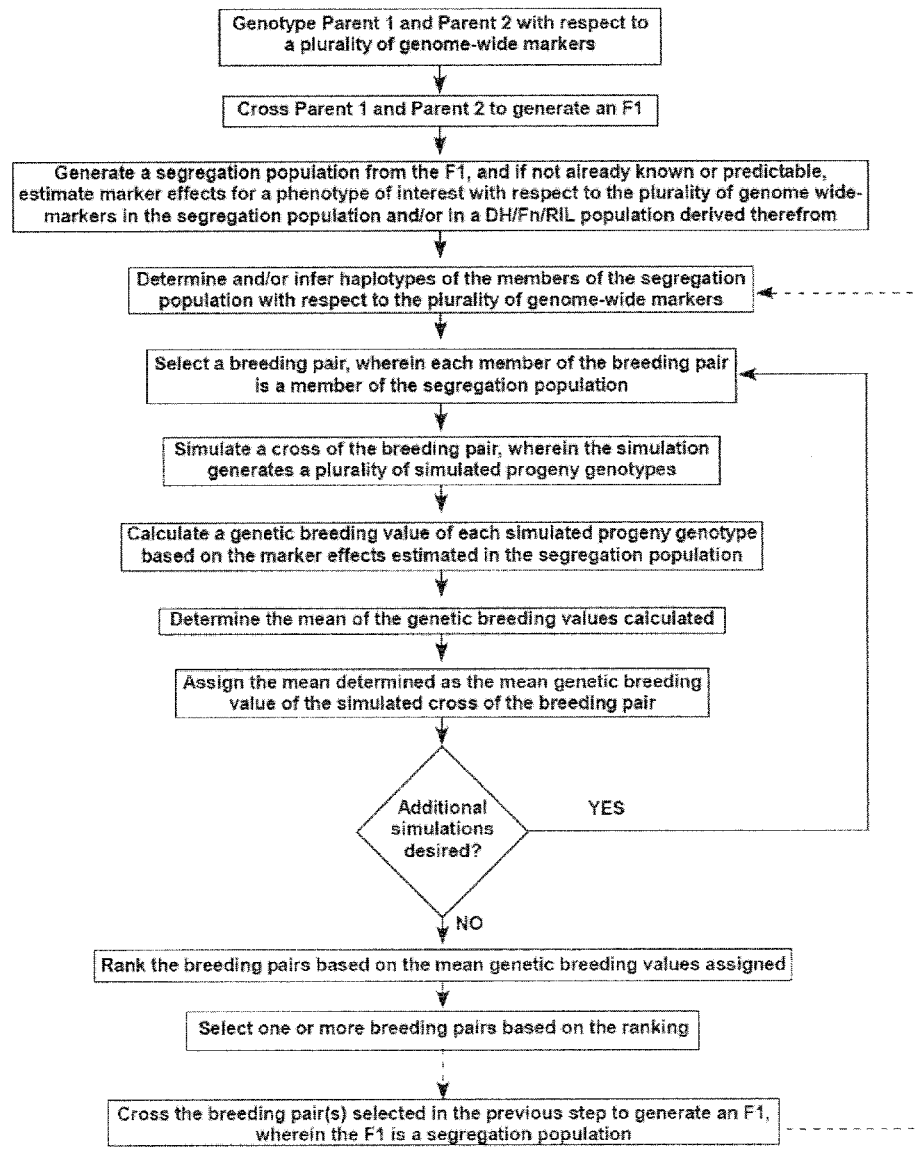

FIG. 3 is an exemplary scheme for employing GWS-SMART in plant breeding described in EXAMPLE 1.

Figure 4:
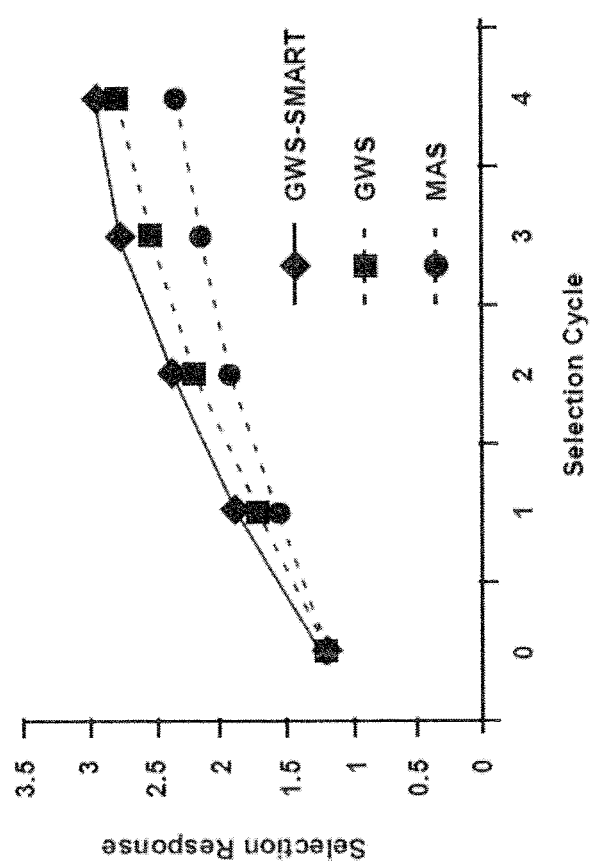

FIG. 4 is a comparison of exemplary genetic gains due to GWS-SMART, basic Genome-Wide Selection (GWS), and marker-assisted selection (MAS) described in EXAMPLE 1.

DETAILED DESCRIPTION

I. Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art.

Following long-standing patent law convention, the terms "a", "an", and "the" refer to "one or more" when used in this application, including the claims. For example, the phrase "a marker" refers to one or more markers. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100. Similarly, the term "plurality" refers to "at least two", and thus refers to, for example, 2, 3, 4, 5, 6, 7, 8, 9, 10, 15, 20, 25, 30, 35, 40, 45, 50, 75, 100, or more of that entity, including but not limited to whole number values between 1 and 100 or greater than 100.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration, or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods. Accordingly, unless indicated to the contrary, the numerical parameters set forth in this specification and attached claims are approximations that can vary depending upon the desired properties sought to be obtained by the presently disclosed subject matter.

As used herein, the term "allele" refers to a variant or an alternative sequence form at a genetic locus. In diploids, single alleles are inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the phrase "associated with" refers to a recognizable and/or assayable relationship between two entities. For example, the phrase "associated with a trait" refers to a locus, gene, allele, marker, phenotype, etc., or the expression thereof, the presence or absence of which can influence an extent, degree, and/or rate at which the trait is expressed in an individual or a plurality of individuals.

As used herein, the term "backcross", and grammatical variants thereof, refers to a process in which a breeder crosses a progeny individual back to one of its parents: for example, a first generation $F_1$ with one of the parental genotypes of the $F_1$ individual. In some embodiments, a backcross is performed iteratively, with a progeny individual of each successive backcross generation being itself backcrossed to the same parental genotype.

As used herein, the phrase "breeding population" refers to a collection of individuals from which potential breeding individuals and pairs are selected. In some embodiments, a breeding population is a segregation population.

As used herein, the term "chromosome" is used in its art-recognized meaning as a self-replicating genetic structure containing genomic DNA and bearing in its nucleotide sequence a linear array of genes.

As used herein, the terms "cultivar" and "variety" refer to a group of similar plants that by structural and/or genetic features and/or performance can be distinguished from other members of the same species.

As used herein, the phrase "elite line" refers to any line that is substantially homozygous and has resulted from breeding and selection for superior agronomic performance.

As used herein, the term "gene" refers to a hereditary unit including a sequence of DNA that occupies a specific location on a chromosome and that contains genetic instructions for a particular characteristic or trait in an organism.

As used herein, the phrase "genetic gain" refers to an amount of an increase in performance that is achieved through artificial genetic improvement programs. In some embodiments, "genetic gain" refers to an increase in performance that is achieved after one generation has passed (see Allard, 1960).

As used herein, the phrase "genetic map" refers to an ordered listing of loci usually related to the relative positions of the loci on a particular chromosome.

As used herein, the phrase "genetic marker" refers to a nucleic acid sequence (e.g., a polymorphic nucleic acid sequence) that has been identified as being associated with a trait, locus, and/or allele of interest and that is indicative of and/or that can be employed to ascertain the presence or absence of the trait, locus, and/or allele of interest in a cell or organism. Examples of genetic markers include, but are not limited to genes, DNA or RNA-derived sequences (e.g., chromosomal subsequences that are specific for particular sites on a given chromosome), promoters, any untranslated regions of a gene, microRNAs, short inhibitory RNAs (siRNAs; also called small inhibitory RNAs), quantitative trait loci (QTLs), transgenes, mRNAs, double-stranded RNAs, transcriptional profiles, and methylation patterns.

As used herein, the phrase "genome-wide selection" (GWS) refers to methods for increasing genetic gain in a species that employ markers located throughout the genome of the species to predict genomic breeding values (GBVs) of individuals. In contrast to methods such as marker-assisted selection (MAS), GWS is not based on the use of markers that have previously been identified as being linked to loci (e.g., QTLs) associated with any given trait of interest. Rather, each marker is generally considered as a putative QTL and all the markers are combined to predicting genomic breeding values (GBVs) of progeny with the GWS method.

As used herein, the term "genotype" refers to the genetic makeup of an organism. Expression of a genotype can give rise to an organism's phenotype (i.e., an organism's observable traits). A subject's genotype, when compared to a reference genotype or the genotype of one or more other subjects, can provide valuable information related to current or predictive phenotypes. The term "genotype" thus refers to the genetic component of a phenotype of interest, a plurality of phenotypes of interest, and/or an entire cell or organism. Genotypes can be indirectly characterized using markers and/or directly characterized by nucleic acid sequencing.

As used herein, the phrase "determining the genotype" of an individual refers to determining at least a portion of the genetic makeup of an individual and particularly can refer to determining genetic variability in an individual that can be used as an indicator or predictor of a corresponding phenotype. The genotype determined can be in some embodiments the entire genomic sequence of an individual, but generally far less sequence information is usually considered. The genotype determined can be as minimal as the determination of a single base pair, as in identifying one or more polymorphisms in the individual.

Further, determining a genotype can comprise determining one or more haplotypes. Still further, determining a genotype of an individual can comprise determining one or more polymorphisms exhibiting linkage disequilibrium to at least one polymorphism or haplotype having genotypic value. As used herein, the phrases "genotypic value", and "genomic breeding value" (GBV) refer to a measurable degree to which one or more haplotypes and/or genotypes affect the expression of a phenotype associated with a trait, and it can be considered as a contribution of the haplotype(s) and or genotype(s) to a trait. In some embodiments, the GBV can be calculated by regression of a phenotype on haplotypes.

In some embodiments, determining the genotype of an individual can comprise identifying at least one polymorphism of at least one gene and/or at one locus. In some embodiments, determining the genotype of an individual can comprise identifying at least one haplotype of at least one gene and/or at least one locus. In some embodiments, determining the genotype of an individual can comprise identifying at least one polymorphism unique to at least one haplotype of at least one gene and/or at least one locus.

As used herein, "haplotype" refers to the collective characteristic or characteristics of a number of closely linked loci within a particular gene or group of genes, which can be inherited as a unit. For example, in some embodiments, a haplotype can comprise a group of closely related polymorphisms (e.g., single nucleotide polymorphisms; SNPs). In some embodiments, a haplotype is a characterization of a plurality of loci on a single chromosome (or a region thereof) of a pair of homologous chromosomes, wherein the characterization is indicative of what loci and/or alleles are present on the single chromosome (or the region thereof).

As used herein, "linkage disequilibrium" (LD) refers to a derived statistical measure of the strength of the association or co-occurrence of two distinct genetic markers. Various statistical methods can be used to summarize LD between two markers but in practice only two, termed D' and r2, are widely used (see e.g., Devlin & Risch 1995; Jorde, 2000).

As such, the phrase "linkage disequilibrium" refers to a change from the expected relative frequency of gamete types in a population of many individuals in a single generation such that two or more loci act as genetically linked loci. If the frequency in a population of allele S is x, that of allele s is x', that of allele B is y, and that of allele b is y', then the expected frequency of genotype SB is xy, that of Sb is xy', that of sB is x'y, and that of sb is x'y', and any deviation from these frequencies in the population is an example of linkage disequilibrium.

As used herein, the term "heterozygous" refers to a genetic condition that exists in a cell or an organism when different alleles reside at corresponding loci on homologous chromosomes. As used herein, the term "homozygous" refers to a genetic condition existing when identical alleles reside at corresponding loci on homologous chromosomes. It is noted that both of these terms can refer to single nucleotide positions, multiple nucleotide positions (whether contiguous or not), and/or entire loci on homologous chromosomes.

As used herein, the term "hybrid", when used in the context of a plant, refers to a seed and the plant the seed develops into that result from crossing at least two genetically different plant parents.

As used herein, the term "hybrid", when used in the context of nucleic acids, refers to a double-stranded (or higher order) nucleic acid molecule (a "duplex") formed by hydrogen bonding between complementary nucleotide bases. The terms "hybridize" and "anneal" refer to the process by which single strands of nucleic acid sequences form double-helical (and higher ordered) segments through hydrogen bonding between complementary bases.

As used herein when used in the context of a plant, the terms "improved" and "superior", and grammatical variants thereof, refer to a plant (or a part, progeny, or tissue culture thereof) that as a consequence of having (or lacking) a particular allele of interest expresses a phenotype of interest or expresses a phenotype of interest to a greater or lesser degree (as desired) relative to another plant (or a part, progeny, or tissue culture thereof) that lacks (or has) the particular allele of interest.

As used herein, the term "inbred" refers to a substantially or completely homozygous individual or line. It is noted that the term can refer to individuals or lines that are substantially or completely homozygous throughout their entire genomes or that are substantially or completely homozygous with respect to subsequences of their genomes that are of particular interest.

As used herein, the term "introgress", and grammatical variants thereof (including, but not limited to "introgression", "introgressed", and "introgressing"), refer to both natural and artificial processes whereby one or more genomic regions of one individual are moved into the genome of another individual to create germplasm that has a new combination of genetic loci, haplotypes, and/or alleles. Exemplary methods for introgressing a trait of interest include, but are not limited to breeding an individual that has the trait of interest to an individual that does not, and backcrossing an individual that has the trait of interest to a recurrent parent.

As used herein, the term "isolated" refers to a nucleotide sequence (e.g., a genetic marker) that is free of sequences that normally flank one or both sides of the nucleotide sequence in a genome. As such, the phrase "isolated and purified genetic marker" can be, for example, a recombinant DNA molecule, provided one of the nucleic acid sequences normally found flanking the genetic marker in a naturally-occurring genome is removed or absent. Thus, isolated nucleic acids include, without limitation, a recombinant DNA that exists as a separate molecule (including but not limited to genomic DNA fragments produced by the polymerase chain reaction (PCR) or restriction endonuclease treatment) with less than the full complement of its naturally-occurring flanking sequences present, as well as a recombinant DNA that is incorporated into a vector, an autonomously replicating plasmid, and/or into the genomic DNA of an individual as part of a hybrid or fusion nucleic acid molecule.

As used herein, the term "linkage" refers to a phenomenon wherein alleles on the same chromosome tend to be transmitted together more often than would be expected by chance if their transmission were independent. Thus, two alleles on the same chromosome are said to be "linked" when they segregate from each other in the next generation in some embodiments less than 50% of the time, in some embodiments less than 25% of the time, in some embodiments less than 20% of the time, in some embodiments less than 15% of the time, in some embodiments less than 10% of the time, in some embodiments less than 9% of the time, in some embodiments less than 8% of the time, in some embodiments less than 7% of the time, in some embodiments less than 6% of the time, in some embodiments less than 5% of the time, in some embodiments less than 4% of the time, in some embodiments less than 3% of the time, in some embodiments less than 2% of the time, in some embodiments less than 1% of the time; in some embodiments less than 0.5% of the time, and in some embodiments less than 0.1% of the time.

As such, "linkage" typically implies and can also refer to physical proximity on a chromosome. Thus, two loci are linked if they are within in some embodiments 20 centiMorgans (cM), in some embodiments 15 cM, in some embodiments 12 cM, in some embodiments 10 cM, in some embodiments 9 cM, in some embodiments 8 cM, in some embodiments 7 cM, in some embodiments 6 cM, in some embodiments 5 cM, in some embodiments 4 cM, in some embodiments 3 cM, in some embodiments 2 cM, in some embodiments 1 cM of each other, in some embodiments 0.5 cM of each other, and in some embodiments 0.1 cM of each other. Similarly, a locus of the presently disclosed subject matter is linked to a marker (e.g., a genetic marker) if it is in some embodiments within 20, 15, 12, 10, 9, 8, 7, 6, 5, 4, 3, 2, 1, 0.5, or 0.1 cM of the marker.

As used herein, the phrase "linkage group" refers to all of the genes or genetic traits that are located on the same chromosome. Within a linkage group, those loci that are sufficiently close together physically can exhibit linkage in genetic crosses. Since the probability of a crossover occurring between two loci increases with the physical distance between the two loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous with the physical entity of a chromosome, although one of ordinary skill in the art will understand that a linkage group can also be defined as corresponding to a region (i.e., less than the entirety) of a given chromosome.

As used herein, the term "locus" refers to a position on a chromosome of a species, and which can encompass in some embodiments a single nucleotide, in some embodiments several nucleotides, and in some embodiments more than several nucleotides in a particular genomic region. In some embodiments, the terms "locus" and "gene" are used interchangeably.

As used herein, the terms "marker" and "molecular marker" are used interchangeably to refer to an identifiable position on a chromosome the inheritance of which can be monitored and/or a reagent that is used in methods for visualizing differences in nucleic acid sequences present at such identifiable positions on chromosomes. Thus, in some embodiments a marker comprises a known or detectable nucleic acid sequence. Examples of markers include, but are not limited to genetic markers, protein composition, peptide levels, protein levels, oil composition, oil levels, carbohydrate composition, carbohydrate levels, fatty acid composition, fatty acid levels, amino acid composition, amino acid levels, biopolymers, starch composition, starch levels, fermentable starch, fermentation yield, fermentation efficiency, energy yield, secondary compounds, metabolites, morphological characteristics, and agronomic characteristics. Molecular markers include, but are not limited to restriction fragment length polymorphisms (RFLPs), random amplified polymorphic DNA (RAPD), amplified fragment length polymorphisms (AFLPs), single strand conformation polymorphism (SSCPs), single nucleotide polymorphisms (SNPs), insertion/deletion mutations (indels), simple sequence repeats (SSRs), microsatellite repeats, sequence-characterized amplified regions (SCARs), cleaved amplified polymorphic sequence (CAPS) markers, and isozyme markers, microarray-based technologies, TAQMAN® markers, ILLUMINA® GOLDENGATE® Assay markers, nucleic acid sequences, or combinations of the markers described herein, which can be employed to define a specific genetic and/or chromosomal location.

In some embodiments, a marker corresponds to an amplification product generated by amplifying a nucleic acid with one or more oligonucleotides, for example, by the polymerase chain reaction (PCR). As used herein, the phrase "corresponds to an amplification product" in the context of a marker refers to a marker that has a nucleotide sequence that is the same as or the reverse complement of (allowing for mutations introduced by the amplification reaction itself and/or naturally occurring and/or artificial alleleic differences) an amplification product that is generated by amplifying a nucleic acid with a particular set of oligonucleotides. In some embodiments, the amplifying is by PCR, and the oligonucleotides are PCR primers that are designed to hybridize to opposite strands of a genomic DNA molecule in order to amplify a genomic DNA sequence present between the sequences to which the PCR primers hybridize in the genomic DNA. The amplified fragment that results from one or more rounds of amplification using such an arrangement of primers is a double stranded nucleic acid, one strand of which has a nucleotide sequence that comprises, in 5' to 3' order, the sequence of one of the primers, the sequence of the genomic DNA located between the primers, and the reverse-complement of the second primer. Typically, the "forward" primer is assigned to be the primer that has the same sequence as a subsequence of the (arbitrarily assigned) "top" strand of a double-stranded nucleic acid to be amplified, such that the "top" strand of the amplified fragment includes a nucleotide sequence that is, in 5' to 3' direction, equal to the sequence of the forward primer—the sequence located between the forward and reverse primers of the top strand of the genomic fragment—the reverse-complement of the reverse primer. Accordingly, a marker that "corresponds to" an amplified fragment is a marker that has the same sequence of one of the strands of the amplified fragment.

As used herein, the phrase "marker assay" refers to a method for detecting a polymorphism at a particular locus using a particular method such as but not limited to measurement of at least one phenotype (e.g., seed color, oil content, or a visually detectable trait such as corn and soybean grain yield, plant height, flowering time, lodging rate, disease resistance, aluminum tolerance, iron deficiency chlorosis tolerance, and grain moisture); nucleic acid-based assays including, but not limited to restriction fragment length polymorphism (RFLP), single base extension, electrophoresis, sequence alignment, allelic specific oligonucleotide hybridization (ASO), random amplified polymorphic DNA (RAPD), microarray-based technologies, TAQMAN® Assays, ILLUMINA®GOLDENGATE® Assay analysis, nucleic acid sequencing technologies; peptide and/or polypeptide analyses; or any other technique that can be employed to detect a polymorphism in an organism at a locus of interest.

As used herein, the phrase "native trait" refers to any existing monogenic or polygenic trait in a certain individual's germplasm. When identified through the use of molecular marker(s), the information obtained can be used for the improvement of germplasm through selective breeding of predicted populations as disclosed herein.

As used herein, the phrases "nucleotide sequence identity" refers to the presence of identical nucleotides at corresponding positions of two polynucleotides. Polynucleotides have "identical" sequences if the sequence of nucleotides in the two polynucleotides is the same when aligned for maximum correspondence. Sequence comparison between two or more polynucleotides is generally performed by comparing portions of the two sequences over a comparison window to identify and compare local regions of sequence similarity, The comparison window is generally from about 20 to 200 contiguous nucleotides. The "percentage of sequence identity" for polynucleotides, such as 50, 55, 60, 65, 70, 75, 80, 85, 90, 95, 98, 99 or 100 percent sequence identity, can be determined by comparing two optimally aligned sequences over a comparison window, wherein the portion of the polynucleotide sequence in the comparison window can include additions or deletions (i.e., gaps) as compared to the reference sequence for optimal alignment of the two sequences.

The percentage can be calculated by any method generally applicable in the field of molecular biology. In some embodiments, the percentage is calculated by: (a) determining the number of positions at which the identical nucleic acid base occurs in both sequences to the number of matched positions; (b) dividing the number of matched positions by the total number of positions in the window of comparison; and (c) multiplying the result by 100 to determine the percentage of sequence identity. Optimal alignment of sequences for comparison can also be conducted by computerized implementations of known algorithms, or by visual inspection. Readily available sequence comparison and multiple sequence alignment algorithms are, respectively, the Basic Local Alignment Search Tool (BLAST; Altschul et al., 1990; Altschul et al., 1997) and ClustalW programs (Larkin et al., 2007), both available on the internet. Other suitable programs include, but are not limited to, GAP, BestFit, Plot Similarity, and FASTA, which are part of the Accelrys GCG® Wisconsin Package available from Accelrys, Inc. of San Diego, Calif., United States of America. In some embodiments, a percentage of sequence identity refers to sequence identity over the full length of one of the sequences being compared. In some embodiments, a calculation to determine a percentage of sequence identity does not include in the calculation any nucleotide positions in which either of the compared nucleic acids includes an "n" (i.e., where any nucleotide could be present at that position).

The term "phenotype" refers to any observable property of an organism, produced by the interaction of the genotype of the organism and the environment. A phenotype can encompass variable expressivity and penetrance of the phenotype. Exemplary phenotypes include but are not limited to a visible phenotype, a physiological phenotype, a susceptibility phenotype, a cellular phenotype, a molecular phenotype, and combinations thereof.

As used herein, the phrase "phenotypic marker" refers to a marker that can be used to discriminate between different phenotypes.

As used herein, the term "plant" refers to an entire plant, its organs (i.e., leaves, stems, roots, flowers etc.), seeds, plant cells, and progeny of the same. The term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "polymorphism" refers to the presence of one or more variations of a nucleic acid sequence at a locus in a population of one or more individuals. The sequence variation can be a base or bases that are different, inserted, or deleted. Polymorphisms can be, for example, single nucleotide polymorphisms (SNPs), simple sequence repeats (SSRs), and Indels, which are insertions and deletions. Additionally, the variation can be in a transcriptional profile or a methylation pattern. The polymorphic sites of a nucleic acid sequence can be determined by comparing the nucleic acid sequences at one or more loci in two or more germplasm entries. As such, in some embodiments the term "polymorphism" refers to the occurrence of two or more genetically determined alternative variant sequences (i.e., alleles) in a population. A polymorphic marker is the locus at which divergence occurs. Exemplary markers have at least two (or in some embodiments more) alleles, each occurring at a frequency of greater than 1%. A polymorphic locus can be as small as one base pair (e.g., a single nucleotide polymorphism; SNP).

As used herein, the term "population" refers to a genetically heterogeneous collection of plants that in some embodiments share a common genetic derivation.

As used herein, the term "primer" refers to an oligonucleotide which is capable of annealing to a nucleic acid target (in some embodiments, annealing specifically to a nucleic acid target) allowing a DNA polymerase to attach, thereby serving as a point of initiation of DNA synthesis when placed under conditions in which synthesis of a primer extension product is induced (e.g., in the presence of nucleotides and an agent for polymerization such as DNA polymerase and at a suitable temperature and pH). In some embodiments, a plurality of primers is employed to amplify nucleic acids (e.g., using the polymerase chain reaction; PCR).

As used herein, the term "probe" refers to a nucleic acid (e.g., a single stranded nucleic acid or a strand of a double stranded or higher order nucleic acid, or a subsequence thereof) that can form a hydrogen-bonded duplex with a complementary sequence in a target nucleic acid sequence. Typically, a probe is of sufficient length to form a stable and sequence-specific duplex molecule with its complement, and as such can be employed in some embodiments to detect a sequence of interest present in a plurality of nucleic acids.

As used herein, the term "progeny" refers to any plant that results from a natural or assisted breeding of one or more plants. For example, progeny plants can be generated by crossing two plants (including, but not limited to crossing two unrelated plants, backcrossing a plant to a parental plant, intercrossing two plants, etc.), but can also be generated by selfing a plant, creating a double haploid, or other techniques that would be known to one of ordinary skill in the art. As such, a "progeny plant" can be any plant resulting as progeny from a vegetative or sexual reproduction from one or more parent plants or descendants thereof. For instance, a progeny plant can be obtained by cloning or selfing of a parent plant or by crossing two parental plants and include selfings as well as the $F_1$ or $F_2$ or still further generations. An $F_1$ is a first-generation progeny produced from parents at least one of which is used for the first time as donor of a trait, while progeny of second generation ($F_2$) or subsequent generations ($F_3$, $F_4$, and the like) are in some embodiments specimens produced from selfings (including, but not limited to double haploidization), intercrosses, backcrosses, or other crosses of $F_1$ individuals, $F_2$ individuals, and the like. An $F_1$ can thus be (and in some embodiments, is) a hybrid resulting from a cross between two true breeding parents (i.e., parents that are true-breeding are each homozygous for a trait of interest or an allele thereof, and in some embodiments, are inbred), while an $F_2$ can be (and in some embodiments, is) a progeny resulting from self-pollination of the $F_1$ hybrids.

As used herein, the phrase "quantitative trait locus" (QTL; quantitative trait loci—QTLs) refers to a genetic locus or loci that control to some degree a numerically representable trait that, in some embodiments, is continuously distributed. When a QTL can be indicated by multiple markers, the genetic distance between the end-point markers is indicative of the size of the QTL.

As used herein, the phrase "recombination" refers to an exchange of DNA fragments between two DNA molecules or chromatids of paired chromosomes (a "crossover") over in a region of similar or identical nucleotide sequences. A "recombination event" is herein understood to refer to a meiotic crossover.

As used herein, the phrases "selected allele", "desired allele", and "allele of interest" are used interchangeably to refer to a nucleic acid sequence that includes a polymorphic allele associated with a desired trait. It is noted that a "selected allele", "desired allele", and/or "allele of interest" can be associated with either an increase in a desired trait or a decrease in a desired trait, depending on the nature of the phenotype sought to be generated in an introgressed plant.

As used herein, the phrase "significant QTL markers" refers to QTL markers that are characterized by a test statistic LOD that is greater than an empirical LOD threshold estimated from 5000 permutations (see Churchill & Doerge, 1994).

As used herein, the phrase "single nucleotide polymorphism", or "SNP", refers to a polymorphism that constitutes a single base pair difference between two nucleotide sequences. As used herein, the term "SNP" also refers to differences between two nucleotide sequences that result from simple alterations of one sequence in view of the other that occurs at a single site in the sequence. For example, the term "SNP" is intended to refer not just to sequences that differ in a single nucleotide as a result of a nucleic acid substitution in one as compared to the other, but is also intended to refer to sequences that differ in 1, 2, 3, or more nucleotides as a result of a deletion of 1, 2, 3, or more nucleotides at a single site in one of the sequences as compared to the other. It would be understood that in the case of two sequences that differ from each other only by virtue of a deletion of 1, 2, 3, or more nucleotides at a single site in one of the sequences as compared to the other, this same scenario can be considered an addition of 1, 2, 3, or more nucleotides at a single site in one of the sequences as compared to the other, depending on which of the two sequences is considered the reference sequence. Single site insertions and/or deletions are thus also considered to be encompassed by the term "SNP".

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances.

Longer sequences typically hybridize specifically at higher temperatures. An extensive guide to the hybridization of nucleic acids is found in Tijssen, 1993. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Exemplary stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions can also be achieved with the addition of destabilizing agents such as formamide. Additional exemplary stringent hybridization conditions include 50% formamide, 5×SSC, and 1% SDS incubating at 42° C.; or SSC, 1% SDS, incubating at 65° C.; with one or more washes in 0.2× SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al., 1999).

As used herein, the phrase "TAQMAN® Assay" refers to real-time sequence detection using PCR based on the TAQMAN® Assay sold by Applied Biosystems, Inc. of Foster City, Calif., United States of America. For an identified marker a TAQMAN® Assay can be developed for the application in the breeding program.

As used herein, the term "tester" refers to a line used in a testcross with one or more other lines wherein the tester and the line(s) tested are genetically dissimilar. A tester can be an isogenic line to the crossed line.

As used herein, the terms "trait" and "trait of interest" refer to a phenotype of interest, a gene that contributes to a phenotype of interest, as well as a nucleic acid sequence associated with a gene that contributes to a phenotype of interest. Any trait that would be desirable to screen for or against in subsequent generations can be a trait of interest. Exemplary, non-limiting traits of interest include yield, disease resistance, agronomic traits, abiotic traits, kernal composition (including, but not limited to protein, oil, and/or starch composition), insect resistance, fertility, silage, and morphological traits. In some embodiments, two or more traits of interest are screened for and/or against (either individually or collectively) in progeny individuals.

As used herein, the term "transgene" refers to a nucleic acid molecule introduced into an organism or its ancestors by some form of artificial transfer technique. The artificial transfer technique thus creates a "transgenic organism" or a "transgenic cell". It is understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breedings result in the artificially transferred nucleic acid molecule being present in the progeny individual.

II. Methods for Increasing Genetic Gain

In some embodiments, the presently disclosed subject matter provides methods for increasing genetic gain. An exemplary embodiment of the presently disclosed methods is termed Genome-Wide Selection—Simulated Marker-Assisted Recurrent Testing of progeny (GWS-SMART). It combines computer simulations and GWS to improve genetic gains in breeding programs. In some embodiments, GWS-SMART simulates progeny generated from some or all possible crosses of the lines present in a breeding population, identifying those crosses with acceptably high likelihoods of producing superior progeny, and choosing the appropriate individuals with whom to move forward (see FIG. 1 and FIG. 3).

As such, provided herein in some embodiments are methods for increasing genetic gain by using computer simulations in plant breeding. With GWS-SMART, it is possible to simulate progeny from some or all possible crosses of a breeding population. Thereafter, breeding pairs are selected for which simulated crosses are predicted resulting in acceptably high likelihoods of producing superior progeny.

Thus, in some embodiments, the presently disclosed methods comprise (a) providing effects with respect to a trait of interest of a plurality of genome-wide markers in a breeding population comprising a plurality of potential breeding partners; (b) selecting from the breeding population a first breeding pair comprising a first breeding partner and a second breeding partner, wherein crossing the first breeding partner and the second breeding partner would produce a subsequent population; (c) inferring or determining haplotypes with respect to the plurality of genome-wide markers for the first breeding partner and the second breeding partner based on genotypes of markers of these partners and a given genetic map; (d) simulating a cross between the first breeding partner and the second breeding partner to produce a progeny generation, each member of the progeny generation comprising a simulated genotype; (e) calculating a genetic potential value of the progeny generation, wherein the genetic potential value of the progeny generation is the mean of the genomic breeding value of each simulated genotype of each member of the progeny generation; Or calculating a distribution or a frequency of occurrence for one or more of the genotypes of one or more members of the progeny generation; (f) repeating steps (b)-(e) one or more times, wherein in each iteration of step (b), the selecting comprises selecting a different first breeding partner, a different second breeding partner, or both from the breeding population; (g) ranking each simulated cross of step (d) based on the genetic potential value calculated in step (e); and (h) selecting one or more optimal breeding pairs based on the ranking of step (g), wherein crossing the breeding pair selected in step (g) is predicted to generate progeny with increased genetic gain. An exemplary implementation of GWS-SMART is depicted in FIG. 3.

II.A. Providing or Estimating Effects

The presently disclosed subject matter includes in some embodiments the step of providing or estimating effects (also referred to as "phenotypic effects" and/or "marker effects") with respect to a trait of interest of a plurality of genome-wide markers in a breeding population comprising a plurality of potential breeding partners. Effects with respect to a trait of interest of a plurality of genome-wide markers can be known (e.g., previously estimated, and hence provided to the methods of the presently disclosed subject matter) or can be estimated de novo.

In order to estimate effects, the breeding population acts as a reference population. As used herein, the phrase "reference population" refers to a population of individuals (e.g., plants) for which genotype and phenotype information is available (e.g., known, discernable, or inferable) with respect to genome-wide markers and a trait of interest. In some embodiments, the members of reference populations can be genotyped with respect to a plurality of genome-wide markers. Observation of the genotyped members of the reference population with respect to phenotype of the trait of interest (referred to herein as "phenotyping") facilitates the determination of the effects of the presence or absence of each of the plurality of genetic markers that are associated with the trait of interest (referred to herein as "effects", "phenotypic effects", and/or "marker effects").

In some embodiments, the reference population provided includes members whose genomes collectively and/or individually include all of the genome-wide markers for which effects are to be estimated. In some embodiments, the reference is a biparental segregation population, for instance, a double haploid (DH) population, a recombinant inbred line (RIL) population, an $F_n$ population (i.e., a population that has gone through n=2, 3, 4, 5, 6, or more generations of inbreeding or selfing), or a combination thereof (collectively referred to herein as a "DH/$F_n$/RIL" population). In some embodiments, a Dh/$F_n$/RIL population is itself generated from an $F_1$ population that resulted from a cross of two parents (in some embodiments, wherein one or both of the parents are inbred). In some embodiments, the members of the DH/$F_n$/RIL population are inbred or substantially inbred, such that each member of the population is homozygous at substantially all or all loci. An advantage of using such a population is that it can facilitate the ability to infer haplotype structures or linkage phases by genotyping the members with respect to each genome-wide marker. For example, a DH or RIL individual will have one of two possible homozygous genotypes at each locus: QQ or qq. For an $F_2$, $F_3$, $F_4$, or later generation population, two exemplary methods for inferring haplotypes of the members of the $F_n$ population are provided herein below.

By way of example and not limitation, suppose that genotypic and phenotypic data for a trait of interest are collected from a reference population that collectively has been grown in multiple locations with one or multiple replicates within each location. Given the genotypic and phenotypic data, the effect of each marker can be estimated using any of several possible strategies including, but not limited to least-squares estimation, best linear unbiased prediction (BLUP) and derivatives thereof (e.g., genomic BLUP or GBLUP), or one of the Bayesian estimation methods (e.g., BayesA and BayesB; see Meuwissen et al., 2001 for a discussion of these approaches).

In some embodiments, the GBLUP method is employed for estimating marker effects. An advantage of using the GBLUP method is the ability to include considerations of genetic variance, which is a sum of the genetic variations of all of the loci associated with a given trait of interest, and also environmental variance, which can be related to many environmental factors including, but not limited to differences in soil, temperature, water, fertilizer, etc. In some embodiments, these variance components can be calculated using restricted maximum likelihood estimation (REML; Henderson, 1975; see e.g., Harville, 1977) based on phenotypic data from multiple locations using the model of Equation (1):

$$y_{ij} = \mu + G_i g_i + L_j b_j + e_{ij} \quad (1)$$

where $y_{ij}$ is the phenotype of the line i at the location j (which is an observable characteristic of a trait of interest); $\mu$ is the overall mean of the phenotype of a trait; $G_i$ is the indicator variable representing the genotype of the line i; $g_i$ is the genotypic effect of the line i, which can be considered as a sum of QTL effects; $L_j$ is the indicator variable, with 1 indicating that the line has been phenotyped at the location j and 0 indicating that the line has not been phenotyped at the location; $b_j$ is the effect of the location j caused by the difference of water, soil, temperature, and/or other factors; and $e_{ij}$ is the residual of phenotype for the line i at the location j following $e_{ij} \sim N(0, \sigma_e^2)$. Here, it is assumed that $g_i$ is considered as a random effect following $g_i \sim N(0, \sigma_g^2)$, and $b_j$ is a fixed effect. The genetic variance $\sigma_g^2$ and environmental variance $\sigma_e^2$ can be estimated by REML (Henderson, 1975). In the model, the parameter $g_i$ can be calculated by a BLUP procedure (see e.g., Henderson, 1975), and the BLUPs of each line are employed as phenotypes in the following model.

The effect of each marker can be estimated based on the phenotypic BLUPs and marker genotypic data from a training population using genome-wide best linear unbiased prediction (GBLUP; Meuwissen et al., 2001). An exemplary linear model for GBLUP is:

$$y_i = \mu + \sum_{j=1}^{m}(z_{ij} g_j) + e_i \quad (2)$$

where $y_i$ is the phenotypic BLUP of line i, $\mu$ is the overall mean, $z_{ij}$ is the genotype of the marker j for line i, $g_i$ is the effect of marker j, and $e_i$ the residual following $e_i \sim N(0, \sigma_e^2)$. In some embodiments, the phenotype BLUP can be considered as the average of phenotypes of a line across multiple locations. Since in these embodiments a mixed model has been employed to calculate this quantity, it can be referred to as a phenotype BLUP in the context of mixed model theory (Henderson, 1975). In the model, μ is assumed to be a fixed effect and $g_i$ is assumed to be a random effect following a normal distribution $g_i \sim N(0, \sigma_{gj}^2)$. Each marker is also assumed to have an equal genetic variance expressed by Equation (2a):

$$\sigma_{gj}^2 = \sigma_g^2/m \tag{2a}$$

with m the total number of markers used (Meuwissen et al., 2001; Bernardo & Yu, 2007; Lorenzana & Bernardo 2009; Jannink et al., 2010). Based on the model, the variance-covariance matrix V for the phenotype y is expressed by Equation (2b):

$$V = \sum_{j=1}^{m} (Z_j Z_j^T \sigma_{gj}^2) + I_{(n \times n)} \sigma_e^2 \tag{2b}$$

where $Z_j$ is a vector of genotypic scores of marker j across n individuals in a population and $I_{(n \times n)}$ is an identity matrix with diagonal elements 1 and others 0. The overall mean μ, a fixed effect, can be estimated as set forth in Equation (2c):

$$\hat{\mu} = (X^T V^{-1} X)^{-1} X^T V^{-1} y \tag{2c}$$

with X a vector of ones, and the effect of marker j can be calculated as set forth in Equation (2d):

$$\hat{g}_j = \sigma_{gj}^2 Z_j^T V^{-1} (y - X\hat{\mu}) \tag{2d}.$$

In some embodiments, one or more of Equations (1), (2), (2a), (2b), (2c), and (2d) are calculated by a suitably-programmed computer.

II.B. Haplotype Inference

The members of the breeding/reference population serve as potential breeding partners, and crosses among the various potential breeding partners are simulated to determine which of the breeding partners are most likely to generate progeny with desirable genotypes and hence, desirable phenotypes. Thus, putative progeny can be simulated from crosses between members of the breeding population. In some embodiments, a breeding population has n members, and all possible crosses among the members of the breeding population (i.e., a total of n(n−1)/2 total crosses) are simulated.

In order to simulate any given cross, the haplotypes with respect to the genome-wide markers that are located on each chromosome must be inferred. In some embodiments, the inference of haplotypes is based on the genotypes of the members of the breeding population taking into account the genetic distances between each two adjacent markers.

As discussed hereinabove, inferring haplotypes of markers of DH or RIL individuals is relatively straightforward. By way of example and not limitation, if the genotypes of two individuals with respect to ten (10) SNP markers on a given chromosome are depicted as AABBABBAAB and BBAAAABAAA, where A represents a homozygous genotype with two identical alleles "0" from one parent of a particular DH or RIL individual and B represents the genotype with two identical alleles "1" from the other parent, then the haplotype structures for the two individuals can be depicted as:

```
0 0 1   1 0 1   1 0 0 1
┼─┼─┼   ┼─┼     ┼─┼─┼─┼
0 0 1   1 0 1   1 0 0 1
1 1 0   0 0 0   1 0 0 0
┼─┼─┼   ┼─┼─┼   ┼─┼─┼─┼
1 1 0   0 0 0   1 0 0 0,
``` respectively.

Inferring haplotypes of markers in individuals of $F_n$-type populations is more complex, however. Two algorithms were developed to address the issue. In the first algorithm, the haplotype structure is inferred based on the minimum recombination principle (MRP). The MRP stands for the proposition that genetic recombination is rare and thus haplotypes with fewer recombinants should be preferred in haplotype reconstruction (O'Connell, 2000; Gusfield, 2002; Qian & Beckmann, 2002).

By way of further example and not limitation, suppose the genotype AHBBAHHHHB is observed in an $F_n$-type individual, in which A is a homozygous genotype with two identical alleles "0" from one parent (in some embodiments, the "parent" is several generations removed if n>1), B is a homozygous genotype with two identical alleles "1" from the other parent, and H is heterozygous genotype (i.e., a genotype with both alleles 0 and 1). In the instant example, there is only one H between the first and fifth markers, and thus the haplotype of the individual with respect to these five markers can be expressed as:

```
0 0 1   1 0
┼─┼─┼   ┼─┼
0 1 1   1 0.
```

Looking now to the sixth marker, the individual is heterozygous with respect to this marker as well. The result is that there would be two haplotypes that are possible, which can be depicted as follows:

```
0 0 1   1 0 0       0 0 1   1 0 1
┼─┼─┼   ┼─┼─┼       ┼─┼─┼   ┼─┼─┼
0 1 1   1 0 1  and  0 1 1   1 0 0.
```

For either haplotype structure, the number of recombination events that would generate the haplotype structure is five, since a complete lack of recombination would have resulted in chromosome regions with either all 0's or all 1's but no chromosome regions with both 0's and 1's. Thus, to generate the upper haplotype of the top structure, a recombination event between the second and third markers would create the switch from 0 to 1 and between the fourth and fifth would create the switch from 1 back to 0. With respect to the lower haplotype of the top structure, a recombination event between the first and second markers would create the switch from 0 to 1, a recombination event between the fourth and fifth markers would create the switch from 1 back to 0, and a recombination event between the fifth and sixth markers would create the switch back to 1 (i.e., five total for the top haplotype structure). A similar analysis of the bottom haplotype structure reveals that it would be produced by recombination events between the second and third markers, the fourth and fifth markers, and the fifth and sixth markers on the upper haplotype and between the first and second and the fourth and fifth on the lower haplotype.

However, since the individual is homozygous at markers 1, 3, 4, and 5, recombination events that occur between markers 3 and 5 would be undetectable when genotypes alone are considered. As a consequence, the haplotype structures of these individuals can be simplified based on the heterozygous genotypes of the second and sixth markers as follows:

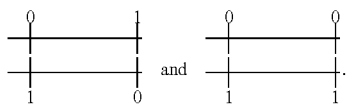

For the upper haplotype structure, the number of recombination events is two (i.e., one recombination event between allele 0 and 1 on the top chromosome and one recombination event between allele 1 and 0 on another chromosome), and the number of recombination events is 0 for the lower haplotype structure (chromosome has only alleles from the second parent).

Therefore, applying the basic proposition of MRP, the second haplotype structure (i.e., the one that shows less recombination) is the one with which the analysis is continued. As a result, the haplotype structure from the first to sixth markers can be depicted as:

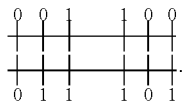

By applying the same strategies to the remaining markers, it is possible to reconstruct the haplotype structure of the entire chromosome region. As a result, the haplotype structure of all ten markers can be depicted as:

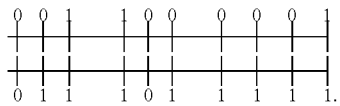

A second exemplary method for inferring haplotypes is based on the determined genotypes of pedigreed (i.e., genotyped) lines. This method is a chained inference in the sense that it first infers the linkage phase of the first two markers (the first and second markers), and then estimates the linkage phase between the second and third markers. This process is repeated until the last marker on the same chromosome is considered.

By way of example and not limitation, consider an $F_4$ breeding population. Cycle 0 genotypes would be known as the members of this population would be genotyped. Genotypic data from cycle 1 would also be available after one cycle of selection using the presently disclosed methods is executed. Starting with the first and second markers, since haplotype information can be easily inferred from homozygous genotypes, consider the case where individual 1 from cycle 0 is AA, and individual 2 is HH. It is also possible to use the segregation of their progeny to infer the haplotype of individual 2. Since genotype data are determined at each cycle, it is possible to reconstruct the haplotype structure of an individual based on its genotype in combination with its offsprings' genotypes. If genotype data from cycle 1 is not available, MRP is employed to infer it from its own genotype as set forth above. The ability to employ progeny genotypes increases the accuracy of the inference, however.

To do this, the genotypic segregation of the progeny individuals in cycle 1 from two parental individuals is analyzed. In cycle 1, the frequency of each of four types of gametes (i.e., 00, 11, 01, and 10 of a cross of AA and HH) can be calculated. If the gamete with the highest observed frequency is 00 or 11, then the haplotypes for individual 2 are:

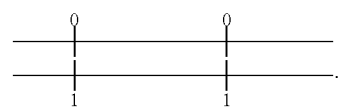

Otherwise, the haplotype is

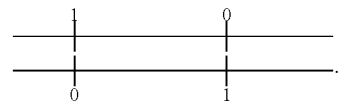

After the haplotypes for the first and second marker are resolved, the same approach can be employed for inferring the haplotypes of the remaining markers.

In some embodiments, one or more haplotype inferences are performed using a suitably-programmed computer.

II.C. Selecting Breeding Pairs and Simulating Crosses Thereof

After the haplotypes of each individual are inferred, crosses between pairs of individuals can be simulated to produce putative (i.e., simulated) progeny. In some embodiments, all possible crosses are simulated, such that in a breeding population of n individuals, n(n−1)/2 crosses are simulated. For each cross, a plurality of progeny is simulated using basic meiosis theory. Using larger numbers of simulated progeny per cross can help ensure there are a sufficient number of different genotypes generated in each simulation to differentiate between crosses wherein the parents from which the breeding population is derived are very similar genetically. In some embodiments, at least 50, 100, 250, 500, or 1000 progeny genotypes are simulated per cross.

An exemplary approach to simulating the genotype of a progeny from the haplotypes of its two parental lines is as follows. First, a gamete and/or haplotype is generated from each parent by the meiosis process. Suppose the haplotype structure with respect to a given chromosome (e.g., chromosome A) of one parent is:

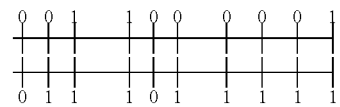

and the genetic linkage map of said chromosome in the relevant region is:

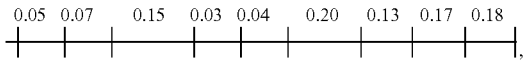

wherein each numerical value shown in the inter-marker regions corresponds to a recombination frequency that has been determined for that region.

A particular chromosome (each haplotype above corresponding to one chromosome of a chromosome pair) is then selected to start with 0.50 of probability, since, in meiosis, each of homologous chromosomes has an equal opportunity to form a gamete with another chromosome from a different homologous pair. For example, the top chromosome can be selected. The haplotype at the first locus of this chromosome is 0. The allele at the second locus is then simulated as follows. The genetic linkage map depicted above indicates that a recombination event would be expected in the marker 1-marker 2 interval in about 5% of (simulated) meioses. A random number is then generated from a uniform distribution of [0, 1], and if the random number generated is less than 0.05, the simulation incorporates a recombination event between those two loci. Otherwise, no any recombination event is incorporated. If no recombination event is simulated between the first and second markers, allele 0 at the second marker is simulated to transfer together with the allele 0 at the first maker to the next generation. The resulting haplotype with respect to first locus and the second locus is thus depicted as:

0 0
├─┼─────────────────, and the simulation continues with respect to the top chromosome.

If, however, the random number drawn with respect to the first and second markers is greater than 0.05, the focus is switched to the bottom chromosome (since the genetic material on the bottom chromosome beginning at the second marker is considered to have been exchanged into the top chromosome as a result of the recombination event between the first and second markers). This simulation approach is continued until the last locus (in this example, the tenth locus) is considered. An exemplary haplotype (which can also be considered an exemplary gamete) so obtained can be depicted as:

This haplotype/gamete is then simulated to combine with a gamete simulated to be derived from the other parent. Such a simulated game could be depicted as:

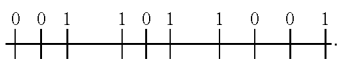

The combination of these two simulated gametes results in a simulated progeny with the following haplotype structure on the two corresponding homologous chromosomes, which can be depicted as:

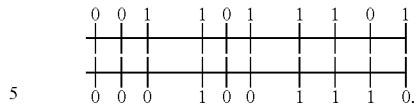

The genotype from this haplotype can be translated as AAH-BAHBBHH, where the genotype at each locus is defined as A if two alleles are 0s, B if two alleles are 1s, and H if two alleles are 0 and 1. For convenience in subsequent calculations, the three types of genotype A, B, and H can be encoded as −1, +1, and 0. These codes (also referred to herein as "scores") can be employed for the calculation of marker effects and GBV in the practice of the presently disclosed subject matter as described in more detail herein.

In some embodiments, one or more of the simulations are performed by a suitably-programmed computer.

II.D. Calculating Genetic Potential Value (GPV) based on Simulated Progeny Genotypes Once haplotypes are determined and/or inferred, genomic breeding values (GBVs) of the individuals with such haplotypes can be calculated from the corresponding genotypes. In order to calculate GBVs from simulated progeny genotypes, Equation (5) can be employed:

$$\hat{y}_i = \hat{\mu} + \sum_{j=1}^{m} (z_{ij}\hat{g}_j) \quad (5)$$

where $\hat{g}_j$ is the effect estimated using Equation (2b) from a reference population and $z_{ij}$ is the genotype of marker j of individual i. It can be seen that the GBV of a simulated progeny individual can be calculated by summing effects of each marker present in the simulated progeny individual. It can also be seen that this prediction model is an additive model that corresponds to the additive model used for estimating marker effects in the training population. Specifically, $x_i$ is defined as −1 if the genotype is A; 0 if the genotype is H, and 1 if the genotype is B (assuming that the A, B, and H symbol system described hereinabove is employed for genotyping of each marker).

Each cross (and hence, each breeding pair) can thus be evaluated by looking at the progeny that are simulated. In some embodiments, the mean of all GBVs calculated for the simulated progeny of a cross can be employed as a measure of the GPV of the cross.

In some embodiments, however, it is recognized that the mean might not reflect the total genetic variation in the simulated progeny of any given cross, and thus might not be optimal for measuring the genetic potential of obtaining a progeny with many favorable alleles due to recombination. For this reason, in some embodiments only those progeny from any given simulated cross that have GBVs that fall outside of one standard deviation of the mean of all GBVs from the all simulated progeny of the simulated cross are employed as the GPV of the cross. If the family (i.e., the collection of simulated progeny from any particular breeding pair) has large genetic variance, a high GPV is expected. Otherwise, the mean should be small. This criterion can result in the selection of a family with both a high mean and high genetic variation, which in some embodiments can be desirable. In some embodiments, the presently disclosed methods evaluate the distribution or frequency of GBVs of all the progeny in a population in order to identify those lines that fall in the right tail area of the distribution.

The above discussion relates to employing the presently disclosed methods to select breeding pairs with respect to a single phenotype of interest. In some embodiments, however, the presently disclosed methods can be employed to select breeding pairs with respect to multiple phenotypes of interest. In some embodiments, multi-trait GBV (MT-GBV) can be employed as a measure of the genetic merits of multiple traits. An exemplary approach to calculating MT-GBV is as follows:

$$MT - GBV_k = \sum_{i=1}^{t} \left( w_i \frac{GBV_{ki} - \text{Min}(GBV_k)}{\text{Max}(GBV_k) - \text{Min}(GBV_k)} \right) \quad (6a)$$

or $$MT - GBV_k = \sum_{i=1}^{t} \left( w_i \frac{GBV_{ki} - \text{Min}(GBV_k)}{Std(GBV_k)} \right) \quad (6b)$$

where $MT\text{-}GBV_k$ denotes the multi-trait genomic estimated breeding value of line k; $w_i$; =1, 2, 3, . . . , t with t the number of traits considered) is the weight (relative importance) of the trait i, which can be pre-determined as desired (including, but not limited to by breeders based on their breeding goals and experience); $GBV_{ki}$ is the genomic estimated breeding value of line k for trait i; $\text{Min}(GBV_k)$ is the minimum value of GBV for trait k, $\text{Max}(GBV_k)$ is the maximum value of GBV for trait k; $\text{Mean}(GBV_k)$ is the mean of GBV for trait k, and Std $(GBV_k)$ the standard deviation of GBVs for trait k. In some embodiments, two techniques are employed for each equation to normalize GBV of each trait to avoid the influence of scale of different traits on the selection.

In some embodiments, one or more of Equations (5), (6a), and (6b) are performed by a suitably-programmed computer.

II.E. Ranking the Crosses Based on GPVs

After GPVs of each cross are calculated, the crosses can be ranked based on GPVs. In some embodiments, the top ranked crosses can be selected and actually crossed to produce a subsequent generation. The next generation can thereafter be considered a new $F_1$ and re-analyzed using the methods described herein and depicted in FIG. 4.

It is noted that it is possible that some lines in the breeding population could be employed more often than others in the production of the new $F_1$ generations. A potential disadvantage of this with respect to long term selection (i.e., cycling through the presently disclosed methods several times) could be the decay of heterozygosity due to a limited number of lines used for crossing.

To address this issue, a second approach can be employed. With respect to this second approach, after the top breeding pairs are identified from the ranking of GPVs, the crosses with the highest rank can be enhanced by looking to other highly ranked lines in order to add an additional line that is not part of the highest rank. This process can be repeated until a minimum number of genetically different lines is employed.

As such, trait improvement can be continued by repeating the methods iteratively, with the breeding pairs identified in one cycle being used to generate the breeding population(s) (in some embodiments, segregation populations) of the next cycle. The haplotype structures of the individuals from the first to the last cycle of selection can be traced, since the haplotypes are employed to perform the simulations at each cycle. After multiple cycles, the final progeny population can be tested and evaluated across multiple locations, and the lines with acceptable performances can be promoted to a next stage of breeding and/or can be employed as a new variety, as desired.

III. Methods for Choosing Breeding Pairs Predicted to Produce Progeny having Desired Phenotypes and/or Genotypes and Methods for Producing the Same The presently disclosed subject matter also provides methods for choosing breeding pairs predicted to produce progeny having desired phenotypes and/or genotypes. In some embodiments, the methods comprise (a) estimating or providing effects with respect to trait(s) of interest of a plurality of genome-wide markers in breeding populations in some embodiments, biparental breeding populations) comprising a plurality of potential breeding partners; (b) selecting breeding partners from the breeding populations, wherein the haplotypes of each of the breeding partners are known or are predictable with respect to the plurality of genetic markers; (c) inferring and/or determining haplotypes with respect to the plurality of genome-wide markers for the breeding partners; (d) simulating crosses between the breeding partners to produce progeny generations, each member of the progeny generations comprising a simulated genotype; (e) calculating a genetic potential value of the progeny generations, wherein the genetic potential values are the means of the genomic breeding value of each simulated genotype of each member of the progeny generations; (f) repeating steps (b)-(e) one or more times, wherein in each iteration of step (b), the selecting comprises selecting a different first breeding partner, a different second breeding partner, or both from the breeding population; (g) ranking each simulated cross of step (d) based on the genetic potential values calculated in step (e); and (h) selecting one or more breeding pairs based on the ranking of step (g), wherein the breeding pairs are predicted to produce progeny with the desired phenotypes and/or genotypes.

In some embodiments, it can be desirable to produce the progeny with the desired phenotypes and/or genotypes. In such embodiments, the methods can further comprise (i) breeding the one or more breeding pairs selected in step (h) to generate progeny individuals having the desired phenotypes and/or genotypes.

IV. Methods for Increasing the Likelihood of Producing Progeny Having Desired Phenotypes and/or Genotypes The presently disclosed subject matter also provides methods for increasing the likelihood of Producing Progeny having desired Phenotypes. In some embodiments, the methods comprise (a) providing effects with respect to traits of interest of a plurality of genome-wide markers in breeding populations comprising pluralities of potential breeding partners; (b) selecting from the breeding populations breeding pairs comprising first and second breeding partners, wherein crossing the first and second breeding partners would produce a segregating progeny population; (c) inferring haplotypes with respect to the plurality of genome-wide markers for the first and second breeding partners; (d) simulating crosses between the first and second breeding partners to produce progeny generations, each member of the progeny generations comprising a simulated genotype; (e) calculating genetic potential values of the progeny generations, wherein the genetic potential values of the progeny generations are the means of the genomic breeding values of each simulated genotype of each member of the progeny generations; (f) repeating steps (b)-(e) one or more times, wherein in each iteration of step (b), the selecting comprises selecting a different first breeding partner, a different second breeding partner, or both from the breeding population; (g) ranking each simulated cross of step (d) based on the genetic potential value calculated in step (e); and (h) selecting one or more breeding pairs based on the ranking of step (g), wherein each of the one or more breeding pairs is predicted to have an increased likelihood of producing a progeny having the desired phenotype versus other breeding pairs in the breeding population.

V. Progeny, and Cells, Seeds, and Tissue Cultures Derived Therefrom

The presently disclosed subject matter also provides progeny individuals generated by the methods disclosed herein. In some embodiments, the progeny individuals are plants. Exemplary plants include, but are not limited to maize, wheat, barley, rice, sugar beet, sunflower, winter oilseed rape, canola, tomato, pepper, melon, watermelon, broccoli, cauliflower, Brussel sprouts, lettuce, spinach, sugar cane, coffee, cocoa, pine, poplar, eucalyptus, apple tree, and grape.

Also provides are cells, seeds, and further generation progeny from the progeny plants generated by the methods disclosed herein. In some embodiments, the progeny plants and all parts and progeny derived therefrom are inbred to generate progeny plants that are substantially or completely homozygous at all loci.

In some embodiments, the progeny plants, parts, and/or later generation progeny derived therefrom comprise a transgene. As used herein, the term "transgene" refers to a nucleic acid molecule that is or was introduced into an organism or its ancestors by some form of artificial transfer technique. The artificial transfer technique thus creates a "transgenic organism" or a "transgenic cell". Examples of techniques by which this can be accomplished are known in the art. In some embodiments, a transgenic individual is a transgenic plant, and the technique employed to create the transgenic plant is selected from the group consisting of *Agrobacterium*-mediated transformation, biolistic methods, electroporation, in planta techniques, and the like. Transgenic individuals can also arise from sexual crosses or by selfing of transgenic individuals into which exogenous polynucleotides have been introduced.

It is further understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breedings result in the artificially transferred nucleic acid molecule being present in the progeny individual. In some embodiments, a transgene comprises a nucleic acid sequence that encodes a gene product that provides resistance to a herbicide selected from among glyphosate, Sulfonylurea, imidazolinione, dicamba, glufosinate, phenoxy proprionic acid, cycloshexome, traizine, benzonitrile, and broxynil.

VI. Computer-Based Implementations

The presently disclosed subject matter also provides computer-related implementations of the presently disclosed methods. In some embodiments, one or more steps of the disclosed methods are performed by a suitably-programmed computer. For example, in any of the disclosed methods, the inferring step, the simulating step, or both can be performed by a suitably-programmed computer. Particularly as the complexity of the genomes increases and the numbers of inferring steps and/or simulating steps increase, it can be beneficial to employ a suitably-programmed computer to perform the necessary calculations. By way of example and not limitation, the simulating step can comprise simulating at least 100, 200, 300, 400, 500, 1000 or more progeny in each the progeny generation. A suitably programmed computer can facilitate these simulations.

Alternatively or in addition, the estimating step can comprise estimating effects with respect to the desired phenotype of the plurality of genome-wide markers based on phenotypic best linear unbiased predictions (BLUPs) and marker genotypic data in the biparental breeding population using genome-wide best linear unbiased prediction (GBLUP) as set forth hereinabove. Also, the estimating step can comprise estimating genetic variance by restrained maximum likelihood estimation (REML) based on phenotypic data from multiple locations using Equation (1) above, and/or the inferring step can comprise employing a minimum recombination principle (MRP), and/or the breeding population can consists of n members and the repeating comprises simulating all n(n−1)/2 unique crosses of the members of the breeding population. In any of these exemplary embodiments, a suitably programmed computer can facilitate these steps.

Furthermore, the presently disclosed subject matter methods can be employed in cases where the trait of interest comprises at least two independent traits of interest. In some embodiments, the methods further comprise assigning to each independent trait of interest an importance value relative to the other independent traits. Here as well, a suitably programmed computer can facilitate the practice of these methods.

VII. Further Considerations

The methods of the presently disclosed subject matter can be employed with inbred or outbred individuals, including but not limited to elite lines of agriculturally important crop species. Thus, in some embodiments each breeding partner is an inbred individual.

Additionally, it is understood that any type of marker can be employed in the instantly disclosed methods. For example, in some embodiments the one or more genome-wide markers are selected from the group consisting of single nucleotide polymorphisms (SNPs), insertions/deletions (indels), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, amplified fragment length polymorphisms (AFLPs), and combinations thereof. In some embodiments, the one or more genome-wide markers comprise at least one marker present within every 5 cM, 3 cM, 2 cM, 1 cM, 0.5 cM, or 0.25 cM interval in the genomes of the breeding partners.

Additionally, the methods of the presently disclosed subject matter provide in some embodiments a selecting step in which one or more breeding pairs are selected based on the ranking step of each method. The selecting can take into account any aspect of the simulations, and in some embodiments comprises selecting the breeding pairs with GPVs of the top 20%, 10%, 5%, or 1%.

EXAMPLES

The following Examples provide illustrative embodiments of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Simulations Designed to Compare MAS, GWS, and GWS-SMART

In order to evaluate the performance of the presently disclosed methods, simulation experiments were performed following the selection scheme described herein and shown in FIG. 2. In each of 100 replicates of simulations, DH populations of 250 individuals were generated based on ten 190-cM chromosomes with 20 evenly spaced markers on each chromosome. The model $$y_i = \mu + \sum_{j=1}^{Q} (q_{ij} a_j) + e_i$$

where $y_i$ was the phenotype of individual i, $\mu$ was overall mean, $g_{ij}$ was the genotype of QTL j of individual i, $a_j$ was the main effect of QTL j, Q was the total number of QTL (Q=50 in our simulation studies), and environmental error $e_i$ for $y_i$ was sampled from a normal distribution with mean zero and variance $\sigma_e^2$. At the jth QTL, the testcross effect of the favorable allele was simulated as $a_j = \lambda^k$ with $\lambda = (Q-1)/(Q+1)$ (Lande & Thompson, 1990). The environmental noise ei was sampled from a N(0, $\sigma_e^2$) with $\sigma_e^2 = (V_g/H^2) - V_g$ where the given heritability $H^2 = 0.30$ and the genetic variance of QTL $V_g$ was calculated as $$V_g = \sum_{j=1}^{Q} a_j^2.$$

Five (5) cycles of selection were performed for each of GWS-SMART, GWS, and MAS. At cycle 0, QTL in MAS were identified by stepwise regression with a given significance level 0.05, and QTL effects were estimated by multiple linear regression (Bernardo & Yu, 2007). In GWS and GWS-SMART, effects of each marker were estimated by GBLUP (Meuwissen et al., 2001). In cycle 0, the top 5 lines were selected to recombine to generate cycle 1 as suggested by Bernardo & Yu, 2007. In cycle 1, for MAS and GWS, the top 5 lines were selected based on their predicted breeding values, and these selected lines were then intercrossed or recombined to produce the cycle 1 population. It is noted that the total number of crosses made based on the selected the top 5 lines was (5×4)/2=10.

In GWS-SMART as shown in FIG. 3, 1000 populations were simulated from a cross of two individuals, and the sample size of each population was 50. The top 10 crosses with high GPV were actually selected to produce the next cycle population. The selection response was calculated as the difference between the phenotypic means of a tested population and its parental population. The procedures for MAS, GWS, and GWS-SMART were repeated from cycle 0 to cycle 4.

FIG. 4 shows the results from these simulations. As expected, the exemplary method of the presently disclosed subject matter (GWS-SMART) was superior to traditional GWS and MAS. In cycle 1 to cycle 4, the selection response with GWS-SMART was 5% to 9% higher than that with GWS, and 19% to 27% higher than that with MAS. The results show the advantages of GWS-SMART over conventional GWS and MAS, while more simulation and real data analysis are needed to evaluate them for different traits and different breeding populations across different crops in the future.

Example 2

Exemplary GWS-SMART Implementations

The exemplary method of the presently disclosed subject matter was employed to predict the best crosses at cycle 0 based on genotypic and phenotypic data in the cycle. The training population was a cycle 0 double haploid (DH) corn population derived from two inbred parents: A and B. This population was produced by crossing the two inbred parents to produce an $F_1$, then, a DH population was generated from the $F_1$ individuals using standard double haploid techniques. The DH population was crossed with a tester T, and the phenotypes of each line were evaluated based on their testcross performances. The traits of interest in the study were grain yield and grain moisture. 344 lines in the DH population were genotyped using 240 SNP markers, and these lines were phenotyped in six locations (referred to herein as "A", "B", "C", "D", "E", and "F") in five different states of the United States.

First, BLUP of each line for grain yield and grain moisture was calculated based on the phenotypic data from the six locations as shown in Table 1. As described in the previous section, the calculation of the BLUPs were based on model (1) using REML under a mixed model frame. These BLUPs were listed in Table 2.

TABLE 1

Original Phenotypic Data for Grain Moisture and Yield from a Training Population

| | Grain yield | | | | | | Grain moisture | | | | | |
|---|---|---|---|---|---|---|---|---|---|---|---|---|
| Line ID | 7201 | 7212 | 7220 | 7330 | 8504 | 8644 | 7201 | 7212 | 7220 | 7330 | 8504 | 8644 |
| 1 | 204.1 | 245.5 | 200.2 | n.d. | 163.7 | 133.8 | 13.08 | 18.52 | 15.42 | n.d. | 13.10 | 15.58 |
| 2 | n.d. | 255.0 | 212.0 | n.d. | 178.0 | 139.3 | n.d. | 19.26 | 15.62 | n.d. | 13.72 | 15.56 |
| 3 | 227.2 | 250.4 | 213.7 | 189.8 | 178.3 | 153.7 | 13.38 | 18.46 | 16.06 | 25.94 | 13.46 | 16.18 |
| 4 | 210.8 | 254.8 | 209.3 | n.d. | 177.1 | 147.0 | 14.04 | 20.02 | 16.56 | n.d. | 14.46 | 17.18 |
| 5 | 217.4 | 258.7 | 220.4 | n.d. | 181.3 | 145.0 | 14.30 | 19.86 | 16.50 | n.d. | 14.92 | 17.38 |
| 6 | 224.6 | 245.4 | 217.7 | 192.3 | 179.3 | 156.4 | 13.56 | 18.44 | 16.54 | 26.20 | 14.20 | 16.54 |
| 7 | 227.8 | 269.3 | 225.1 | n.d. | 181.7 | n.d. | 14.24 | 19.92 | 16.50 | n.d. | 14.20 | n.d. |
| 8 | 206.9 | 244.1 | 197.9 | n.d. | 172.0 | 132.2 | 13.26 | 18.38 | 15.00 | n.d. | 13.32 | 15.44 |
| 9 | 254.8 | 265.7 | 238.0 | 207.6 | 204.3 | 175.0 | 14.20 | 19.20 | 16.54 | 27.18 | 14.38 | 16.88 |
| 10 | 209.7 | 256.2 | 213.1 | n.d. | 173.2 | 137.5 | 13.12 | 18.72 | 15.32 | n.d. | 13.76 | 15.50 |
| 11 | n.d. | 273.5 | 243.5 | 214.8 | 214.8 | 179.4 | n.d. | 18.88 | 16.00 | 26.30 | 14.02 | 17.18 |
| 12 | 237.9 | 251.9 | 227.0 | 197.1 | 189.9 | 161.7 | 13.68 | 18.82 | 16.46 | 26.54 | 14.42 | 17.76 |
| 13 | 214.4 | 259.0 | 216.9 | n.d. | 184.0 | 146.4 | 14.06 | 19.56 | 16.44 | n.d. | 14.44 | 17.18 |
| 14 | 204.9 | 245.7 | 200.2 | n.d. | 169.7 | 131.7 | 12.72 | 18.14 | 15.16 | n.d. | 13.22 | 15.02 |
| 15 | 215.1 | 252.8 | 208.4 | n.d. | 173.8 | 146.5 | 13.30 | 18.96 | 15.26 | n.d. | 13.24 | 16.14 |
| 16 | 205.8 | 248.8 | 201.8 | n.d. | 168.6 | n.d. | 14.26 | 19.94 | 16.58 | n.d. | 14.90 | n.d. |
| 17 | 211.8 | 255.1 | 216.3 | n.d. | 181.1 | 140.1 | 13.42 | 19.22 | 15.52 | n.d. | 13.98 | 16.40 |
| 18 | 211.5 | 255.6 | 206.5 | n.d. | 177.0 | 136.3 | 12.92 | 18.74 | 15.64 | n.d. | 13.66 | 15.40 |

TABLE 1-continued

Original Phenotypic Data for Grain Moisture and Yield from a Training Population

| | Grain yield | | | | | | Grain moisture | | | | | |
|---|---|---|---|---|---|---|---|---|---|---|---|---|
| Line ID | 7201 | 7212 | 7220 | 7330 | 8504 | 8644 | 7201 | 7212 | 7220 | 7330 | 8504 | 8644 |
| 19 | n.d. | 259.5 | 213.9 | n.d. | 185.8 | 151.9 | n.d. | 18.72 | 15.32 | n.d. | 13.04 | 15.82 |
| 20 | 236.2 | 272.1 | 230.7 | n.d. | 198.1 | 160.1 | 13.98 | 19.60 | 16.26 | n.d. | 14.40 | 17.14 |
| 21 | 203.9 | 244.1 | 199.3 | n.d. | 166.5 | 132.9 | 13.52 | 19.12 | 15.70 | n.d. | 13.88 | 15.88 |
| 22 | 204.6 | n.d. | 200.1 | n.d. | 167.2 | 130.9 | 12.90 | n.d. | 15.16 | n.d. | 13.48 | 15.98 |
| 23 | 200.3 | 244.5 | 192.4 | n.d. | 158.8 | 134.5 | 13.74 | 19.56 | 16.28 | n.d. | 14.60 | 16.94 |
| 24 | n.d. | 241.9 | 197.4 | n.d. | 166.4 | 122.8 | n.d. | 19.12 | 15.34 | n.d. | 13.56 | 15.88 |
| 25 | n.d. | n.d. | 227.8 | n.d. | 194.2 | 158.7 | n.d. | 19.28 | 15.78 | n.d. | 14.18 | 17.12 |
| 26 | 220.3 | 261.8 | 218.9 | n.d. | 184.5 | 147.0 | 14.22 | 19.98 | 16.60 | n.d. | 14.88 | 17.26 |
| 27 | 225.2 | 260.9 | 215.6 | n.d. | 190.0 | 152.3 | 13.12 | 19.20 | 16.12 | n.d. | 13.88 | 15.82 |
| 28 | 213.4 | 254.6 | 205.0 | n.d. | 174.4 | 142.4 | 13.30 | 18.98 | 15.88 | 25.70 | 13.84 | 15.68 |
| 29 | n.d. | 267.4 | 221.0 | 202.8 | 193.7 | 166.5 | n.d. | 20.10 | 16.40 | 26.36 | 14.94 | 17.34 |
| 30 | 220.4 | 256.6 | 208.7 | 194.0 | 183.5 | 148.7 | 12.20 | 17.98 | 14.52 | 24.56 | 13.18 | 14.86 |
| 31 | 233.9 | 266.2 | 219.3 | 203.6 | 192.8 | 161.0 | 13.60 | 19.50 | 16.32 | 25.94 | 14.42 | 17.26 |
| 32 | 209.3 | 249.3 | 202.0 | 184.1 | 164.8 | 142.6 | 13.38 | 18.78 | 15.50 | 26.10 | 13.44 | 15.86 |
| 33 | 240.1 | 275.8 | 230.3 | 210.2 | 201.7 | 166.2 | 13.58 | 19.64 | 16.18 | 26.04 | 14.62 | 16.08 |
| 34 | 231.9 | 268.4 | 227.5 | 202.2 | 196.7 | 160.5 | 13.40 | 19.36 | 15.92 | 25.66 | 14.08 | 17.08 |
| 35 | 213.3 | 255.9 | 207.3 | 187.9 | 174.6 | 143.4 | 12.92 | 18.48 | 15.34 | 25.26 | 13.84 | 15.46 |
| 36 | 195.7 | 237.3 | 190.8 | 171.1 | 160.7 | 126.4 | 12.64 | 18.14 | 15.10 | 24.86 | 13.14 | 15.48 |
| 37 | 215.7 | 249.9 | 209.3 | 189.7 | 175.2 | 140.7 | 12.78 | 18.42 | 15.38 | 25.24 | 13.56 | 15.40 |
| 38 | 201.7 | n.d. | 191.6 | 176.7 | 159.3 | 129.1 | 12.02 | n.d. | 14.66 | 24.52 | 12.64 | 15.68 |
| 39 | 202.7 | 252.7 | 208.5 | n.d. | 174.6 | 136.6 | 13.08 | 18.86 | 15.50 | n.d. | 13.84 | 15.64 |
| 40 | 202.2 | 246.7 | 202.3 | 180.5 | 170.4 | 141.6 | 13.28 | 19.14 | 16.14 | 25.88 | 14.22 | 16.68 |
| 41 | 210.9 | 249.6 | 201.6 | 185.1 | 166.0 | 132.9 | 12.34 | 17.98 | 14.52 | 24.82 | 13.12 | 15.58 |
| 42 | 207.9 | 253.1 | 202.3 | 185.4 | 177.3 | 140.9 | 12.62 | 18.62 | 15.40 | 25.56 | 13.44 | 15.08 |
| 43 | 218.4 | 250.6 | 207.5 | 190.3 | 170.1 | 145.2 | 13.14 | 18.38 | 15.32 | 25.20 | 13.34 | 15.50 |
| 44 | 221.5 | 259.7 | 215.6 | 190.3 | 181.0 | 152.0 | 14.16 | 19.44 | 16.44 | 26.72 | 14.46 | 16.88 |
| 45 | 227.3 | 260.4 | 221.5 | 197.0 | 182.5 | 152.0 | 13.90 | 19.16 | 16.30 | 26.64 | 14.08 | 16.84 |
| 46 | 198.0 | 241.5 | 190.1 | n.d. | 151.4 | n.d. | 13.74 | 19.26 | 16.02 | n.d. | 13.48 | n.d. |
| 47 | 206.8 | n.d. | 203.1 | n.d. | 172.6 | 132.1 | 12.28 | n.d. | 14.76 | n.d. | 13.24 | 15.82 |
| 48 | 217.8 | 260.7 | 214.1 | 191.9 | 180.0 | 149.2 | 12.62 | 18.28 | 15.06 | 24.96 | 13.24 | 15.22 |
| 49 | 230.7 | 265.7 | 224.6 | 200.4 | 185.8 | 155.7 | 12.64 | 18.10 | 14.94 | 24.40 | 13.42 | 14.72 |
| 50 | 217.9 | 253.2 | 205.2 | n.d. | 169.3 | 143.3 | 13.44 | 19.26 | 16.22 | n.d. | 13.74 | 16.02 |
| 51 | 233.6 | 264.8 | 222.2 | 200.9 | 185.5 | 157.8 | 13.66 | 18.78 | 16.02 | 26.32 | 13.86 | 15.78 |
| 52 | n.d. | 249.7 | 209.2 | 188.0 | 180.4 | 144.3 | n.d. | 18.26 | 15.20 | 25.16 | 13.44 | 16.38 |
| 53 | 211.5 | 248.5 | 202.6 | 185.7 | 171.8 | 137.7 | 12.66 | 18.70 | 15.22 | 25.50 | 13.58 | 15.10 |
| 54 | 213.3 | 249.4 | 207.2 | 186.2 | 169.3 | 139.6 | 12.82 | 18.68 | 15.40 | 25.36 | 14.00 | 15.32 |
| 55 | 203.7 | 243.8 | 195.0 | 178.0 | 164.0 | 132.7 | 12.54 | 18.26 | 15.08 | 25.02 | 13.44 | 15.24 |
| 56 | 215.3 | 249.1 | 204.0 | 186.9 | 173.4 | 141.4 | 13.58 | 18.72 | 15.86 | 25.68 | 13.80 | 16.36 |
| 57 | 212.6 | 252.4 | 205.9 | 189.6 | 175.6 | 143.8 | 14.18 | 20.00 | 16.62 | 26.82 | 14.98 | 17.12 |
| 58 | 204.7 | 244.6 | 206.3 | 184.8 | 161.3 | 133.9 | 13.00 | 18.64 | 15.68 | 25.68 | 13.40 | 16.02 |
| 59 | 200.1 | 243.5 | 193.8 | 179.7 | 158.5 | 138.7 | 13.86 | 19.38 | 16.30 | 26.20 | 14.18 | 16.92 |
| 60 | 230.5 | 262.1 | 219.4 | 198.9 | 191.3 | 151.7 | 13.20 | 18.42 | 15.36 | 25.30 | 13.90 | 15.72 |
| 61 | 226.9 | 260.8 | 217.3 | 197.3 | n.d. | 153.6 | 12.64 | 18.22 | 15.64 | 24.82 | n.d. | 15.34 |
| 62 | 219.1 | 254.6 | 209.3 | 189.8 | 179.1 | 146.1 | 13.70 | 19.38 | 16.28 | 26.34 | 14.24 | 15.98 |
| 63 | 212.6 | 252.7 | 203.7 | 188.1 | 163.8 | 137.1 | 13.14 | 18.86 | 15.66 | 25.66 | 13.38 | 16.38 |
| 64 | 226.9 | 263.9 | 217.5 | 196.9 | 185.3 | 149.5 | 13.10 | 19.14 | 15.70 | 26.14 | 13.74 | 16.74 |
| 65 | 235.0 | 271.0 | 223.5 | 205.4 | 192.7 | 163.4 | 13.86 | 19.18 | 16.08 | 26.10 | 14.22 | 16.64 |
| 66 | 219.6 | 263.5 | 214.4 | 197.6 | 185.9 | 152.3 | 14.14 | 20.06 | 16.84 | 26.54 | 15.08 | 17.26 |
| 67 | 218.8 | 257.0 | 213.2 | 191.8 | 181.8 | 145.4 | 13.86 | 19.32 | 16.32 | 26.66 | 14.64 | 16.76 |
| 68 | 213.2 | 247.4 | 202.4 | 184.4 | 166.1 | 141.5 | 14.26 | 20.26 | 17.16 | 26.52 | 14.76 | 16.92 |
| 69 | 206.3 | 245.2 | 200.5 | 182.7 | 164.4 | 134.1 | 13.44 | 19.16 | 16.04 | 25.64 | 13.70 | 16.62 |
| 70 | 204.8 | 244.6 | 196.7 | 181.6 | 169.6 | 138.5 | 13.50 | 19.26 | 16.06 | 26.30 | 14.18 | 17.00 |
| 71 | 224.6 | 265.1 | 227.0 | 202.2 | 193.2 | 160.3 | 13.78 | 19.60 | 16.32 | 26.62 | 14.76 | 17.50 |
| 72 | 201.4 | 248.6 | 202.5 | n.d. | 171.9 | 138.2 | 13.68 | 19.26 | 16.00 | n.d. | 14.18 | 16.20 |
| 73 | 213.2 | 249.9 | 210.1 | 187.5 | 174.8 | 150.1 | 14.52 | 20.28 | 17.18 | 26.94 | 15.04 | 17.74 |
| 74 | 213.6 | 246.9 | 200.2 | 182.9 | 170.9 | 136.0 | 12.52 | 17.60 | 14.50 | 25.10 | 12.90 | 15.36 |
| 75 | 215.9 | 260.7 | 214.2 | 196.8 | n.d. | 149.3 | 14.40 | 20.06 | 17.02 | 26.88 | n.d. | 16.88 |
| 76 | n.d. | 249.8 | 204.6 | 184.4 | 176.3 | 140.0 | n.d. | 18.42 | 15.76 | 25.74 | 13.62 | 15.96 |
| 77 | 219.3 | 252.7 | 210.8 | 188.9 | 179.0 | 150.8 | 13.30 | 18.94 | 15.50 | 25.98 | 13.96 | 16.24 |
| 78 | 249.8 | 285.4 | 245.1 | n.d. | 210.1 | 174.0 | 14.36 | 20.10 | 16.28 | n.d. | 14.38 | 16.36 |
| 79 | 194.2 | 240.8 | 196.2 | 175.9 | 160.0 | 127.2 | 12.66 | 18.54 | 15.34 | 25.18 | 13.70 | 15.42 |
| 80 | 224.1 | 256.3 | 213.1 | 195.3 | 182.5 | 144.6 | 12.82 | 18.06 | 15.14 | 25.52 | 13.34 | 16.06 |
| 81 | 220.8 | 259.9 | 208.1 | 191.5 | 182.6 | 143.9 | 13.54 | 19.30 | 16.32 | 25.98 | 14.52 | 17.14 |
| 82 | 206.4 | 245.1 | 207.0 | 186.5 | 172.4 | 135.6 | 13.14 | 18.52 | 15.48 | 25.50 | 13.92 | 16.14 |
| 83 | n.d. | 263.7 | 218.4 | 199.2 | 194.4 | 154.7 | n.d. | 19.48 | 16.16 | 25.94 | 14.32 | 16.06 |
| 84 | 213.7 | 253.6 | 209.9 | n.d. | 173.0 | 138.2 | 12.84 | 18.24 | 15.12 | 25.14 | 13.32 | 15.78 |
| 85 | 203.8 | 251.4 | 206.4 | 186.5 | 165.0 | 135.5 | 12.32 | 17.98 | 14.90 | 24.78 | 12.78 | 15.52 |
| 86 | n.d. | 267.7 | 220.1 | n.d. | 187.8 | 158.2 | n.d. | 19.00 | 15.74 | n.d. | 13.88 | 16.48 |
| 87 | 209.7 | 244.2 | 200.8 | 183.9 | 169.5 | 135.1 | 13.46 | 18.72 | 15.88 | 26.04 | 13.88 | 15.74 |
| 88 | 219.1 | 260.4 | 217.5 | 194.3 | 181.2 | 152.1 | 13.40 | 19.00 | 15.90 | 26.40 | 14.02 | 16.44 |
| 89 | 225.0 | 258.1 | 212.0 | 194.7 | 184.6 | 145.7 | 13.24 | 18.86 | 15.54 | 25.20 | 13.88 | 16.50 |
| 90 | 230.0 | 265.1 | 218.0 | 203.1 | 190.2 | 155.6 | 12.94 | 18.30 | 15.02 | 25.24 | 13.56 | 15.84 |
| 91 | 200.6 | 243.6 | 195.2 | 181.4 | 172.1 | 131.8 | 12.68 | 18.52 | 15.46 | 25.00 | 13.40 | 15.96 |
| 92 | 220.8 | 256.8 | 213.7 | 192.1 | 180.2 | 150.6 | 14.52 | 20.20 | 17.12 | 27.02 | 15.38 | 17.56 |

TABLE 1-continued

Original Phenotypic Data for Grain Moisture and Yield from a Training Population

| | Grain yield | | | | | | Grain moisture | | | | | |
|---|---|---|---|---|---|---|---|---|---|---|---|---|
| Line ID | 7201 | 7212 | 7220 | 7330 | 8504 | 8644 | 7201 | 7212 | 7220 | 7330 | 8504 | 8644 |
| 93 | 219.8 | 257.4 | 214.9 | n.d. | 184.7 | 144.4 | 13.44 | 19.00 | 15.76 | n.d. | 14.02 | 16.60 |
| 94 | n.d. | 257.1 | 217.0 | 193.4 | 178.8 | 153.3 | n.d. | 19.38 | 16.30 | 26.02 | 14.70 | 16.66 |
| 95 | 231.1 | 264.8 | 220.2 | 201.8 | 188.7 | 157.6 | 12.50 | 18.26 | 14.96 | 25.00 | 13.18 | 15.16 |
| 96 | 217.2 | 254.6 | 206.4 | 189.0 | 179.0 | 140.9 | 13.80 | 19.10 | 16.12 | 26.50 | 14.46 | 16.00 |
| 97 | 216.9 | 251.0 | 210.4 | 190.3 | 168.2 | 140.0 | 13.28 | 18.76 | 15.78 | 26.30 | 13.52 | 16.84 |
| 98 | 223.9 | 258.5 | 215.6 | 196.5 | 186.9 | 149.2 | 12.84 | 18.82 | 15.32 | 25.34 | 13.50 | 15.42 |
| 99 | 212.3 | 252.1 | 206.7 | 184.3 | 170.3 | 139.2 | 13.34 | 18.72 | 15.62 | 25.08 | 13.98 | 15.60 |
| 100 | 210.0 | 257.9 | 213.9 | n.d. | 183.1 | 142.3 | 14.30 | 20.24 | 16.90 | n.d. | 14.90 | 17.50 |
| 101 | 219.7 | 254.4 | 213.8 | 192.5 | 184.5 | 152.9 | 13.54 | 19.14 | 15.90 | 26.24 | 13.94 | 16.46 |
| 102 | 217.4 | 256.4 | 213.4 | 193.6 | 183.2 | 149.1 | 13.24 | 18.80 | 15.92 | 25.82 | 14.28 | 16.52 |
| 103 | 230.6 | 267.2 | 223.9 | 200.3 | 190.2 | 159.3 | 13.34 | 19.36 | 15.88 | 25.82 | 14.08 | 16.04 |
| 104 | 203.2 | 241.9 | 197.2 | 177.6 | 161.5 | 132.1 | 13.86 | 19.36 | 16.70 | 26.70 | 14.12 | 16.32 |
| 105 | 208.0 | 250.9 | 205.3 | 183.3 | 164.4 | 139.2 | 13.56 | 19.32 | 16.14 | 26.98 | 14.38 | 16.00 |
| 106 | 228.8 | 259.8 | 216.0 | 193.0 | 173.3 | 149.5 | 13.60 | 19.06 | 15.66 | 26.58 | 13.58 | 16.12 |
| 107 | 203.3 | 245.2 | 203.3 | 179.7 | 162.7 | 131.5 | 12.82 | 18.82 | 15.44 | 26.24 | 13.60 | 15.70 |
| 108 | 228.9 | 261.2 | 218.6 | 196.6 | 177.9 | 152.2 | 12.96 | 18.74 | 15.72 | 26.12 | 13.52 | 15.86 |
| 109 | 231.8 | 264.1 | 216.4 | 195.7 | 179.9 | 154.4 | 14.56 | 19.88 | 17.08 | 27.50 | 14.62 | 16.68 |
| 110 | 216.3 | 247.7 | 206.7 | 183.3 | 168.0 | 138.7 | 13.82 | 19.40 | 16.34 | 26.74 | 14.26 | 16.84 |
| 111 | 209.6 | 245.1 | 206.7 | 182.7 | 154.5 | 139.3 | 13.00 | 18.52 | 15.64 | 26.34 | 13.00 | 16.62 |
| 112 | 196.7 | 237.5 | 198.8 | 173.3 | 156.9 | 131.4 | 12.70 | 18.58 | 15.42 | 25.96 | 13.40 | 16.32 |
| 113 | 226.0 | 263.2 | 226.7 | 196.5 | 183.9 | 156.8 | 15.14 | 20.68 | 17.86 | 28.04 | 15.46 | 18.26 |
| 114 | 223.1 | 253.3 | 212.7 | 189.8 | 174.0 | 153.6 | 13.14 | 18.22 | 15.80 | 26.50 | 13.46 | 16.06 |
| 115 | 224.2 | 254.2 | 219.4 | 189.0 | 175.8 | 148.3 | 13.50 | 18.94 | 16.12 | 27.38 | 14.18 | 15.94 |
| 116 | 213.4 | 251.3 | 213.6 | n.d. | 177.3 | 138.5 | 13.82 | 19.12 | 15.86 | n.d. | 14.24 | 16.04 |
| 117 | 216.4 | 255.0 | 211.6 | 186.7 | 169.1 | 153.3 | 13.84 | 19.98 | 17.00 | 27.86 | 14.92 | 17.26 |
| 118 | 225.0 | 263.9 | 222.7 | 196.1 | 179.8 | 159.3 | 13.88 | 19.84 | 16.40 | 27.12 | 14.74 | 16.50 |
| 119 | 213.1 | 250.2 | 210.1 | 185.6 | n.d. | n.d. | 13.44 | 18.96 | 16.08 | 26.42 | n.d. | n.d. |
| 120 | 223.7 | 264.9 | 222.8 | n.d. | 188.6 | 152.1 | 13.50 | 18.94 | 15.74 | n.d. | 13.60 | 16.40 |
| 121 | 212.8 | 252.0 | 213.5 | 187.7 | 169.9 | 144.4 | 13.28 | 19.18 | 15.80 | 26.92 | 13.60 | 15.64 |
| 122 | n.d. | 259.9 | 216.7 | 192.8 | 174.2 | 151.3 | n.d. | 19.94 | 16.98 | 27.66 | 14.90 | 16.40 |
| 123 | 232.4 | 260.4 | 218.1 | 196.7 | 177.5 | 151.5 | 13.58 | 18.66 | 15.64 | 26.48 | 14.16 | 16.10 |
| 124 | n.d. | 268.2 | 227.9 | n.d. | 197.8 | 153.3 | n.d. | 19.86 | 16.12 | n.d. | 14.26 | 17.36 |
| 125 | 232.1 | 263.7 | 219.6 | 196.4 | 178.7 | 158.0 | 12.70 | 18.48 | 15.08 | 26.00 | 13.60 | 15.36 |
| 126 | n.d. | 257.0 | 218.6 | n.d. | 181.2 | 143.2 | n.d. | 19.68 | 15.98 | n.d. | 14.26 | 16.78 |
| 127 | 232.2 | 264.6 | 224.5 | 197.6 | 183.2 | 153.8 | 14.16 | 20.18 | 16.80 | 27.44 | 14.66 | 17.06 |
| 128 | 211.4 | 243.3 | 200.0 | 177.6 | 164.9 | 131.2 | 12.82 | 18.52 | 15.28 | 25.84 | 13.00 | 15.76 |
| 129 | 233.8 | 261.0 | 222.0 | 197.8 | 188.1 | 163.3 | 14.30 | 19.52 | 16.70 | 27.36 | 14.46 | 17.22 |
| 130 | 214.8 | 246.7 | 205.1 | 182.1 | 159.5 | 141.5 | 13.44 | 19.16 | 15.82 | 26.36 | 13.52 | 15.88 |
| 131 | 225.6 | 261.6 | 213.9 | n.d. | 171.3 | 153.3 | 13.10 | 18.60 | 15.56 | n.d. | 13.00 | 15.94 |
| 132 | 237.1 | 270.9 | 225.0 | 201.0 | 179.4 | 161.7 | 13.74 | 19.22 | 16.22 | 26.66 | 13.58 | 16.12 |
| 133 | 221.0 | 260.1 | 218.4 | n.d. | 188.6 | 150.1 | 13.88 | 20.02 | 16.22 | n.d. | 14.40 | 17.54 |
| 134 | 249.7 | 280.9 | 235.5 | 211.0 | 202.7 | 175.8 | 14.28 | 20.26 | 17.10 | 27.60 | 15.04 | 17.96 |
| 135 | 217.3 | 251.4 | 214.3 | 188.2 | n.d. | 140.2 | 12.32 | 17.68 | 14.98 | 26.16 | n.d. | 15.84 |
| 136 | 219.7 | n.d. | 213.5 | 186.9 | 173.5 | 146.6 | 13.38 | 18.96 | 16.24 | 27.14 | 14.06 | 17.14 |
| 137 | 227.6 | 262.3 | 216.6 | 196.8 | 184.6 | 155.8 | 14.72 | 20.66 | 17.52 | 28.10 | 15.52 | 17.30 |
| 138 | 230.6 | 264.5 | 223.0 | 194.6 | 186.6 | 153.5 | 13.74 | 19.52 | 16.40 | 27.12 | 14.30 | 16.34 |
| 139 | 223.7 | n.d. | 213.8 | 191.3 | 178.3 | 149.0 | 15.22 | n.d. | 17.60 | 28.40 | 15.58 | 17.42 |
| 140 | 227.1 | 258.6 | 222.3 | 191.7 | 182.9 | 151.8 | 13.22 | 18.80 | 15.82 | 26.50 | 13.70 | 15.82 |
| 141 | 204.4 | 245.8 | n.d. | 176.9 | 152.0 | 132.7 | 13.28 | 19.06 | n.d. | 27.28 | 13.50 | 16.60 |
| 142 | 216.1 | 252.9 | 209.8 | 190.1 | 171.9 | 143.3 | 13.04 | 19.14 | 15.90 | 26.60 | 13.72 | 16.46 |
| 143 | 239.6 | 269.4 | 227.4 | 200.8 | 191.8 | 163.5 | 13.16 | 18.88 | 15.46 | 26.16 | 13.66 | 15.54 |
| 144 | 220.7 | 258.1 | 215.0 | 189.7 | 176.6 | 145.9 | 14.06 | 19.86 | 16.48 | 26.84 | 14.58 | 17.46 |
| 145 | 230.4 | 269.1 | 228.1 | 200.3 | 179.2 | 154.4 | 13.02 | 18.54 | 15.62 | 26.08 | 13.16 | 16.40 |
| 146 | 234.6 | 263.5 | 226.8 | n.d. | 185.8 | 154.7 | 14.06 | 19.22 | 16.30 | n.d. | 14.42 | 17.30 |
| 147 | 219.1 | 256.6 | 210.3 | n.d. | 183.5 | 142.0 | 13.60 | 18.74 | 15.76 | n.d. | 13.76 | 16.04 |
| 148 | 212.9 | 243.7 | 201.2 | 181.1 | 157.1 | 140.7 | 13.22 | 18.38 | 15.58 | 26.58 | 13.20 | 15.96 |
| 149 | 219.8 | 248.4 | 208.5 | 186.0 | 163.5 | 145.5 | 13.98 | 19.46 | 16.28 | 27.20 | 14.28 | 16.62 |
| 150 | 210.2 | 248.7 | 203.9 | 183.1 | 166.7 | 138.7 | 13.70 | 19.32 | 16.56 | 27.04 | 14.52 | 16.60 |
| 151 | 222.9 | 251.0 | 214.1 | 186.3 | 172.9 | 144.1 | 14.34 | 19.50 | 16.58 | 27.30 | 14.70 | 17.18 |
| 152 | 228.8 | 258.8 | 222.4 | 196.4 | 174.6 | 150.4 | 13.10 | 18.56 | 15.84 | 26.54 | 13.28 | 16.38 |
| 153 | 212.3 | 249.0 | 206.8 | 184.0 | n.d. | 138.2 | 12.66 | 18.42 | 15.48 | 25.62 | n.d. | 15.72 |
| 154 | 224.3 | 262.8 | 221.6 | n.d. | 180.8 | 153.6 | 13.12 | 18.62 | 15.02 | n.d. | 12.82 | 15.76 |
| 155 | 225.1 | 255.6 | 213.8 | 192.1 | 179.5 | 149.8 | 12.78 | 18.34 | 15.48 | 26.16 | 13.30 | 16.44 |
| 156 | 213.1 | 250.9 | 206.2 | 186.1 | 170.0 | 141.5 | 13.38 | 19.56 | 15.94 | 27.44 | 14.24 | 16.08 |
| 157 | 219.5 | 259.4 | 217.5 | 191.1 | 174.0 | 143.9 | 12.98 | 18.42 | 15.78 | 27.20 | 13.32 | 16.36 |
| 158 | 217.1 | 258.5 | 211.1 | n.d. | 181.3 | 144.3 | 13.18 | 19.14 | 15.66 | n.d. | 13.56 | 15.60 |
| 159 | 225.1 | 259.8 | 218.8 | 188.5 | 178.9 | 151.6 | 13.14 | 18.92 | 16.00 | 27.00 | 14.04 | 16.90 |
| 160 | 208.8 | 244.5 | 202.7 | 175.9 | 159.7 | 133.4 | 13.16 | 18.52 | 15.54 | 26.12 | 13.48 | 15.44 |
| 161 | 213.2 | 251.2 | 210.5 | 186.3 | 171.0 | 140.0 | 12.24 | 17.68 | 14.84 | 25.58 | 12.92 | 15.84 |
| 162 | 255.3 | 283.5 | 240.3 | 214.4 | 204.4 | 180.3 | 13.20 | 18.48 | 15.30 | 26.20 | 13.58 | 15.96 |
| 163 | 210.3 | 249.6 | 209.4 | 181.2 | 172.5 | 140.9 | 14.68 | 20.56 | 17.62 | 28.14 | 15.40 | 17.98 |
| 164 | 219.4 | 249.3 | 207.1 | 188.0 | 169.3 | 142.9 | 14.10 | 19.58 | 16.48 | 27.48 | 14.46 | 16.62 |
| 165 | 233.4 | 265.5 | 226.1 | 197.1 | 189.3 | 154.5 | 12.96 | 18.74 | 15.30 | 26.58 | 13.28 | 15.96 |
| 166 | 226.9 | 256.8 | 215.1 | 189.6 | 176.6 | 156.4 | 14.08 | 19.78 | 16.52 | 27.06 | 14.46 | 17.02 |

TABLE 1-continued

Original Phenotypic Data for Grain Moisture and Yield from a Training Population

| | Grain yield | | | | | | Grain moisture | | | | | |
|---|---|---|---|---|---|---|---|---|---|---|---|---|
| Line ID | 7201 | 7212 | 7220 | 7330 | 8504 | 8644 | 7201 | 7212 | 7220 | 7330 | 8504 | 8644 |
| 167 | 217.0 | 248.1 | 210.6 | n.d. | 166.3 | n.d. | 14.02 | 19.46 | 16.44 | n.d. | 14.04 | n.d. |
| 168 | 230.5 | n.d. | 218.3 | 193.7 | 180.2 | 152.7 | 14.04 | 19.52 | 16.72 | 26.86 | 14.38 | 16.14 |
| 169 | 235.2 | 268.5 | 227.6 | 201.3 | 188.5 | 168.6 | 13.22 | 19.10 | 16.16 | 26.46 | 13.62 | 16.40 |
| 170 | 206.7 | 246.7 | 198.0 | 177.8 | 158.2 | 133.0 | 12.38 | 18.10 | 15.06 | 25.50 | 13.16 | 15.50 |
| 171 | 208.1 | 246.3 | 206.3 | 184.3 | 169.4 | 144.0 | 13.20 | 18.70 | 15.70 | 26.54 | 13.74 | 16.22 |
| 172 | 226.1 | 258.2 | 219.0 | 192.6 | 179.8 | 154.2 | 13.42 | 19.42 | 15.98 | 27.32 | 14.00 | 16.48 |
| 173 | 237.3 | 269.9 | 232.4 | 204.3 | 193.1 | 168.2 | 13.98 | 19.72 | 16.50 | 27.82 | 14.68 | 16.98 |
| 174 | 217.2 | 251.1 | 215.1 | 185.4 | 174.3 | 151.1 | 13.52 | 19.44 | 16.10 | 26.46 | 14.30 | 16.74 |
| 175 | 221.8 | 254.4 | 211.7 | 189.7 | 166.4 | 144.3 | 12.04 | 17.48 | 14.44 | 25.08 | 11.84 | 14.82 |
| 176 | 230.7 | 264.4 | 224.2 | 191.9 | 181.3 | n.d. | 13.04 | 18.32 | 15.30 | 26.48 | 13.46 | n.d. |
| 177 | 244.0 | n.d. | 234.7 | 202.9 | 192.9 | 165.7 | 13.84 | 19.00 | 16.08 | 27.28 | 14.02 | 16.62 |
| 178 | 219.6 | 253.8 | 206.5 | 185.9 | 172.5 | 144.8 | 13.22 | 18.82 | 15.90 | 27.10 | 14.00 | 16.88 |
| 179 | 216.7 | 245.2 | 205.4 | 183.1 | 161.1 | 137.4 | 13.96 | 19.18 | 16.18 | 27.52 | 13.76 | 16.86 |
| 180 | 222.9 | 253.3 | 214.3 | 187.0 | 177.4 | 152.4 | 13.02 | 18.58 | 15.58 | 25.96 | 13.56 | 16.26 |
| 181 | 219.4 | 251.6 | 206.2 | 187.4 | 168.6 | 145.9 | 12.84 | 18.70 | 15.74 | 26.16 | 13.70 | 16.60 |
| 182 | 221.9 | 258.7 | 220.0 | 191.4 | 179.4 | 153.3 | 12.14 | 17.74 | 14.66 | 25.80 | 12.78 | 15.02 |
| 183 | 231.2 | 260.9 | 219.7 | 194.8 | 185.4 | 154.4 | 13.32 | 19.10 | 16.04 | 26.44 | 13.80 | 15.92 |
| 184 | 218.5 | 256.1 | 211.3 | 186.4 | 171.9 | 143.4 | 13.84 | 19.46 | 16.40 | 26.78 | 14.34 | 17.08 |
| 185 | 229.5 | 277.2 | 233.0 | n.d. | 200.2 | 160.2 | 13.00 | 18.96 | 15.62 | n.d. | 13.88 | 16.22 |
| 186 | 221.8 | 257.3 | 219.1 | 188.5 | 179.9 | 150.3 | 12.60 | 18.20 | 15.66 | 25.62 | 13.58 | 15.90 |
| 187 | 221.6 | 253.0 | 215.0 | n.d. | 174.3 | 148.4 | 13.24 | 18.92 | 16.44 | n.d. | 14.30 | 17.28 |
| 188 | 220.3 | n.d. | 224.0 | 194.4 | 187.7 | 155.8 | 14.06 | n.d. | 17.04 | 27.30 | 14.92 | 17.66 |
| 189 | 213.6 | 250.9 | 208.1 | 185.2 | 173.7 | 144.1 | 14.08 | 19.60 | 16.98 | 26.56 | 14.88 | 18.06 |
| 190 | 212.0 | 250.5 | 217.7 | 188.9 | 170.4 | 147.7 | 13.06 | 18.78 | 15.90 | 25.94 | 13.38 | 17.04 |
| 191 | 221.4 | 252.7 | 217.6 | 192.8 | 180.6 | 157.1 | 13.10 | 18.72 | 15.68 | 25.46 | 13.62 | 16.94 |
| 192 | 226.4 | 262.2 | 225.0 | 200.2 | 186.7 | 167.2 | 13.30 | 18.94 | 16.42 | 25.88 | 14.40 | 17.52 |
| 193 | 203.9 | n.d. | 206.0 | n.d. | 167.5 | 130.0 | 13.22 | 18.78 | 15.52 | n.d. | 13.42 | 16.62 |
| 194 | 242.3 | 270.0 | 237.1 | 207.8 | 191.3 | 167.2 | 13.98 | 19.34 | 16.64 | 26.06 | 14.10 | 17.62 |
| 195 | 230.4 | 259.1 | 223.8 | 199.1 | 192.0 | 159.3 | 13.70 | 19.26 | 16.56 | 26.36 | 14.42 | 17.02 |
| 196 | 234.3 | 263.3 | 227.2 | 202.8 | 193.6 | 162.6 | 13.00 | 18.50 | 16.26 | 25.60 | 14.02 | 16.28 |
| 197 | 215.1 | 257.7 | 216.1 | 192.7 | 179.1 | 155.8 | 13.46 | 18.94 | 16.62 | 25.84 | 14.08 | 17.30 |
| 198 | 221.6 | 255.9 | 218.5 | 190.0 | 174.2 | 153.0 | 14.14 | 19.34 | 16.74 | 26.12 | 14.86 | 17.28 |
| 199 | n.d. | 241.3 | 203.1 | 179.7 | 167.6 | 135.7 | n.d. | 18.82 | 16.18 | 25.46 | 13.88 | 16.64 |
| 200 | 215.2 | 257.2 | 212.2 | n.d. | 170.6 | 136.9 | 13.60 | 19.06 | 15.72 | n.d. | 13.32 | 16.04 |
| 201 | 236.7 | 265.6 | 227.3 | 202.4 | 195.9 | 171.9 | 13.22 | 18.66 | 15.86 | 25.72 | 14.00 | 17.32 |
| 202 | 220.1 | 256.2 | 217.5 | 189.7 | n.d. | 155.4 | 11.96 | 17.58 | 15.04 | 24.36 | n.d. | 16.10 |
| 203 | 229.0 | 261.4 | 221.8 | 198.4 | 190.2 | 162.8 | 13.24 | 18.50 | 16.22 | 25.64 | 14.08 | 17.68 |
| 204 | 245.1 | 276.1 | 237.0 | 213.7 | 208.9 | 173.1 | 13.12 | 18.42 | 16.14 | 26.18 | 13.74 | 17.16 |
| 205 | n.d. | 254.0 | 212.4 | 187.4 | 166.4 | 148.4 | n.d. | 18.32 | 15.92 | 25.74 | 12.92 | 16.14 |
| 206 | n.d. | 263.6 | 220.1 | 197.1 | 184.6 | 156.9 | n.d. | 18.84 | 16.12 | 26.08 | 13.82 | 17.16 |
| 207 | 223.7 | 262.4 | 224.8 | 200.0 | 192.9 | 162.6 | 13.74 | 19.60 | 16.48 | 26.26 | 14.32 | 17.18 |
| 208 | 218.0 | 247.9 | 215.0 | 184.8 | 176.1 | 142.2 | 13.32 | 18.72 | 15.84 | 25.48 | 13.98 | 16.70 |
| 209 | 235.5 | 268.6 | 228.4 | 202.8 | 193.0 | 167.0 | 14.30 | 19.68 | 17.30 | 26.94 | 14.88 | 17.56 |
| 210 | 222.4 | 257.0 | 218.5 | 192.2 | 170.8 | 150.1 | 13.86 | 19.46 | 16.74 | 26.36 | 14.14 | 17.92 |
| 211 | 196.9 | 243.6 | 202.8 | n.d. | 160.5 | 128.2 | 13.08 | 18.50 | 15.28 | n.d. | 13.24 | 15.80 |
| 212 | 205.9 | 241.4 | 208.0 | 178.5 | 164.3 | 136.6 | 13.78 | 19.64 | 16.54 | 26.18 | 14.24 | 17.78 |
| 213 | 222.4 | n.d. | 219.9 | 193.9 | 183.8 | 159.4 | 13.40 | 18.86 | 16.44 | 25.68 | 14.02 | 17.10 |
| 214 | n.d. | 259.0 | 213.3 | n.d. | 182.6 | 152.3 | n.d. | 19.42 | 16.38 | n.d. | 14.58 | 16.86 |
| 215 | 207.0 | 246.7 | 206.0 | n.d. | 172.9 | 132.6 | 13.76 | 19.40 | 16.22 | n.d. | 14.48 | 16.20 |
| 216 | 228.1 | 259.3 | 221.6 | 195.2 | 188.0 | 155.3 | 13.16 | 18.42 | 15.90 | 25.96 | 13.88 | 16.28 |
| 217 | 233.8 | 266.4 | 229.5 | n.d. | 192.5 | 161.8 | 13.26 | 19.08 | 16.20 | n.d. | 13.90 | 16.92 |
| 218 | 220.1 | 251.9 | 217.5 | 190.2 | 170.4 | 151.3 | 12.72 | 18.48 | 15.72 | 25.66 | 13.26 | 16.28 |
| 219 | 222.2 | 252.1 | 210.9 | 189.9 | 172.1 | 148.0 | 12.74 | 18.56 | 15.76 | 25.04 | 13.02 | 16.06 |
| 220 | 227.9 | 265.4 | 227.6 | 202.5 | 187.1 | 163.8 | 13.02 | 18.54 | 16.28 | 25.92 | 14.12 | 16.48 |
| 221 | 216.2 | 248.4 | 211.8 | 183.6 | 173.6 | 140.0 | 13.38 | 18.96 | 16.08 | 25.56 | 13.82 | 17.46 |
| 222 | 230.8 | 264.5 | 227.2 | 202.2 | 195.3 | 168.8 | 12.66 | 18.28 | 15.54 | 25.66 | 13.28 | 16.66 |
| 223 | 229.5 | 266.2 | 228.7 | 199.3 | 182.7 | 160.5 | 12.66 | 18.20 | 15.38 | 24.72 | 13.04 | 16.54 |
| 224 | 191.4 | 241.2 | 193.9 | n.d. | 160.0 | 129.1 | 13.04 | 19.10 | 15.48 | n.d. | 13.44 | 16.06 |
| 225 | 233.0 | 265.1 | 226.7 | 204.0 | 190.8 | 161.4 | 13.24 | 18.50 | 15.80 | 25.60 | 14.12 | 16.86 |
| 226 | 221.9 | 251.6 | 213.4 | 190.5 | 180.8 | 149.1 | 13.46 | 18.44 | 16.04 | 25.44 | 13.86 | 16.46 |
| 227 | 227.4 | 257.0 | 219.0 | 193.0 | 180.0 | 158.6 | 13.54 | 18.64 | 16.24 | 26.28 | 14.38 | 16.80 |
| 228 | 230.4 | 260.8 | 223.9 | 197.8 | 189.9 | 157.2 | 13.24 | 18.94 | 16.02 | 25.74 | 14.22 | 17.22 |
| 229 | 246.1 | 277.7 | 235.4 | 211.4 | 207.9 | 178.1 | 13.44 | 19.40 | 16.56 | 25.84 | 14.22 | 17.40 |
| 230 | n.d. | 259.4 | 217.6 | 191.6 | 181.1 | 151.6 | n.d. | 18.84 | 16.02 | 26.22 | 14.00 | 16.54 |
| 231 | 226.3 | 257.5 | 219.7 | 193.6 | 180.9 | 153.2 | 13.10 | 18.46 | 15.56 | 24.90 | 13.28 | 16.12 |
| 232 | 236.8 | 266.8 | 235.1 | 201.1 | 196.7 | 165.9 | 13.06 | 18.84 | 15.96 | 26.10 | 14.10 | 16.58 |
| 233 | 220.6 | 262.8 | 220.7 | n.d. | 182.3 | 147.5 | 13.58 | 19.10 | 15.62 | n.d. | 13.76 | 15.88 |
| 234 | 219.2 | 255.3 | 215.5 | 193.0 | 183.2 | 151.4 | 13.16 | 19.02 | 15.92 | 25.72 | 13.78 | 16.58 |
| 235 | 208.9 | 241.9 | 203.9 | n.d. | 162.0 | 138.9 | 13.12 | 18.66 | 15.56 | n.d. | 13.30 | 17.28 |
| 236 | 231.8 | 265.7 | 225.0 | 200.0 | 191.7 | 163.5 | 14.80 | 20.22 | 17.40 | 27.14 | 15.32 | 19.08 |
| 237 | 209.4 | 245.6 | 205.8 | 186.1 | 173.8 | 141.2 | 13.34 | 18.66 | 16.08 | 25.74 | 14.12 | 17.16 |
| 238 | 218.6 | 254.7 | 221.6 | 191.1 | 176.3 | 151.0 | 13.82 | 19.18 | 16.66 | 26.82 | 14.32 | 18.24 |
| 239 | 210.2 | 249.6 | 215.4 | 187.3 | n.d. | 144.4 | 12.60 | 18.26 | 15.56 | 25.06 | n.d. | 16.62 |
| 240 | 216.6 | 251.8 | 213.7 | 188.1 | 171.6 | 146.5 | 14.02 | 19.32 | 16.60 | 26.26 | 14.62 | 17.10 |

TABLE 1-continued

Original Phenotypic Data for Grain Moisture and Yield from a Training Population

| | Grain yield | | | | | | Grain moisture | | | | | |
|---|---|---|---|---|---|---|---|---|---|---|---|---|
| Line ID | 7201 | 7212 | 7220 | 7330 | 8504 | 8644 | 7201 | 7212 | 7220 | 7330 | 8504 | 8644 |
| 241 | 234.9 | 272.0 | 238.1 | 207.7 | 194.3 | 174.7 | 13.48 | 19.14 | 16.24 | 25.58 | 13.72 | 17.32 |
| 242 | 238.8 | 269.1 | 235.4 | 205.9 | 190.4 | 163.3 | 13.14 | 18.90 | 16.22 | 26.08 | 13.50 | 17.60 |
| 243 | 226.0 | 259.3 | 221.5 | 194.2 | 185.7 | n.d. | 13.44 | 18.62 | 16.02 | 25.66 | 13.74 | n.d. |
| 244 | 205.5 | n.d. | 197.9 | 178.0 | 153.1 | 138.8 | 13.00 | n.d. | 15.68 | 25.18 | 12.96 | 16.64 |
| 245 | 234.1 | 274.1 | 235.6 | n.d. | 205.5 | 160.8 | 14.20 | 19.62 | 16.26 | n.d. | 14.40 | 17.50 |
| 246 | 198.7 | 231.7 | 196.8 | 172.3 | 157.0 | 128.1 | 12.50 | 18.20 | 15.50 | 24.92 | 13.40 | 16.44 |
| 247 | 240.2 | 271.4 | 231.7 | 207.1 | 195.2 | 166.2 | 14.12 | 19.70 | 16.92 | 26.68 | 14.70 | 17.44 |
| 248 | 210.6 | 250.0 | 212.3 | 184.7 | 173.0 | 142.9 | 12.90 | 18.94 | 15.86 | 25.52 | 13.90 | 17.12 |
| 249 | 223.4 | 253.5 | 219.6 | 191.9 | 178.4 | 149.9 | 12.92 | 18.32 | 15.72 | 25.42 | 13.44 | 16.98 |
| 250 | 215.7 | 253.4 | 212.6 | 189.0 | 173.8 | 147.6 | 13.28 | 18.82 | 16.00 | 26.28 | 14.16 | 16.44 |
| 251 | 212.5 | 255.2 | 209.2 | n.d. | 182.2 | 144.6 | 14.62 | 20.28 | 16.50 | n.d. | 15.18 | 16.96 |
| 252 | 224.4 | 266.9 | 219.4 | n.d. | 186.2 | 153.0 | 13.36 | 19.06 | 15.62 | n.d. | 13.74 | 16.98 |
| 253 | 224.3 | 258.6 | 219.5 | 197.1 | 186.9 | 155.8 | 13.72 | 19.22 | 16.94 | 26.20 | 14.72 | 17.56 |
| 254 | 227.4 | 265.1 | 221.6 | n.d. | 191.9 | n.d. | 13.84 | 19.36 | 16.18 | n.d. | 14.00 | n.d. |
| 255 | 218.1 | 248.8 | 211.6 | n.d. | 176.2 | 147.8 | 13.88 | 19.38 | 16.32 | n.d. | 14.44 | 16.96 |
| 256 | 225.5 | 260.8 | 221.5 | 196.8 | 179.9 | 156.8 | 13.68 | 19.54 | 16.44 | 26.74 | 13.96 | 17.62 |
| 257 | 221.3 | 251.2 | 213.2 | 189.6 | 171.9 | 147.5 | 13.34 | 18.74 | 16.26 | 25.82 | 13.80 | 17.02 |
| 258 | 212.1 | 252.8 | 213.9 | 187.3 | 171.1 | 144.9 | 12.68 | 18.14 | 15.44 | 25.58 | 13.02 | 15.74 |
| 259 | 223.6 | 256.6 | 224.8 | 194.6 | 184.4 | 160.9 | 14.14 | 19.42 | 16.88 | 26.42 | 14.56 | 17.84 |
| 260 | 211.2 | n.d. | 205.9 | 179.0 | 164.8 | 139.0 | 14.00 | 19.54 | 16.48 | 25.80 | 14.18 | 16.90 |
| 261 | 237.2 | 267.6 | 232.9 | 205.1 | 196.0 | 163.2 | 13.24 | 18.60 | 15.70 | 25.46 | 13.64 | 16.88 |
| 262 | 217.3 | 255.1 | 217.6 | 193.4 | 180.8 | 157.5 | 14.32 | 20.26 | 17.30 | 26.76 | 15.00 | 18.24 |
| 263 | n.d. | 259.7 | 226.1 | 194.5 | 185.4 | 164.7 | n.d. | 19.12 | 16.28 | 26.24 | 13.94 | 17.34 |
| 264 | 214.8 | 258.3 | 213.8 | n.d. | 181.9 | 137.7 | 12.44 | 18.18 | 14.82 | n.d. | 12.88 | 15.20 |
| 265 | 229.2 | 258.0 | 224.3 | 195.9 | 183.7 | 156.2 | 13.96 | 19.14 | 16.58 | 26.52 | 14.26 | 16.88 |
| 266 | 211.5 | 226.2 | 200.4 | 176.1 | 162.7 | 140.4 | 12.68 | 17.70 | 15.32 | 25.52 | 13.42 | 16.30 |
| 267 | 241.9 | 256.6 | 229.0 | 198.7 | 179.4 | 167.9 | 13.16 | 18.36 | 15.68 | 26.00 | 12.82 | 16.48 |
| 268 | 231.5 | 250.4 | 222.0 | 194.0 | 190.4 | 161.1 | 13.92 | 19.54 | 17.12 | 26.48 | 14.46 | 17.12 |
| 269 | 231.6 | 246.5 | 217.0 | 193.1 | 182.5 | 149.2 | 13.16 | 18.02 | 15.96 | 25.76 | 13.42 | 16.86 |
| 270 | 227.1 | 251.0 | 221.9 | 191.5 | 182.3 | 155.8 | 14.16 | 19.42 | 16.82 | 26.94 | 14.60 | 16.98 |
| 271 | 196.5 | 244.0 | 199.6 | n.d. | 160.4 | 131.0 | 13.72 | 19.50 | 16.08 | n.d. | 13.88 | 16.72 |
| 272 | 217.7 | 238.0 | 210.5 | 182.1 | 173.2 | 150.8 | 13.48 | 18.84 | 15.92 | 26.06 | 13.78 | 16.92 |
| 273 | 239.9 | 252.3 | 225.0 | 196.4 | 183.2 | 163.3 | 13.84 | 18.52 | 16.14 | 26.78 | 13.54 | 17.56 |
| 274 | 227.2 | 245.2 | 218.2 | 188.1 | 175.4 | 147.8 | 13.52 | 18.82 | 16.24 | 26.42 | 14.00 | 16.50 |
| 275 | 217.4 | 260.2 | 215.8 | n.d. | 170.3 | 140.3 | 13.52 | 18.86 | 15.56 | n.d. | 13.14 | 15.96 |
| 276 | 241.7 | 254.7 | 225.5 | 196.9 | 182.8 | 164.1 | 13.94 | 19.46 | 16.58 | 26.34 | 14.14 | 17.98 |
| 277 | 203.2 | 248.3 | 209.0 | n.d. | 166.0 | 140.5 | 13.08 | 18.72 | 15.56 | n.d. | 13.34 | 16.10 |
| 278 | 224.8 | 238.6 | 214.0 | 184.0 | 170.7 | 141.9 | 12.56 | 17.16 | 15.04 | 25.50 | 12.92 | 16.16 |
| 279 | 223.9 | 239.6 | 206.3 | 183.9 | 165.5 | 142.2 | 13.60 | 18.76 | 16.02 | 26.10 | 13.32 | 16.82 |
| 280 | 225.2 | 263.8 | 220.2 | n.d. | 187.8 | 155.3 | 13.46 | 19.36 | 15.76 | n.d. | 14.12 | 16.52 |
| 281 | 223.4 | 264.7 | 223.5 | n.d. | 183.0 | 150.1 | 13.26 | 19.08 | 15.50 | n.d. | 13.28 | 16.32 |
| 282 | 229.2 | 243.8 | 218.6 | 188.4 | 176.0 | 154.6 | 13.00 | 18.36 | 15.86 | 25.80 | 13.30 | 16.48 |
| 283 | 234.1 | 247.7 | 214.4 | 192.4 | 180.0 | 149.9 | 13.34 | 18.58 | 15.90 | 25.72 | 13.40 | 16.98 |
| 284 | 209.3 | 252.7 | 208.2 | n.d. | 167.6 | n.d. | 13.54 | 19.20 | 15.98 | n.d. | 14.34 | n.d. |
| 285 | 229.3 | 248.5 | 217.6 | 191.7 | 182.1 | 160.5 | 13.62 | 19.08 | 16.20 | 26.94 | 14.24 | 17.20 |
| 286 | 228.3 | n.d. | 218.9 | 194.4 | 183.9 | 159.0 | 13.24 | 18.42 | 16.00 | 26.40 | 13.86 | 16.30 |
| 287 | n.d. | 251.6 | 207.1 | n.d. | 177.8 | 138.5 | n.d. | 19.38 | 16.20 | n.d. | 14.24 | 15.86 |
| 288 | 224.5 | 238.2 | 210.4 | 183.8 | 168.8 | 148.4 | 12.86 | 17.94 | 15.50 | 26.14 | 13.68 | 15.90 |
| 289 | 234.5 | 255.4 | 222.7 | 195.3 | 184.6 | n.d. | 13.70 | 18.78 | 16.66 | 26.40 | 13.90 | n.d. |
| 290 | 243.4 | 261.5 | 232.3 | 203.3 | 194.1 | 167.9 | 12.48 | 17.72 | 15.38 | 25.40 | 13.06 | 16.00 |
| 291 | n.d. | n.d. | 222.9 | n.d. | 192.9 | 154.8 | n.d. | n.d. | 16.54 | n.d. | 14.68 | 16.86 |
| 292 | 235.8 | 255.0 | 221.7 | 196.3 | 187.7 | 159.0 | 13.70 | 19.12 | 16.40 | 26.40 | 14.22 | 16.54 |
| 293 | 229.1 | 251.3 | 226.1 | 197.7 | 178.7 | 164.7 | 12.62 | 18.02 | 15.32 | 25.42 | 12.78 | 16.20 |
| 294 | 215.1 | 255.0 | 208.3 | n.d. | 168.5 | n.d. | 13.72 | 19.56 | 15.86 | n.d. | 13.46 | n.d. |
| 295 | 234.9 | 246.4 | 222.6 | 194.4 | 186.6 | 158.8 | 13.42 | 18.42 | 16.16 | 26.26 | 13.80 | 16.84 |
| 296 | 253.4 | 266.0 | 236.0 | 208.0 | 207.7 | 171.4 | 14.70 | 20.08 | 17.22 | 27.18 | 15.22 | 18.72 |
| 297 | 235.6 | 248.6 | 219.7 | 191.7 | 182.1 | 155.4 | 13.38 | 18.66 | 16.12 | 26.64 | 13.70 | 16.86 |
| 298 | 220.9 | 240.3 | 206.9 | n.d. | 169.2 | 145.5 | 13.64 | 18.88 | 16.28 | n.d. | 14.04 | 16.66 |
| 299 | 228.5 | 248.4 | 221.9 | 190.4 | 174.9 | 150.5 | 12.44 | 17.90 | 15.06 | 25.00 | 13.22 | 15.32 |
| 300 | 234.4 | 251.7 | 221.1 | 189.2 | 174.7 | 153.7 | 13.28 | 18.20 | 15.56 | 26.18 | 13.16 | 16.44 |
| 301 | 231.7 | 247.0 | 215.5 | 190.2 | 181.4 | 150.3 | 13.66 | 18.82 | 16.36 | 26.68 | 14.06 | 16.24 |
| 302 | 231.7 | 249.2 | 220.8 | 188.6 | 181.0 | 150.9 | 13.12 | 18.04 | 15.42 | 25.54 | 13.52 | 16.28 |
| 303 | 201.7 | 223.0 | 191.9 | 165.3 | 144.3 | n.d. | 12.28 | 17.30 | 14.86 | 24.64 | 12.08 | n.d. |
| 304 | 204.5 | 251.5 | n.d. | n.d. | 167.5 | 131.2 | 12.96 | 18.72 | n.d. | n.d. | 13.22 | 16.10 |
| 305 | 228.9 | 242.3 | 212.2 | 189.3 | 177.1 | 154.6 | 13.40 | 18.46 | 15.88 | 26.78 | 13.84 | 16.88 |
| 306 | 214.1 | 232.3 | 205.8 | 179.3 | 167.4 | n.d. | 13.50 | 18.90 | 16.06 | 26.78 | 14.10 | n.d. |
| 307 | 220.9 | 247.0 | 213.6 | 188.7 | 167.2 | 145.6 | 12.98 | 18.26 | 15.78 | 25.84 | 12.96 | 16.96 |
| 308 | 222.6 | 236.6 | 206.7 | 184.4 | 171.0 | 150.9 | 12.82 | 17.60 | 15.32 | 25.42 | 13.18 | 16.20 |
| 309 | 217.6 | 238.3 | 206.9 | 184.8 | 172.1 | 145.5 | 12.48 | 17.60 | 15.38 | 25.10 | 12.88 | 16.02 |
| 310 | 226.8 | 245.9 | 209.1 | 189.1 | 170.8 | 145.0 | 12.74 | 17.64 | 15.36 | 25.34 | 13.32 | 15.74 |
| 311 | 207.7 | 251.8 | 210.8 | n.d. | 173.6 | 138.0 | 13.24 | 18.90 | 15.52 | n.d. | 13.48 | 15.40 |
| 312 | n.d. | 247.0 | 221.5 | 189.3 | 182.3 | 155.8 | n.d. | 19.20 | 16.50 | 27.12 | 14.44 | 16.88 |
| 313 | 213.7 | 233.6 | 202.5 | 178.7 | 173.1 | 142.0 | 14.76 | 20.24 | 17.36 | 27.68 | 15.32 | 18.44 |
| 314 | 215.5 | 261.5 | 213.3 | n.d. | 186.6 | 147.3 | 13.76 | 19.94 | 15.98 | n.d. | 14.62 | 16.96 |

TABLE 1-continued

Original Phenotypic Data for Grain Moisture and Yield from a Training Population

| | Grain yield | | | | | | Grain moisture | | | | | |
|---|---|---|---|---|---|---|---|---|---|---|---|---|
| Line ID | 7201 | 7212 | 7220 | 7330 | 8504 | 8644 | 7201 | 7212 | 7220 | 7330 | 8504 | 8644 |
| 315 | 201.6 | 248.0 | 203.7 | n.d. | 169.1 | n.d. | 13.24 | 19.12 | 15.56 | n.d. | 13.56 | n.d. |
| 316 | 236.1 | 253.3 | 231.8 | 198.3 | 188.7 | 163.9 | 14.02 | 19.28 | 16.82 | 26.96 | 14.46 | 17.18 |
| 317 | 227.2 | 244.3 | 212.8 | 184.4 | 177.4 | 147.7 | 13.42 | 18.96 | 16.50 | 26.68 | 14.12 | 16.36 |
| 318 | 247.3 | 263.6 | 235.3 | 205.0 | 202.1 | 169.3 | 14.92 | 20.38 | 17.62 | 27.58 | 15.34 | 18.08 |
| 319 | 210.2 | 255.7 | 212.3 | n.d. | 176.4 | 137.6 | 13.92 | 19.76 | 15.98 | n.d. | 14.10 | 17.22 |
| 320 | 228.2 | 241.5 | 210.5 | 186.8 | 176.2 | 149.6 | 13.08 | 18.24 | 16.02 | 26.44 | 13.56 | 15.94 |
| 321 | 234.1 | 252.3 | 216.2 | 194.0 | 177.0 | 157.3 | 12.64 | 17.64 | 15.28 | 25.76 | 12.46 | 16.46 |
| 322 | 211.4 | 238.3 | 205.2 | 179.6 | 168.9 | 138.3 | 12.46 | 17.64 | 15.04 | 25.16 | 13.06 | 16.02 |
| 323 | 207.1 | 223.5 | 197.3 | 170.7 | 156.0 | 131.9 | 12.84 | 17.98 | 15.62 | 26.00 | 13.42 | 16.92 |
| 324 | 214.6 | 253.3 | 214.5 | n.d. | 167.7 | 138.5 | 13.80 | 19.46 | 15.74 | n.d. | 13.42 | 16.62 |
| 325 | 233.9 | 250.2 | 221.4 | 192.3 | 178.5 | 151.3 | 13.02 | 17.94 | 15.48 | 25.40 | 13.42 | 16.26 |
| 326 | 214.8 | 257.0 | 210.5 | n.d. | 175.3 | 141.3 | 13.12 | 18.60 | 15.08 | n.d. | 13.38 | 15.40 |
| 327 | 235.0 | 251.2 | 220.5 | 193.9 | 188.2 | 160.3 | 13.98 | 19.14 | 16.24 | 26.76 | 14.02 | 17.08 |
| 328 | 234.3 | 251.7 | 218.1 | 194.1 | 181.6 | 154.9 | 13.90 | 19.12 | 16.62 | 26.72 | 14.16 | 16.80 |
| 329 | 212.6 | 250.7 | 208.6 | n.d. | 168.9 | 134.3 | 13.48 | 18.78 | 15.42 | n.d. | 13.96 | 15.92 |
| 330 | 235.1 | 248.9 | 223.1 | 192.3 | 186.7 | 154.0 | 13.74 | 18.86 | 16.02 | 26.14 | 14.10 | 17.02 |
| 331 | 219.6 | n.d. | 214.4 | n.d. | 183.5 | 144.1 | 13.22 | 18.94 | 15.98 | n.d. | 13.96 | 16.38 |
| 332 | 228.7 | n.d. | 227.0 | n.d. | 196.2 | 161.9 | 13.76 | n.d. | 16.26 | n.d. | 14.26 | 16.96 |
| 333 | 219.3 | 238.1 | 206.0 | 181.5 | 166.1 | 147.4 | 12.86 | 18.38 | 15.58 | 26.14 | 13.66 | 16.28 |
| 334 | 221.6 | 241.5 | 214.4 | 187.3 | 174.2 | 144.0 | 12.46 | 17.60 | 14.92 | 24.98 | 12.88 | 15.52 |
| 335 | 231.9 | 251.1 | 221.7 | 195.9 | 188.9 | 160.0 | 13.58 | 18.68 | 16.04 | 26.36 | 14.26 | 17.10 |
| 336 | 259.5 | n.d. | 244.3 | 214.1 | 206.7 | n.d. | 14.36 | n.d. | 17.14 | 26.96 | 15.06 | n.d. |
| 337 | 232.4 | 245.2 | 214.6 | 192.5 | 186.2 | 158.1 | 13.56 | 18.74 | 16.48 | 26.48 | 14.10 | 17.08 |
| 338 | 222.8 | 261.9 | 217.8 | n.d. | 183.5 | 149.1 | 13.76 | 19.90 | 16.08 | n.d. | 14.54 | 16.88 |
| 339 | 222.8 | 237.5 | 207.0 | 184.2 | 169.4 | 142.0 | 12.76 | 17.96 | 15.20 | 25.28 | 13.02 | 15.22 |
| 340 | 227.0 | 242.2 | 212.8 | 184.4 | 175.7 | n.d. | 13.08 | 18.16 | 15.50 | 26.08 | 13.40 | n.d. |
| 341 | 203.6 | 243.2 | 197.3 | n.d. | 158.6 | 128.8 | 13.08 | 18.80 | 14.98 | n.d. | 12.80 | 15.28 |
| 342 | 247.1 | 259.0 | 234.2 | 203.6 | 184.6 | 166.7 | 13.10 | 18.12 | 15.56 | 25.50 | 12.76 | 15.78 |
| 343 | n.d. | n.d. | 204.6 | n.d. | 160.3 | 130.9 | n.d. | 19.64 | 16.06 | n.d. | 14.02 | 16.12 |
| 344 | 212.8 | 256.3 | 211.8 | n.d. | n.d. | 139.0 | 13.10 | 18.84 | 15.56 | n.d. | n.d. | 15.50 |

Note:
grain yield is expressed in bushels/acre and gran moisture is expressed in percentage.
N.D.: not determined.

TABLE 2

BLUPs of 344 lines for Grain Moisture and Yield from a Training Population using a Mixed Model Approach

| line ID | Grain Yield | Grain Moisture | line ID | Grain Yield | Grain Moisture | line ID | Grain Yield | Grain Moisture | line ID | Grain Yield | Grain Moisture |
|---|---|---|---|---|---|---|---|---|---|---|---|
| 1 | 135.3 | 15.96 | 27 | 154.0 | 16.42 | 56 | 142.7 | 16.39 | 88 | 151.5 | 16.57 |
| 2 | 146.0 | 16.26 | 28 | 143.5 | 16.29 | 57 | 144.3 | 17.29 | 89 | 150.8 | 16.26 |
| 3 | 149.7 | 16.30 | 29 | 161.3 | 17.21 | 58 | 137.2 | 16.14 | 90 | 157.6 | 15.90 |
| 4 | 145.3 | 17.19 | 30 | 149.5 | 15.33 | 59 | 133.7 | 16.83 | 91 | 135.4 | 15.91 |
| 5 | 149.9 | 17.32 | 31 | 160.0 | 16.87 | 60 | 156.3 | 16.05 | 92 | 149.9 | 17.62 |
| 6 | 150.1 | 16.62 | 32 | 139.8 | 16.24 | 61 | 153.9 | 15.71 | 93 | 149.6 | 16.54 |
| 7 | 157.3 | 17.14 | 33 | 167.6 | 16.72 | 62 | 147.2 | 16.69 | 94 | 151.3 | 16.82 |
| 8 | 136.5 | 15.90 | 34 | 161.6 | 16.62 | 63 | 140.8 | 16.24 | 95 | 157.9 | 15.61 |
| 9 | 171.0 | 17.08 | 35 | 144.7 | 15.96 | 64 | 154.0 | 16.47 | 96 | 145.5 | 16.70 |
| 10 | 143.5 | 16.09 | 36 | 128.5 | 15.65 | 65 | 162.3 | 16.71 | 97 | 143.8 | 16.46 |
| 11 | 175.7 | 16.69 | 37 | 144.4 | 15.88 | 66 | 152.9 | 17.32 | 98 | 152.5 | 15.95 |
| 12 | 158.1 | 16.97 | 38 | 130.5 | 15.32 | 67 | 148.9 | 16.95 | 99 | 141.9 | 16.12 |
| 13 | 149.5 | 17.08 | 39 | 140.7 | 16.19 | 68 | 140.3 | 17.31 | 100 | 146.9 | 17.48 |
| 14 | 136.3 | 15.69 | 40 | 138.5 | 16.60 | 69 | 136.8 | 16.48 | 101 | 150.4 | 16.58 |
| 15 | 144.8 | 16.18 | 41 | 138.9 | 15.49 | 70 | 137.2 | 16.75 | 102 | 149.7 | 16.48 |
| 16 | 138.5 | 17.33 | 42 | 142.2 | 15.87 | 71 | 159.3 | 17.11 | 103 | 159.1 | 16.47 |
| 17 | 146.3 | 16.49 | 43 | 144.7 | 15.89 | 72 | 138.3 | 16.64 | 104 | 133.6 | 16.87 |
| 18 | 143.0 | 16.08 | 44 | 150.8 | 17.03 | 73 | 145.2 | 17.60 | 105 | 139.7 | 16.76 |
| 19 | 152.4 | 15.97 | 45 | 154.1 | 16.83 | 74 | 139.6 | 15.43 | 106 | 150.9 | 16.48 |
| 20 | 164.2 | 17.02 | 46 | 128.0 | 16.59 | 75 | 150.2 | 17.32 | 107 | 135.6 | 16.17 |
| 21 | 135.2 | 16.41 | 47 | 137.3 | 15.68 | 76 | 142.8 | 16.15 | 108 | 153.3 | 16.21 |
| 22 | 134.5 | 16.00 | 48 | 149.8 | 15.66 | 77 | 147.8 | 16.37 | 109 | 154.4 | 17.38 |
| 23 | 132.1 | 16.97 | 49 | 157.7 | 15.47 | 78 | 177.1 | 17.04 | 110 | 141.2 | 16.92 |
| 24 | 132.7 | 16.20 | 50 | 143.4 | 16.52 | 79 | 130.5 | 15.89 | 111 | 137.5 | 16.25 |
| 25 | 161.1 | 16.77 | 51 | 158.0 | 16.45 | 80 | 150.1 | 15.90 | 112 | 130.5 | 16.13 |
| 26 | 151.8 | 17.32 | 52 | 146.0 | 15.96 | 81 | 148.7 | 16.83 | 113 | 156.1 | 18.19 |
| 53 | 140.8 | 15.87 | 85 | 139.3 | 15.48 | 82 | 140.0 | 16.18 | 114 | 148.6 | 16.26 |
| 54 | 141.9 | 16.00 | 86 | 157.8 | 16.47 | 83 | 156.9 | 16.62 | 115 | 149.3 | 16.71 |
| 55 | 134.2 | 15.69 | 87 | 138.4 | 16.34 | 84 | 143.3 | 15.82 | 116 | 144.4 | 16.59 |

TABLE 2-continued

BLUPs of 344 lines for Grain Moisture and Yield from a Training Population using a Mixed Model Approach

| line ID | Grain Yield | Grain Moisture | line ID | Grain Yield | Grain Moisture |
|---|---|---|---|---|---|
| 117 | 146.3 | 17.47 | 149 | 143.0 | 17.03 |
| 118 | 155.1 | 17.09 | 150 | 139.7 | 16.98 |
| 119 | 143.6 | 16.62 | 151 | 146.2 | 17.27 |
| 120 | 155.5 | 16.42 | 152 | 152.6 | 16.34 |
| 121 | 144.4 | 16.45 | 153 | 141.2 | 15.94 |
| 122 | 150.4 | 17.35 | 154 | 153.8 | 15.89 |
| 123 | 153.5 | 16.48 | 155 | 150.1 | 16.15 |
| 124 | 161.0 | 17.05 | 156 | 142.4 | 16.80 |
| 125 | 155.4 | 15.95 | 157 | 148.4 | 16.18 |
| 126 | 149.8 | 16.84 | 158 | 147.9 | 16.23 |
| 127 | 156.6 | 17.38 | 159 | 151.2 | 16.70 |
| 128 | 136.0 | 15.92 | 160 | 135.5 | 16.11 |
| 129 | 158.2 | 17.26 | 161 | 143.1 | 15.61 |
| 130 | 139.4 | 16.41 | 162 | 176.3 | 16.18 |
| 131 | 150.4 | 16.05 | 163 | 141.7 | 18.02 |
| 132 | 159.7 | 16.63 | 164 | 143.7 | 17.13 |
| 133 | 152.8 | 17.15 | 165 | 158.2 | 16.20 |
| 134 | 172.7 | 17.69 | 166 | 151.0 | 17.16 |
| 135 | 145.3 | 15.77 | 167 | 142.5 | 16.93 |
| 136 | 146.3 | 16.85 | 168 | 153.1 | 16.96 |
| 137 | 154.6 | 17.94 | 169 | 162.0 | 16.54 |
| 138 | 156.1 | 16.93 | 170 | 134.7 | 15.71 |
| 139 | 149.3 | 18.08 | 171 | 140.8 | 16.40 |
| 140 | 153.1 | 16.36 | 172 | 152.4 | 16.80 |
| 141 | 133.2 | 16.67 | 173 | 164.6 | 17.28 |
| 142 | 145.0 | 16.52 | 174 | 146.6 | 16.79 |
| 143 | 162.5 | 16.21 | 175 | 145.7 | 15.07 |
| 144 | 148.5 | 17.22 | 176 | 155.3 | 16.19 |
| 145 | 157.5 | 16.20 | 177 | 165.5 | 16.83 |
| 146 | 158.1 | 17.01 | 178 | 144.8 | 16.69 |
| 147 | 147.7 | 16.37 | 179 | 139.3 | 16.93 |
| 148 | 137.3 | 16.21 | 180 | 148.7 | 16.22 |
| 181 | 144.2 | 16.34 | 213 | 153.8 | 16.62 |
| 182 | 151.6 | 15.46 | 214 | 151.5 | 16.97 |
| 183 | 155.1 | 16.48 | 215 | 138.8 | 16.78 |
| 184 | 145.6 | 17.00 | 216 | 155.2 | 16.32 |
| 185 | 164.8 | 16.33 | 217 | 161.7 | 16.64 |
| 186 | 150.3 | 16.00 | 218 | 147.8 | 16.09 |
| 187 | 147.9 | 16.80 | 219 | 146.8 | 15.94 |
| 188 | 154.4 | 17.47 | 220 | 159.6 | 16.44 |
| 189 | 143.6 | 17.36 | 221 | 143.3 | 16.58 |
| 190 | 145.5 | 16.40 | 222 | 161.9 | 16.08 |
| 191 | 151.2 | 16.31 | 223 | 158.5 | 15.84 |
| 192 | 158.5 | 16.77 | 224 | 129.2 | 16.22 |
| 193 | 135.6 | 16.31 | 225 | 160.6 | 16.40 |
| 194 | 166.2 | 16.98 | 226 | 148.7 | 16.34 |
| 195 | 157.9 | 16.91 | 227 | 153.2 | 16.68 |
| 196 | 161.1 | 16.33 | 228 | 157.3 | 16.60 |
| 197 | 150.2 | 16.74 | 229 | 172.9 | 16.84 |
| 198 | 149.7 | 17.09 | 230 | 151.7 | 16.55 |
| 199 | 137.4 | 16.43 | 231 | 152.6 | 15.98 |
| 200 | 144.0 | 16.34 | 232 | 164.1 | 16.49 |
| 201 | 163.7 | 16.51 | 233 | 152.0 | 16.38 |
| 202 | 150.6 | 15.41 | 234 | 150.4 | 16.41 |
| 203 | 157.8 | 16.60 | 235 | 136.9 | 16.37 |
| 204 | 172.4 | 16.51 | 236 | 160.1 | 17.96 |
| 205 | 145.4 | 16.07 | 237 | 141.4 | 16.56 |
| 206 | 155.7 | 16.63 | 238 | 149.7 | 17.18 |
| 207 | 158.3 | 16.95 | 239 | 144.4 | 15.98 |
| 208 | 145.0 | 16.39 | 240 | 145.7 | 17.00 |
| 209 | 163.0 | 17.44 | 241 | 167.2 | 16.62 |
| 210 | 149.3 | 17.09 | 242 | 164.2 | 16.61 |
| 211 | 132.4 | 16.00 | 243 | 154.2 | 16.36 |
| 212 | 137.0 | 17.04 | 244 | 133.4 | 16.06 |
| 245 | 166.7 | 17.14 | 277 | 139.1 | 16.16 |
| 246 | 128.9 | 15.91 | 278 | 143.4 | 15.65 |
| 247 | 165.6 | 17.26 | 279 | 141.3 | 16.48 |
| 248 | 143.3 | 16.42 | 280 | 155.6 | 16.62 |
| 249 | 150.3 | 16.20 | 281 | 154.1 | 16.28 |
| 250 | 146.3 | 16.54 | 282 | 149.3 | 16.20 |
| 251 | 146.2 | 17.43 | 283 | 150.6 | 16.37 |
| 252 | 155.1 | 16.53 | 284 | 141.5 | 16.72 |
| 253 | 154.4 | 17.07 | 285 | 152.4 | 16.90 |
| 254 | 157.8 | 16.80 | 286 | 154.8 | 16.42 |
| 255 | 146.0 | 16.95 | 287 | 143.8 | 16.61 |
| 256 | 154.2 | 17.01 | 288 | 143.4 | 16.07 |
| 257 | 146.7 | 16.54 | 289 | 155.3 | 16.73 |
| 258 | 144.7 | 15.85 | 290 | 164.1 | 15.76 |
| 259 | 154.8 | 17.22 | 291 | 157.9 | 17.04 |
| 260 | 138.5 | 16.84 | 292 | 156.5 | 16.71 |
| 261 | 164.0 | 16.31 | 293 | 155.3 | 15.81 |
| 262 | 151.1 | 17.63 | 294 | 143.7 | 16.62 |
| 263 | 157.3 | 16.80 | 295 | 154.6 | 16.53 |
| 264 | 146.7 | 15.55 | 296 | 170.6 | 17.83 |
| 265 | 155.2 | 16.91 | 297 | 152.9 | 16.60 |
| 266 | 134.2 | 15.90 | 298 | 142.2 | 16.67 |
| 267 | 159.4 | 16.15 | 299 | 149.9 | 15.59 |
| 268 | 155.5 | 17.12 | 300 | 151.6 | 16.20 |
| 269 | 150.8 | 16.26 | 301 | 150.2 | 16.67 |
| 270 | 152.3 | 17.16 | 302 | 151.2 | 16.06 |
| 271 | 132.3 | 16.75 | 303 | 123.3 | 15.17 |
| 272 | 143.1 | 16.54 | 304 | 137.4 | 16.12 |
| 273 | 157.3 | 16.76 | 305 | 148.3 | 16.58 |
| 274 | 147.9 | 16.62 | 306 | 137.3 | 16.71 |
| 275 | 146.3 | 16.21 | 307 | 144.8 | 16.19 |
| 276 | 158.2 | 17.09 | 308 | 143.1 | 15.84 |
| 309 | 141.9 | 15.67 | 327 | 155.5 | 16.89 |
| 310 | 145.4 | 15.78 | 328 | 153.2 | 16.91 |
| 311 | 142.0 | 16.12 | 329 | 140.7 | 16.31 |
| 312 | 150.6 | 17.02 | 330 | 154.0 | 16.68 |
| 313 | 138.5 | 17.93 | 331 | 148.5 | 16.48 |
| 314 | 150.2 | 17.00 | 332 | 161.0 | 16.86 |
| 315 | 137.8 | 16.36 | 333 | 140.8 | 16.21 |
| 316 | 159.2 | 17.13 | 334 | 144.8 | 15.49 |
| 317 | 146.6 | 16.71 | 335 | 155.6 | 16.70 |
| 318 | 167.4 | 17.95 | 336 | 177.4 | 17.47 |
| 319 | 144.0 | 16.95 | 337 | 152.2 | 16.78 |
| 320 | 146.4 | 16.27 | 338 | 152.3 | 16.98 |
| 321 | 152.6 | 15.79 | 339 | 141.6 | 15.67 |
| 322 | 138.2 | 15.66 | 340 | 145.6 | 16.12 |
| 323 | 129.2 | 16.19 | 341 | 132.3 | 15.82 |
| 324 | 143.3 | 16.58 | 342 | 162.9 | 15.88 |
| 325 | 152.0 | 15.99 | 343 | 134.5 | 16.65 |
| 326 | 145.3 | 15.94 | 344 | 144.2 | 16.10 |

As the model (1) was used to calculate BLUPs showed above, the variance components as showed in Table 3 can also be obtained. On one side, these variance components can be used to calculate heritability of one trait. On the other side, these variances will be used in the following calculation of effects of each marker.

TABLE 3

Variance Components for Grain Yield and Grain Moisture in a Training Population using REML based on a mixed model approach

| Variance | Grain Yield | Grain Moisture |
|---|---|---|
| $V_g$ | 94.27 | 0.32 |
| $V_e$ | 18.23 | 0.11 |

After the BLUPs of each line (Table 2) and variance components (Table 3) were calculated, the effects of 240 markers with respect to two traits, grain yield and grain moisture were estimated based on the BLUPs of lines and genotypes of these markers by following the approaches set forth hereinabove. For simplicity, these effects can be considered as the relative contribution of individual marker to the trait of interest. The effects, along with the position of each marker based on the BLUP of 344 lines were listed in Table 4. These effects were used for calculating GBV of lines in subsequent cycles of selection. The overall means for grain yield and grain moisture were 148.97 and 16.51, respectively.

TABLE 4

Effects of Markers Estimated from Training Populations

| Locus | Position (cM) | Yield Effect | Moisture Effect |
|---|---|---|---|
| CHROMOSOME 1 | | | |
| 1.1 | 0.0 | −0.01 | 0.01 |
| 1.2 | 5.9 | 0.49 | −0.01 |
| 1.3 | 8.3 | −0.81 | −0.03 |
| 1.4 | 23.1 | 1.59 | 0.02 |
| 1.5 | 27.4 | −1.27 | −0.08 |
| 1.6 | 28.5 | 0.27 | 0.12 |
| 1.7 | 41.3 | −1.18 | −0.03 |
| 1.8 | 42.5 | 1.04 | 0.05 |
| 1.9 | 45.8 | 1.06 | −0.01 |
| 1.10 | 62.3 | 1.16 | −0.03 |
| 1.11 | 67.3 | −0.68 | 0.04 |
| 1.12 | 76.4 | 0.23 | 0.07 |
| 1.13 | 93.1 | 0.86 | 0.07 |
| 1.14 | 95.0 | −0.28 | −0.05 |
| 1.15 | 105.7 | −0.26 | −0.03 |
| 1.16 | 118.8 | −1.06 | 0.05 |
| 1.17 | 127.0 | 0.84 | −0.03 |
| 1.18 | 134.9 | −0.04 | 0.09 |
| 1.19 | 144.3 | −0.78 | 0.03 |
| 1.20 | 157.3 | −0.77 | −0.03 |
| 1.21 | 163.6 | 2.44 | 0.00 |
| 1.22 | 169.8 | 0.88 | 0.04 |
| 1.23 | 177.2 | 0.89 | −0.05 |
| 1.24 | 183.3 | −1.01 | 0.05 |
| 1.25 | 184.3 | −0.51 | −0.02 |
| 1.26 | 186.0 | −1.06 | −0.01 |
| 1.27 | 188.9 | 0.59 | −0.01 |
| 1.28 | 206.1 | −0.12 | 0.10 |
| 1.29 | 214.9 | 0.94 | 0.01 |
| 1.30 | 220.6 | 0.11 | −0.01 |
| 1.31 | 224.6 | −0.17 | −0.01 |
| 1.32 | 233.2 | −0.85 | 0.00 |
| 1.33 | 238.4 | 0.34 | 0.00 |
| 1.34 | 243.2 | 0.99 | −0.04 |
| 1.35 | 248.9 | 3.54 | −0.03 |
| 1.36 | 254.5 | −1.17 | −0.04 |
| 1.37 | 256.4 | 0.45 | 0.05 |
| 1.38 | 258.7 | −0.34 | −0.01 |
| 1.39 | 275.6 | −2.02 | −0.03 |
| 1.40 | 294.4 | 1.00 | 0.03 |
| 1.41 | 306.7 | 1.42 | 0.01 |
| 1.42 | 315.6 | −0.88 | 0.02 |
| 1.43 | 316.2 | 0.10 | −0.05 |
| CHROMOSOME 2 | | | |
| 2.1 | 0.0 | −0.37 | 0.07 |
| 2.2 | 3.7 | −0.90 | −0.06 |
| 2.3 | 5.0 | 1.58 | −0.01 |
| 2.4 | 11.4 | −0.90 | 0.03 |
| 2.5 | 14.3 | 0.45 | −0.05 |
| 2.6 | 33.5 | 1.53 | 0.11 |
| 2.7 | 38.1 | 0.23 | 0.02 |
| 2.8 | 50.1 | −3.65 | −0.09 |
| 2.9 | 58.5 | 0.64 | −0.05 |
| 2.10 | 64.4 | 1.00 | 0.01 |
| 2.11 | 78.4 | 0.78 | 0.01 |
| 2.12 | 94.1 | −0.48 | 0.02 |
| 2.13 | 94.6 | 1.31 | 0.02 |
| 2.14 | 104.7 | −0.42 | 0.01 |
| 2.15 | 110.4 | 1.54 | 0.03 |
| 2.16 | 111.5 | −1.56 | 0.06 |
| 2.17 | 118.2 | 0.07 | 0.08 |
| 2.18 | 130.1 | 0.83 | 0.00 |
| 2.19 | 144.4 | 0.15 | 0.01 |
| 2.20 | 146.7 | −0.23 | 0.01 |
| 2.21 | 165.0 | −1.51 | −0.02 |
| 2.22 | 172.2 | 0.55 | 0.12 |
| 2.23 | 177.3 | −0.67 | −0.01 |
| 2.24 | 181.9 | 0.89 | −0.02 |
| 2.25 | 184.4 | 0.66 | −0.01 |
| 2.26 | 189.4 | −0.15 | 0.06 |
| 2.27 | 196.6 | 1.10 | 0.01 |
| CHROMOSOME 3 | | | |
| 3.1 | 0.0 | −0.69 | −0.01 |
| 3.2 | 12.3 | 1.28 | 0.03 |
| 3.3 | 17.1 | −0.81 | 0.04 |
| 3.4 | 28.1 | 1.20 | −0.02 |
| 3.5 | 50.6 | −0.96 | 0.03 |
| 3.6 | 61.5 | −0.14 | −0.03 |
| 3.7 | 72.4 | 2.05 | 0.01 |
| 3.8 | 76.8 | −0.50 | 0.03 |
| 3.9 | 80.7 | 1.11 | −0.01 |
| 3.10 | 83.6 | 0.06 | 0.00 |
| 3.11 | 93.6 | 0.02 | −0.01 |
| 3.12 | 105.8 | 0.41 | 0.02 |
| 3.13 | 107.5 | −0.92 | 0.07 |
| 3.14 | 125.6 | 1.43 | 0.08 |
| 3.15 | 126.0 | 1.08 | 0.05 |
| 3.16 | 128.9 | 0.00 | −0.06 |
| 3.17 | 134.5 | −1.43 | −0.06 |
| 3.18 | 137.6 | −0.39 | 0.05 |
| 3.19 | 140.8 | 0.10 | −0.13 |
| 3.20 | 144.8 | −0.20 | 0.02 |
| 3.21 | 157.3 | 0.00 | 0.06 |
| 3.22 | 175.2 | −0.59 | 0.03 |
| 3.23 | 175.6 | 0.57 | −0.04 |
| 3.24 | 175.9 | 0.18 | 0.01 |
| 3.25 | 179.2 | −0.85 | −0.07 |
| 3.26 | 205.2 | 1.62 | 0.04 |
| 3.27 | 210.9 | −2.08 | −0.07 |
| 3.28 | 222.1 | 0.80 | −0.01 |
| 3.29 | 225.4 | 0.21 | −0.02 |
| CHROMOSOME 4 | | | |
| 4.1 | 0.0 | 0.89 | 0.05 |
| 4.2 | 40.4 | 0.14 | 0.06 |
| 4.3 | 43.0 | −0.80 | −0.02 |
| 4.4 | 46.1 | 0.61 | −0.01 |
| 4.5 | 56.7 | −1.48 | 0.02 |
| 4.6 | 69.0 | 0.06 | 0.06 |
| 4.7 | 79.4 | 0.38 | −0.06 |
| 4.8 | 83.8 | 1.89 | 0.07 |
| 4.9 | 92.3 | −0.60 | −0.03 |
| 4.10 | 99.7 | −0.88 | 0.02 |
| 4.11 | 113.3 | 0.60 | −0.07 |
| 4.12 | 117.3 | 0.46 | 0.05 |
| 4.13 | 120.0 | 0.42 | −0.05 |
| 4.14 | 125.9 | 0.10 | 0.01 |
| 4.45 | 127.7 | 0.14 | 0.04 |
| 4.16 | 132.6 | −0.37 | −0.02 |
| 4.17 | 135.8 | 0.15 | −0.01 |
| 4.18 | 144.2 | −0.36 | 0.01 |
| 4.19 | 152.3 | 0.66 | 0.06 |
| 4.20 | 159.0 | 0.27 | −0.10 |
| 4.21 | 165.7 | 1.93 | 0.01 |
| 4.22 | 171.3 | −0.86 | 0.05 |
| 4.23 | 177.0 | 0.36 | 0.06 |
| 4.24 | 179.7 | −0.62 | −0.03 |
| CHROMOSOME 5 | | | |
| 5.1 | 0.0 | 0.27 | 0.02 |
| 5.2 | 1.5 | −0.73 | −0.02 |
| 5.3 | 10.0 | −0.57 | −0.12 |
| 5.4 | 13.1 | 1.47 | 0.06 |
| 5.5 | 14.0 | 0.63 | 0.06 |
| 5.6 | 17.5 | 0.08 | −0.03 |
| 5.7 | 19.8 | −1.08 | 0.00 |
| 5.8 | 24.2 | −1.41 | 0.02 |
| 5.9 | 25.3 | 1.25 | −0.01 |
| 5.10 | 29.0 | 0.94 | −0.01 |
| 5.11 | 34.2 | −0.45 | 0.00 |
| 5.12 | 42.6 | 0.15 | −0.01 |
| 5.13 | 42.8 | −0.84 | −0.01 |

TABLE 4-continued

Effects of Markers Estimated from Training Populations

| Locus | Position (cM) | Yield Effect | Moisture Effect |
|---|---|---|---|
| 5.14 | 52.6 | 0.93 | 0.05 |
| 5.15 | 78.3 | −0.48 | −0.05 |
| 5.16 | 80.6 | −0.32 | −0.03 |
| 5.17 | 86.8 | 1.50 | 0.00 |
| 5.18 | 93.0 | 0.90 | 0.04 |
| 5.19 | 95.1 | 0.12 | 0.01 |
| 5.20 | 106.2 | −0.36 | −0.07 |
| 5.21 | 110.9 | 0.22 | −0.04 |
| 5.22 | 115.1 | −0.47 | 0.05 |
| 5.23 | 129.1 | −1.97 | 0.00 |
| 5.24 | 130.7 | 1.35 | 0.04 |
| 5.25 | 135.5 | 0.62 | −0.05 |
| 5.26 | 138.7 | −0.01 | −0.02 |
| 5.27 | 142.6 | −0.48 | 0.05 |
| 5.28 | 143.4 | −0.24 | −0.02 |
| CHROMOSOME 6 | | | |
| 6.1 | 0.0 | −1.09 | −0.02 |
| 6.2 | 4.7 | 1.22 | 0.07 |
| 6.3 | 18.5 | 0.83 | 0.05 |
| 6.4 | 20.5 | −1.05 | −0.06 |
| 6.5 | 28.9 | 0.53 | 0.09 |
| 6.6 | 97.6 | −1.63 | 0.10 |
| 6.7 | 102.5 | 0.27 | −0.05 |
| 6.8 | 104.1 | 0.01 | 0.02 |
| 6.9 | 106.4 | 1.01 | 0.01 |
| 6.10 | 188.3 | −0.39 | −0.03 |
| 6.11 | 197.8 | 0.57 | −0.01 |
| 6.12 | 204.9 | −1.69 | −0.04 |
| 6.13 | 207.5 | 1.66 | 0.04 |
| 6.14 | 215.5 | 0.29 | 0.04 |
| 6.15 | 220.3 | 0.91 | −0.01 |
| 6.16 | 224.0 | 0.07 | 0.02 |
| 6.17 | 227.3 | 0.24 | 0.05 |
| 6.18 | 232.4 | 0.30 | 0.06 |
| 6.19 | 236.5 | −1.78 | −0.07 |
| 6.20 | 260.4 | 0.00 | −0.10 |
| CHROMOSOME 7 | | | |
| 7.1 | 0.0 | 1.09 | 0.01 |
| 7.2 | 1.8 | 0.83 | 0.03 |
| 7.3 | 2.1 | −1.15 | 0.05 |
| 7.4 | 5.1 | −1.10 | −0.06 |
| 7.5 | 31.0 | 1.10 | 0.05 |
| 7.6 | 49.5 | 1.22 | −0.02 |
| 7.7 | 51.2 | −2.58 | 0.04 |
| 7.8 | 58.1 | 0.42 | −0.03 |
| 7.9 | 59.6 | 0.73 | 0.02 |
| 7.10 | 61.5 | 0.15 | −0.01 |
| 7.11 | 62.2 | 1.10 | 0.01 |
| 7.12 | 65.0 | −0.66 | −0.09 |
| 7.13 | 69.8 | 0.85 | 0.01 |
| 7.14 | 75.9 | −1.50 | 0.00 |
| 7.15 | 90.6 | 0.28 | 0.06 |
| 7.16 | 98.0 | −0.54 | −0.03 |
| 7.17 | 115.4 | −0.08 | −0.04 |
| 7.18 | 118.5 | −0.22 | −0.04 |
| 7.19 | 124.5 | −0.68 | 0.07 |
| 7.20 | 129.2 | 0.45 | −0.04 |
| 7.21 | 130.5 | −0.88 | 0.00 |
| 7.22 | 133.7 | 1.13 | 0.02 |
| 7.23 | 152.1 | −0.38 | −0.02 |
| 7.24 | 166.9 | −1.81 | 0.00 |
| 7.25 | 175.2 | 1.94 | −0.04 |
| CHROMOSOME 8 | | | |
| 8.1 | 0.0 | −0.35 | 0.00 |
| 8.2 | 7.4 | 1.58 | 0.05 |
| 8.3 | 17.3 | 0.70 | −0.02 |
| 8.4 | 20.2 | −0.80 | −0.02 |
| 8.5 | 29.1 | 0.73 | 0.08 |
| 8.6 | 35.7 | −1.16 | −0.05 |
| 8.7 | 52.6 | −0.44 | 0.03 |
| 8.8 | 56.3 | −0.01 | 0.02 |
| 8.9 | 72.9 | −1.69 | −0.01 |
| 8.10 | 75.4 | 1.40 | −0.09 |
| 8.11 | 84.9 | 0.41 | 0.03 |
| 8.12 | 143.5 | −0.23 | −0.01 |
| 8.13 | 155.6 | 0.45 | −0.01 |
| 8.14 | 233.6 | 0.58 | 0.01 |
| 8.15 | 234.8 | −0.55 | −0.04 |
| 8.16 | 264.3 | −1.47 | −0.03 |
| 8.17 | 296.8 | 1.18 | 0.04 |
| 8.18 | 301.0 | −0.36 | −0.04 |
| CHROMOSOME 9 | | | |
| 9.1 | 0.0 | −0.28 | 0.00 |
| 9.2 | 2.6 | 1.16 | −0.03 |
| 9.3 | 11.1 | 1.17 | −0.02 |
| 9.4 | 16.7 | −2.06 | −0.02 |
| 9.5 | 34.1 | 1.18 | 0.05 |
| 9.6 | 34.6 | 0.27 | −0.04 |
| 9.7 | 39.6 | −0.72 | 0.01 |
| 9.8 | 44.7 | −0.89 | 0.03 |
| 9.9 | 53.8 | 0.05 | −0.06 |
| 9.10 | 59.7 | −2.35 | −0.05 |
| 9.11 | 71.6 | −0.32 | −0.02 |
| 9.12 | 74.4 | 1.04 | −0.05 |
| CHROMOSOME 10 | | | |
| 10.1 | 0.0 | −0.38 | −0.05 |
| 10.2 | 11.4 | 1.12 | 0.08 |
| 10.3 | 22.6 | 0.94 | 0.02 |
| 10.4 | 31.7 | 0.49 | −0.03 |
| 10.5 | 34.8 | −1.52 | 0.01 |
| 10.6 | 53.4 | 0.31 | 0.00 |
| 10.7 | 56.3 | −0.20 | −0.02 |
| 10.8 | 63.5 | −0.29 | 0.00 |
| 10.9 | 70.5 | 1.08 | 0.00 |
| 10.10 | 75.0 | −1.46 | −0.01 |
| 10.11 | 82.0 | 0.95 | 0.01 |
| 10.12 | 101.2 | 1.02 | 0.01 |
| 10.13 | 113.1 | 0.14 | −0.01 |
| 10.14 | 132.7 | −0.83 | 0.07 |

Once marker effects were calculated, GWS-SMART was used to select top 10 crosses from the DH population. The GPV of each cross was calculated by the simulated progeny from the cross. The genotype of each progeny was simulated using GWS-SMART, and the GBV of the progeny was then calculated using Equation (5). It must be noticed that the progeny simulated by GWS-SMART was actually $F_2$ progeny, since $F_1$ progeny has same type of genotype by crossing two parental lines from a DH population. This GPV can also be calculated based on the right tail or left tail of the distribution of GBVs of progeny from a certain cross. Totally, out of 344 lines in the DH population, 344*(344−1)/2=58996 crosses are simulated to generate 58996 subsequent populations using GWS-SMART. The GPVs of each cross was calculated in GWS-SMART. Based on the GPVs, top 10 crosses were eventually selected based on grain yield (see Table 5) and grain moisture (see Table 6), respectively.

TABLE 5

Selected Top 10 Crosses Based on GPV with respect to Grain Yield

| Cross ID | Line1 ID | Line2 ID | GPV |
|---|---|---|---|
| 1 | 41 | 311 | 207.60 |
| 2 | 41 | 138 | 207.62 |
| 3 | 95 | 2 | 207.65 |
| 4 | 192 | 2 | 207.65 |
| 5 | 311 | 138 | 207.81 |

TABLE 5-continued

Selected Top 10 Crosses Based on GPV with respect to Grain Yield

| Cross ID | Line1 ID | Line2 ID | GPV |
|---|---|---|---|
| 6 | 333 | 2 | 207.98 |
| 7 | 41 | 2 | 208.43 |
| 8 | 311 | 2 | 208.62 |
| 9 | 138 | 2 | 208.65 |
| 10 | 333 | 138 | 207.17 |

TABLE 6

Selected Top 10 Crosses Based on GPV with respect to Grain Moisture

| Cross ID | Line1 ID | Line2 ID | GPV |
|---|---|---|---|
| 1 | 342 | 317 | 18.368 |
| 2 | 242 | 163 | 18.368 |
| 3 | 178 | 319 | 18.368 |
| 4 | 216 | 319 | 18.369 |
| 5 | 177 | 186 | 18.369 |
| 6 | 30 | 163 | 18.369 |
| 7 | 63 | 279 | 18.370 |
| 8 | 95 | 312 | 18.370 |
| 9 | 285 | 82 | 18.370 |
| 10 | 60 | 82 | 18.371 |

GWS-SMART can be performed based on multiple trait implementations. The only difference between multi-trait GWS-SMART and single-trait GWS-SMART as described above is the way of calculating GBV for a progeny simulated from a certain cross. In this example, multi-trait GBV algorithm will be used if grain yield and grain moisture are considered in selection simultaneously as follows (Equations (6a) and (6b)). Based on multiple-trait GPVs, the top 10 crosses were selected and listed in Table 7.

TABLE 7

Selected Top 10 Crosses Based on multi-trait GPV

| Cross ID | Line1 ID | Line2 ID | Multi-trait GPV |
|---|---|---|---|
| 1 | 99 | 2 | 0.9909 |
| 2 | 95 | 2 | 0.9912 |
| 3 | 41 | 138 | 0.9914 |
| 4 | 192 | 2 | 0.9914 |
| 5 | 41 | 311 | 0.9915 |
| 6 | 138 | 311 | 0.9922 |
| 7 | 333 | 2 | 0.9935 |
| 8 | 41 | 2 | 0.9952 |
| 9 | 138 | 2 | 0.996 |
| 10 | 311 | 2 | 0.9961 |

REFERENCES

All references listed below, as well as all references cited in the instant disclosure, including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

Allard (1960) *Principles of Plant Breeding* John Wiley & Sons. Inc., New York, New York, United States of America.

Altschul et al. (1990) Basic local alignment search tool, *J Mol Biol* 215:403-410.

Altschul et al. (1997) Gapped BLAST and PSI-BLAST: a new generation of protein database search programs, *Nucleic Acids Res* 25:3389-3402.

Ausubel et al. (1999) *Short Protocols in Molecular Biology*, John Wiley & Sons, New York, N.Y., United States of America.

Beavis (1994) The power and deceit of QTL experiments: lessons from comparative QTL studies, pp. 250-266 in 49th Annual Corn and Sorghum Industry Research Conference. ASTA, Washington, D.C.

Churchill & Doerge (1994) Empirical threshold values for quantitative trait mapping, *Genetics* 138:963-971.

Devlin & Risch (1995) A comparison of linkage disequilibrium measures for fine-scale mapping, *Genomics* 29:311-322.

Gusfield (2002) Haplotyping as perfect phylogeny: conceptual framework and efficient solutions, in *Proceedings of RECOMB 2002: The 6th Annual International Conference on Computational Biology* 2002, ACM Press, Washington, D.C., United States of America, pages 166-175.

Harville (1977) Maximum Likelihood Approaches to Variance Component Estimation and to Related Problems, *J Am Stat Assoc* 72:320-338.

Hayes et al. (2009) Invited review: Genomic selection in dairy cattle: Progress and challenges. J Dairy Sci 92:433-443

Henderson (1975). "Best Linear Unbiased Estimation and Prediction under a Selection Model". *Biometrics* (International Biometric Society) 31 (2): 423-448

Jannink et al. (2010) Genomic selection in plant breeding: from theory to practice. Brief Funct Genomic 9:166-177

Jorde (2000) Linkage disequilibrium and the search for complex disease genes, *Genome Res* 10:1435-1444.

Lande & Thompson (1990) Efficiency of marker-assisted selection in the improvement of quantitative traits. Genetics 124:743-756

Larkin et al. (2007) Clustal W and Clustal X version 2.0, *Bioinformatics* 23:2947-2948.

Lorenzana & Bernardo (2009) Accuracy of genotypic value predictions for marker-based selection in biparental plant populations. Theor Appl Genet 120:151-161

Luan et al. (2009) The accuracy of genomic selection in Norwegian red cattle assessed by cross-validation. Genetics 183:1119-1126

Meuwissen et al. (2001) Prediction of total genetic value using genome-wide dense marker maps, Genetics 157: 1819-1829.

O'Connell (2000) Zero-recombinant haplotyping: applications to fine mapping using snps. *Genet Epidemiol* 19(Suppl 1):S64-70, 2000.

PCT International Patent Application Publication No. WO 2008/087185.

Qian & Beckmann (2002) Minimum-recombinant haplotyping in pedigrees, *Am J Hum Genet* 70:1434-1445.

Bernardo & Yu (2007) Prospects for genomewide selection for quantitative traits in maize, *Crop Science* 47:1082-1090.

Tijssen (1993) in *Laboratory Techniques in Biochemistry and Molecular Biology*, Elsevier, New York, N.Y., United States of America.

Utz et al. (1999) Bias and sampling error of the estimated proportion of genotypic variance explained by quantitative trait loci determined from experimental data in maize using cross validation and validation with independent samples. Genetics 154: 1839-1849

It will be understood that various details of the presently disclosed subject matter may be changed without departing from the scope of the presently disclosed subject matter.

Furthermore, the foregoing description is for the purpose of illustration only, and not for the purpose of limitation.

What is claimed is:

1. A method for increasing genetic gain in a breeding population, the method comprising:
   (a) providing effects with respect to a trait of interest of a plurality of genome-wide markers in a breeding population comprising a plurality of potential breeding partners;
   (b) selecting from the breeding population a first breeding pair comprising a first breeding partner and a second breeding partner, wherein crossing the first breeding partner and the second breeding partner would produce a segregating progeny population;
   (c) inferring or determining haplotypes with respect to the plurality of genome-wide markers for the first breeding partner and the second breeding partner;
   (d) simulating a cross between the first breeding partner and the second breeding partner to produce a progeny generation, each member of the progeny generation comprising a simulated genotype;
   (e) calculating a genetic potential value of the progeny generation, wherein the genetic potential value of the progeny generation is the mean of the genomic breeding values of the simulated genotypes of the member of the progeny generation;
   (f) repeating steps (b)-(e) one or more times, wherein in each iteration of step (b), the selecting comprises selecting a different first breeding partner, a different second breeding partner, or both from the breeding population;
   (g) ranking each simulated cross of step (d) based on the genetic potential values calculated in step (e); and
   (h) selecting one or more breeding pairs based on the ranking of step (g),
wherein crossing the breeding pair selected in step (g) is predicted to generate progeny with increased genetic gain, and further wherein the inferring step, the simulating step, or both are performed by a suitably-programmed computer.

2. The method of claim 1, further comprising repeating steps (b)-(e) and (g) such that at least one mean performance value calculated in step (e) exceeds a predetermined value.

3. The method of claim 1, wherein each breeding partner is a plant.

4. The method of claim 3, wherein the plant is selected from the group consisting of maize, wheat, barley, rice, sugar beet, sunflower, winter oilseed rape, canola, tomato, pepper, melon, watermelon, broccoli, cauliflower, Brussel sprouts, lettuce, spinach, sugar cane, coffee, cocoa, pine, poplar, eucalyptus, apple tree, and grape.

5. The method of claim 4, wherein the plant is maize.

6. The method of claim 1, wherein each breeding partner is an inbred individual.

7. The method of claim 1, wherein the breeding partners are the same individual.

8. The method of claim 1, wherein the one or more genetic markers are selected from the group consisting of a single nucleotide polymorphism (SNP), an insertion/deletion (indel), a simple sequence repeat (SSR), a restriction fragment length polymorphism (RFLP), a random amplified polymorphic DNA (RAPD), a cleaved amplified polymorphic sequence (CAPS) marker, a Diversity Arrays Technology (DArT) marker, an amplified fragment length polymorphism (AFLP), and combinations thereof.

9. The method of claim 1, wherein the one or more genetic markers comprise at least one marker present within every 5 cM, 3 cM, 2 cM, 1 cM, 0.5 cM, or 0.25 cM interval in the genomes of the breeding partners.

10. The method of claim 1, wherein the inferring step, the simulating step, the calculating step, or combinations thereof includes consideration of expected rates of recombination between adjacent genome-wide markers.

11. The method of claim 10, wherein the rate of recombination between the at least one of the one or more genetic markers and the genetic locus associated with the desired phenotype is zero.

12. The method of claim 1, wherein the simulating step comprises simulating at least 100, 500, or 1000 progeny in the progeny generation.

13. The method of claim 1 wherein the providing step comprises estimating effects with respect to the desired phenotype of the plurality of genome-wide markers based on phenotypic best linear unbiased predictions (BLUPs) and marker genotypic data in the biparental breeding population using genome-wide best linear unbiased prediction (GB-LUP).

14. The method of claim 1, wherein the inferring comprising employing a minimum recombination principle (MRP).

15. The method of claim 1, wherein the breeding population consists of n members and the repeating comprises simulating all n(n−1)/2 unique crosses of the members of the breeding population.

16. The method of claim 1, wherein the trait of interest comprises at least two independent traits of interest.

17. The method of claim 16, further comprising assigning to each independent trait of interest an importance value relative to the other independent traits.

18. The method of claim 1, wherein the selecting one or more breeding pairs based on the ranking of step (g) comprises selecting the breeding pairs for which the genetic potential values of the progeny generations are ranked in the top 20%, 10%, 5%, or 1%.

19. The method of claim 1, further comprising (i) crossing the one or more breeding pairs selected in step (h) to generate progeny with increased genetic gain.

20. A method for increasing the likelihood of producing a progeny individual having a desired phenotype, the method comprising:
   (a) providing effects with respect to a trait of interest of a plurality of genome-wide markers in a breeding population comprising a plurality of potential breeding partners;
   (b) selecting from the breeding population a first breeding pair comprising a first breeding partner and a second breeding partner, wherein crossing the first breeding partner and the second breeding partner would produce a segregating progeny population;
   (c) inferring haplotypes with respect to the plurality of genome-wide markers for the first breeding partner and the second breeding partner;
   (d) simulating a cross between the first breeding partner and the second breeding partner to produce a progeny generation, each member of the progeny generation comprising a simulated genotype;
   (e) calculating a genetic potential value of the progeny generation, wherein the genetic potential value of the progeny generation can be calculated as the mean of the genomic breeding values of the simulated genotypes of the member of the progeny generation, or it can be calculated based on the right tail or left tail of the distribution of the genomic breeding values;
   (f) repeating steps (b)-(e) one or more times, wherein in each iteration of step (b), the selecting comprises selecting a different first breeding partner, a different second breeding partner, or both from the breeding population;

(g) ranking each simulated cross of step (d) based on the genetic potential values calculated in step (e); and (h) selecting one or more breeding pairs based on the ranking of step (g), wherein the inferring step, the simulating step, or both are performed by a suitably-programmed computer, and further wherein each of the one or more breeding pairs is predicted to have an increased likelihood of producing a progeny having the desired phenotype versus other breeding pairs in the breeding population.

21. A method for generating a progeny individual having a desired genotype, the method comprising:

(a) providing effects with respect to a trait of interest of a plurality of genome-wide markers in a breeding population comprising a plurality of potential breeding partners;

(b) selecting from the breeding population a first breeding pair comprising a first breeding partner and a second breeding partner, wherein crossing the first breeding partner and the second breeding partner would produce a segregating progeny population;

(c) inferring haplotypes with respect to the plurality of genome-wide markers for the first breeding partner and the second breeding partner;

(d) simulating a cross between the first breeding partner and the second breeding partner to produce a progeny generation, each member of the progeny generation comprising a simulated genotype;

(e) calculating a genetic potential value of the progeny generation, wherein the genetic potential value of the progeny generation is the mean of the genomic breeding values of the simulated genotypes of the member of the progeny generation;

(f) repeating steps (b)-(e) one or more times, wherein in each iteration of step (b), the selecting comprises selecting a different first breeding partner, a different second breeding partner, or both from the breeding population;

(g) ranking each simulated cross of step (d) based on the genetic potential values calculated in step (e);

(h) selecting one or more breeding pairs based on the ranking of step (g); and (i) breeding the one or more breeding pairs selected in step (h) to generate a progeny individual having a desired genotype, wherein the inferring step, the simulating step, or both are performed by a suitably-programmed computer.

22. A method for increasing genetic gain in a breeding population, the method comprising:

(a) providing effects with respect to a trait of interest of a plurality of genome-wide markers in a breeding population comprising a plurality of potential breeding partners, wherein the providing step comprises estimating effects with respect to the desired phenotype of the plurality of genome-wide markers based on phenotypic best linear unbiased predictions (BLUPs) and marker genotypic data in the biparental breeding population using genome-wide best linear unbiased prediction (GBLUP), and further wherein the estimating comprising estimating genetic variance by restrained maximum likelihood estimation (REML) based on phenotypic data from multiple locations using Equation (1):

$$y_{ij} = \mu + G_i g_i + L_j b_j + e_{ij} \qquad (1),$$

where: $y_{ij}$ is a phenotype of line i at location j;

$\mu$ is an overall mean of the desired phenotype of a trait;

$G_i$ is an indicator variable representing the genotype of line i $g_i$ is a genotypic effect of line i following $g_i \sim N(0, \sigma g2)$;

(b) selecting from the breeding population a first breeding pair comprising a first breeding partner and a second breeding partner, wherein crossing the first breeding partner and the second breeding partner would produce a segregating progeny population;

(c) inferring or determining haplotypes with respect to the plurality of genome-wide markers for the first breeding partner and the second breeding partner;

(d) simulating a cross between the first breeding partner and the second breeding partner to produce a progeny generation, each member of the progeny generation comprising a simulated genotype;

(e) calculating a genetic potential value of the progeny generation, wherein the genetic potential value of the progeny generation is the mean of the genomic breeding values of the simulated genotypes of the member of the progeny generation;

(f) repeating steps (b)-(e) one or more times, wherein in each iteration of step (b), the selecting comprises selecting a different first breeding partner, a different second breeding partner, or both from the breeding population;

(q) ranking each simulated cross of step (d) based on the genetic potential values calculated in step (e); and (h) selecting one or more breeding pairs based on the ranking of step (g), wherein crossing the breeding pair selected in step (g) is predicted to generate progeny with increased genetic gain, and further wherein the inferring step, the simulating step, or both are performed by a suitably-programmed computer.

* * * * *